US012133897B2

(12) United States Patent
Johnston

(10) Patent No.: US 12,133,897 B2
(45) Date of Patent: Nov. 5, 2024

(54) GENE THERAPY DELIVERY OF PARKIN MUTANTS HAVING INCREASED ACTIVITY TO TREAT PARKINSON'S DISEASE

(71) Applicant: NysnoBio GT Neurology, LLC, Mill Valley, CA (US)

(72) Inventor: Jennifer Johnston, Mill Valley, CA (US)

(73) Assignee: NysnoBio GT Neurology, LLC, Mill Valley, CA (US)

( * ) Notice: Subject to any disclaimer, the term of this patent is extended or adjusted under 35 U.S.C. 154(b) by 260 days.

(21) Appl. No.: 17/327,562

(22) Filed: May 21, 2021

(65) Prior Publication Data

US 2022/0111077 A1    Apr. 14, 2022

Related U.S. Application Data

(60) Provisional application No. 63/028,335, filed on May 21, 2020.

(51) Int. Cl.
 *A61K 48/00* (2006.01)
(52) U.S. Cl.
 CPC ...... *A61K 48/0058* (2013.01); *A61K 48/0075* (2013.01)
(58) Field of Classification Search
 CPC . A61K 48/0058; A61K 48/0075; A61P 25/00; C12N 9/104
 See application file for complete search history.

(56) References Cited

U.S. PATENT DOCUMENTS

| 6,855,314 | B1 | 2/2005 | Chiorini et al. | |
| 7,998,667 | B1* | 8/2011 | Brice | C12Q 1/6883 435/6.12 |
| 9,464,311 | B2 | 10/2016 | Riley et al. | |
| 11,078,247 | B2* | 8/2021 | Fotin-Mleczek | C07K 14/505 |
| 2012/0064598 | A1* | 3/2012 | Brice | A61P 25/16 435/254.2 |
| 2019/0185823 | A1 | 6/2019 | Hewitt et al. | |

FOREIGN PATENT DOCUMENTS

| WO | WO-2009026116 A2 * | 2/2009 | ........... C12Q 1/6883 |
| WO | WO-2012067970 A2 | 5/2012 | |
| WO | WO-2019210325 A1 | 10/2019 | |
| WO | WO-2020072873 A1 | 4/2020 | |
| WO | WO-2021237158 A1 | 11/2021 | |

OTHER PUBLICATIONS

Kirik, D., and A. Björklund. "Viral vector delivery of parkin generates model results in rats." Gene Therapy 12: 727-729. (Year: 2005).*
Manfredsson, Fredric P., et al. "rAAV-mediated nigral human parkin over-expression partially ameliorates motor deficits via enhanced dopamine neurotransmission in a rat model of Parkinson's disease." Experimental neurology 207.2: 289-301. (Year: 2007).*
GenBank: AB009973.1. *Homo sapiens* parkin mRNA for Parkin, complete cds. Apr. 19, 2011. pp. 1-3. (Year: 2011).*
Aurnhammer et al. (2012). "Universal real-time PCR for the detection and quantification of adeno-associated virus serotype 2-derived inverted terminal repeat sequences." Human Gene Therapy, Part B: Methods. 23(1):18-28.
Fett et al. (2010). "Parkin Is Protective against Proteotoxic Stress in a Transgenic Zebrafish Model." PLoS ONE. 5(7): e11783.
Huang et al. (2016). "PINK1 and Parkin cooperatively protect neurons against constitutively active TRP channel-induced retinal degeneration in *Drosophila*." Cell Death and Disease. 7, e2179; doi:10.1038/cddis.2016.82.
Kirik et al. (2005). "Viral vector delivery of parkin generates model results in rats." Gene Therapy. 12, 727-729.
Kitada et al., "Mutations in the parkin gene cause autosomal recessive juvenile parkinsonism." Nature (1998); 392(6676): 605-608.
Klein et al., "Parkin is protective for substantia nigra dopamine neurons in a tau gene transfer neurodegeneration model," Neurosci Lett. Jun. 19, 2006; 401(1-2): 130-135, 10 pages total.
Lo Bianco et al. (2004). "Lentiviral vector delivery of parkin prevents dopaminergic degeneration in an α-synuclein rat model of Parkinson's disease." PNAS. 101(50): 17510-17515.
Madsen et al. (2021). "Interaction between Parkin and a-Synuclein in PARK2-Mediated Parkinson's Disease." Cells, 10, 283. https://doi.org/10.3390/cells10020283.
Manfredsson, F. et al., "rAAV-mediated nigral human parkin over-expression partially ameliorates motor deficits via enhanced dopamine neurotransmission in a rat model of Parkinson's disease," Experimental Neurology, Elsevier, Amsterdam, NL, Sep. 22, 2007, vol. 207, No. 2, pp. 289-301.
Matsumine et al., "A microdeletion of D6S305 in a family of autosomal recessive juvenile parkinsonism (PARK2)." Genomics (1998); 49(1): 143-146.
Muzyczka, N. "Use of adeno-Associated Virus as a General Transduction Vector for Mammalian Cells," Current Topics in Microbiology and Immunology 158:97-129 (1992).
Niethammer et al. (2018). "Gene therapy reduces Parkinson's disease symptoms by reorganizing functional brain connectivity." Science translational medicine. 10(469):eaau0713.
Paterna, J. et al., "DJ-1 and Parkin Modulate Dopamine-dependent Behavior and Inhibit MPTP-induced Nigral Dopamine Neuron Loss in Mice," Molecular Therapy, Apr. 1, 2007, vol. 15, No. 4, pp. 698-704.
PCT/US2021/033758, International Preliminary Report on Patentability mailed Nov. 17, 2022, 9 pages.
PCT/US2021/033758, International Search Report and Written Opinion mailed Oct. 21, 2021, 12 pages.

(Continued)

*Primary Examiner* — Arthur S Leonard
*Assistant Examiner* — Josephine M Gonzales
(74) *Attorney, Agent, or Firm* — COOLEY LLP

(57) ABSTRACT

The present disclosure provides novel gene therapy constructs comprising a PARK2 gene or activating variant and methods of administering to treat Parkinson's Disease or symptoms thereof.

22 Claims, 25 Drawing Sheets

Specification includes a Sequence Listing.

(56) References Cited

OTHER PUBLICATIONS

Popovic et al., "Ubiquitination in disease pathogenesis and treatment." Nature Medicine (2014); 20(11): 1242-1253.
Riley et al., "Structure and function of Parkin E3 ubiquitin ligase reveals aspects of RING and HECT ligases." Nat Commun. (2013); 4: 1982, pp. 1-9.
Wang and Maldonado, "The ubiquitin-proteasome system and its role in inflammatory and autoimmune diseases." Cell Mol Immunol (2006); 3(4): 255-261.
Yasuda et al. (2007). "Neuronal specificity of ?-synuclein toxicity and effect of Parkin coexpression in primates." Neuroscience. 144: 743-753.
Yasuda et al., "Parkin-Mediated Protection of Dopaminergic Neurons in a Chronic MPTP-Minipump Mouse Model of Parkinson Disease," J. Neuropath Exp Neurol, 2011, vol. 70, No. 8, pp. 686-697.
Yi W., et al., "The Landscape of Parkin Variants Reveals Pathogenic Mechanisms and Therapeutic Targets in Parkinson's Disease," Human Molecular Genetics, Sep. 2018, vol. 28(17), pp. 2811-2825.
Zolotukhin, et al., "Recombinant adeno-associated virus purification using novel methods improves infectious titer and yield." Gene Therapy (1999); vol. 6, pp. 973-985.
EP 21808868.0, Extended European Search Report mailed Jul. 24, 2024, 11 pages.
Fiesel et al. (2015). "Structural and Functional Impact of Parkinson Disease-Associated Mutations in the E3 Ubiquitin Ligase Parkin." Human Mutation, , vol. 36, No. 8, pp. 774-786.
Koyano et al. (2015). "Molecular mechanisms underlying PINK1 and Parkin catalyzed ubiquitylation of substrates on damaged mitochondria." Biochimica Et Biophysica Acta, Elsevier Science, vol. 1853, No. 10, pp. 2791-2796.
Van Rompuy et al. (Feb. 2024). "Long-Term Overexpression of Human Wild-Type and T240R Mutant Parkin in Rat Substantia Nigra Induces Progressive Dopaminergic Neurodegeneration." Journal of neuropathology and experimental neurology, vol. 73, No. 2, pp. 159-174.

\* cited by examiner

SEQUENCE LISTING

<160> NUMBER OF SEQ ID NOS: 52

<210> SEQ ID NO 1
<211> LENGTH: 1664
<212> TYPE: DNA
<213> ORGANISM: Homo sapiens

<400> SEQUENCE: 1

```
cttcttcttt tcctacagc tcctgggcaa cgtgctggtt attgtgctgt ctcatcattt     60
tggcaaagaa ttcctcgaag atccgaaggg gttcaagctt atcatcatga tagtgtttgt    120
caggttcaac tccagccatg gtttcccagt ggaggtcgat tctgacacca gcatcttcca    180
gctcaaggag gtggttgcta agcgacaggg ggttccggct gaccagttgc gtgtgatttt    240
cgcagggaag gagctgagga atgactggac tgtgcagaat tgtgacctgg atcagcagag    300
cattgttcac attgtgcaga gaccgtggag aaaaggtcaa gaaatgaatg caactggagg    360
cgacgacccc agaaacgcgg cgggaggctg tgagcgggag ccccagagct tgactcgggt    420
ggacctcagc agctcagtcc tcccaggaga ctctgtgggg ctggctgtca ttctgcacac    480
tgacagcagg aaggactcac caccagctgg aagtccagca ggtagatcaa tctacaacag    540
ctttttatgtg tattgcaaag gcccctgtca agagtgcagc cgggaaaaac tcagggtaca    600
gtgcagcacc tgcaggcagg caacgctcac cttgacccag gtccatctt gctgggatga    660
tgttttaatt ccaaaccgga tgagtggtga atgccaatcc ccacactgcc ctgggactag    720
tgcagaattt tctttaaat gtggagcaca ccccacctct gacaaggaaa catcagtagc    780
tttgcacctg atcgcaacaa atagtcggaa catcacttgc attacgtgca cagacgtcag    840
gagccccgtc ctggttttcc agtgcaactc ccgccacgtg atttgcttag actgtttcca    900
cttatactgt gtgacaagac tcaatgatcg gcagtttgtt cacgaccctc aacttggcta    960
ctccctgcct tgtgtggctg gctgtcccaa ctccttgatt aaagagctcc atcacttcag   1020
gattctggga gaagagcagt acaaccggta ccagcagtat ggtgcagagg agtgtgtcct   1080
gcagatgggg ggcgtgttat gcccccgccc tggctgtgga gcggggctgc tgccggagcc   1140
tgaccagagg aaagtcacct gcgaaggggg caatggcctg ggctgtgggt tgccttctg   1200
ccgggaatgt aaagaagcgt accatgaagg ggagtgcagt gccgtatttg aagcctcagg   1260
aacaactact caggcctaca gagtcgatga agagccgcc gagcaggctc gttgggaagc   1320
agcctccaaa gaaaccatca agaaaaccac caagcccctgt ccccgctgcc atgtaccagt   1380
ggaaaaaaat ggaggctgca tgcacatgaa gtgtccgcag ccccagtgca ggctcgagtg   1440
gtgctggaac tgtggctgcg agtggaaccg cgtctgcatg ggggaccact ggttcgacgt   1500
gtaaagtcga caacttgttt attgcagctt ataatggtta caaataaagc aatagcatca   1560
caaatttcac aaataaagca tttttttcac tgcattctag ttgtggtttg tccaaactca   1620
tcaatgtatc ttatcatgtc tggatcagat ctgaggaacc ccta                    1664
```

<210> SEQ ID NO 2
<211> LENGTH: 465
<212> TYPE: PRT
<213> ORGANISM: Homo sapiens

<400> SEQUENCE: 2

```
Met Ile Val Phe Val Arg Phe Asn Ser Ser His Gly Phe Pro Val Glu
 1               5                  10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
    50                  55                  60
```

```
Ser Ile Val His Ile Val Gln Arg Pro Trp Arg Lys Gly Gln Glu Met
 65                  70                  75                  80

Asn Ala Thr Gly Gly Asp Asp Pro Arg Asn Ala Ala Gly Gly Cys Glu
                 85                  90                  95

Arg Glu Pro Gln Ser Leu Thr Arg Val Asp Leu Ser Ser Val Leu
            100                 105                 110

Pro Gly Asp Ser Val Gly Leu Ala Val Ile Leu His Thr Asp Ser Arg
            115                 120                 125

Lys Asp Ser Pro Pro Ala Gly Ser Pro Ala Gly Arg Ser Ile Tyr Asn
            130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Gly Pro Ser Cys Trp Asp Asp Val Leu Ile Pro Asn Arg Met
            180                 185                 190

Ser Gly Glu Cys Gln Ser Pro His Cys Pro Gly Thr Ser Ala Glu Phe
            195                 200                 205

Phe Phe Lys Cys Gly Ala His Pro Thr Ser Asp Lys Glu Thr Ser Val
210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
                245                 250                 255

His Val Ile Cys Leu Asp Cys Phe His Leu Tyr Cys Val Thr Arg Leu
            260                 265                 270

Asn Asp Arg Gln Phe Val His Asp Pro Gln Leu Gly Tyr Ser Leu Pro
            275                 280                 285

Cys Val Ala Gly Cys Pro Asn Ser Leu Ile Lys Glu Leu His His Phe
            290                 295                 300

Arg Ile Leu Gly Glu Glu Gln Tyr Asn Arg Tyr Gln Gln Tyr Gly Ala
305                 310                 315                 320

Glu Glu Cys Val Leu Gln Met Gly Gly Val Leu Cys Pro Arg Pro Gly
                325                 330                 335

Cys Gly Ala Gly Leu Leu Pro Glu Pro Asp Gln Arg Lys Val Thr Cys
            340                 345                 350

Glu Gly Gly Asn Gly Leu Gly Cys Gly Phe Ala Phe Cys Arg Glu Cys
            355                 360                 365

Lys Glu Ala Tyr His Glu Gly Glu Cys Ser Ala Val Phe Glu Ala Ser
            370                 375                 380

Gly Thr Thr Thr Gln Ala Tyr Arg Val Asp Glu Arg Ala Ala Glu Gln
385                 390                 395                 400

Ala Arg Trp Glu Ala Ala Ser Lys Glu Thr Ile Lys Lys Thr Thr Lys
                405                 410                 415

Pro Cys Pro Arg Cys His Val Pro Val Glu Lys Asn Gly Gly Cys Met
            420                 425                 430

His Met Lys Cys Pro Gln Pro Gln Cys Arg Leu Glu Trp Cys Trp Asn
            435                 440                 445

Cys Gly Cys Glu Trp Asn Arg Val Cys Met Gly Asp His Trp Phe Asp
            450                 455                 460

Val
465
```

<210> SEQ ID NO 3
<211> LENGTH: 1664
<212> TYPE: DNA
<213> ORGANISM: Artificial Sequence
<220> FEATURE:
<223> OTHER INFORMATION: W183Y PARK2 mutant cDNA

<400> SEQUENCE: 3

```
cttcttctttt tcctacagc tcctgggcaa cgtgctggtt attgtgctgt ctcatcattt      60
tggcaaagaa ttcctcgaag atccgaaggg gttcaagctt atcatcatga tagtgtttgt     120
caggttcaac tccagccatg gtttcccagt ggaggtcgat tctgacacca gcatcttcca     180
gctcaaggag gtggttgcta agcgacaggg ggttccggct gaccagttgc gtgtgatttt     240
cgcagggaag gagctgagga tgactggac tgtgcagaat tgtgacctgg atcagcagag      300
cattgttcac attgtgcaga gaccgtggag aaaaggtcaa gaaatgaatg caactggagg     360
cgacgacccc agaaacgcgg cgggaggctg tgagcgggag ccccagagct tgactcgggt     420
ggacctcagc agctcagtcc tcccaggaga ctctgtgggg ctggctgtca ttctgcacac     480
tgacagcagg aaggactcac caccagctgg aagtccagca ggtagatcaa tctacaacag     540
cttttatgtg tattgcaaag gcccctgtca aagagtgcag ccgggaaaac tcagggtaca     600
gtgcagcacc tgcaggcagg caacgctcac cttgacccag ggtccatctt gctacgatga     660
tgttttaatt ccaaaccgga tgagtggtga atgccaatcc ccacactgcc ctgggactag     720
tgcagaattt ttctttaaat gtggagcaca ccccaccctct gacaaggaaa catcagtagc     780
tttgcacctg atcgcaacaa atagtcgaa catcacttgc attacgtgca cagacgtcag      840
gagccccgtc ctggttttcc agtgcaactc cgccacgtg atttgcttag actgtttcca      900
cttatactgt gtgacaagac tcaatgatcg gcagtttgtt cacgaccctc aacttggcta     960
ctccctgcct tgtgtggctg gctgtcccaa ctccttgatt aaagagctcc atcacttcag    1020
gattctggga gaagagcagt acaaccggta ccagcagtat ggtgcagagg agtgtgtcct    1080
gcagatgggg ggcgtgttat gccccgcgcc tggctgtgga gcggggctgc tgccggagcc    1140
tgaccagagg aaagtcacct gcgaaggggg caatggcctg gctgtgggt ttgccttctg     1200
ccgggaatgt aaagaagcgt accatgaagg ggagtgcagt gccgtatttg aagcctcagg    1260
aacaactact caggcctaca gagtcgatga agagccgcc gagcaggctc gttgggaagc     1320
agcctccaaa gaaaccatca agaaaccac caagccctgt ccccgctgcc atgtaccagt     1380
ggaaaaaaat ggaggctgca tgcacatgaa gtgtccgcag ccccagtgca ggctcgagtg    1440
gtgctggaac tgtggctgcg agtggaaccg cgtctgcatg ggggaccact ggttcgacgt    1500
gtaaagtcga caacttgttt attgcagctt ataatggtta caaataaagc aatagcatca    1560
caaatttcac aaataaagca ttttttcac tgcattctag ttgtggtttg tccaaactca     1620
tcaatgtatc ttatcatgtc tggatcagat ctgaggaacc ccta                    1664
```

<210> SEQ ID NO 4
<211> LENGTH: 465
<212> TYPE: PRT
<213> ORGANISM: Artificial Sequence
<220> FEATURE:
<223> OTHER INFORMATION: W183Y PARK2 mutant polypeptide

<400> SEQUENCE: 4

```
Met Ile Val Phe Val Arg Phe Asn Ser Ser His Gly Phe Pro Val Glu
  1               5                  10                  15

Val Asp Ser Asp Thr Ser Ile Phe Gln Leu Lys Glu Val Val Ala Lys
```

```
            20                  25                  30
Arg Gln Gly Val Pro Ala Asp Gln Leu Arg Val Ile Phe Ala Gly Lys
            35                  40                  45
Glu Leu Arg Asn Asp Trp Thr Val Gln Asn Cys Asp Leu Asp Gln Gln
50                  55                  60
Ser Ile Val His Ile Val Gln Arg Pro Trp Arg Lys Gly Gln Glu Met
65                  70                  75                  80
Asn Ala Thr Gly Gly Asp Asp Pro Arg Asn Ala Ala Gly Gly Cys Glu
                    85                  90                  95
Arg Glu Pro Gln Ser Leu Thr Arg Val Asp Leu Ser Ser Val Leu
                100                 105                 110
Pro Gly Asp Ser Val Gly Leu Ala Val Ile Leu His Thr Asp Ser Arg
                115                 120                 125
Lys Asp Ser Pro Pro Ala Gly Ser Pro Ala Gly Arg Ser Ile Tyr Asn
                130                 135                 140
Ser Phe Tyr Val Tyr Cys Lys Gly Pro Cys Gln Arg Val Gln Pro Gly
145                 150                 155                 160
Lys Leu Arg Val Gln Cys Ser Thr Cys Arg Gln Ala Thr Leu Thr Leu
                165                 170                 175
Thr Gln Gly Pro Ser Cys Tyr Asp Asp Val Leu Ile Pro Asn Arg Met
                180                 185                 190
Ser Gly Glu Cys Gln Ser Pro His Cys Pro Gly Thr Ser Ala Glu Phe
                195                 200                 205
Phe Phe Lys Cys Gly Ala His Pro Thr Ser Asp Lys Glu Thr Ser Val
                210                 215                 220
Ala Leu His Leu Ile Ala Thr Asn Ser Arg Asn Ile Thr Cys Ile Thr
225                 230                 235                 240
Cys Thr Asp Val Arg Ser Pro Val Leu Val Phe Gln Cys Asn Ser Arg
                245                 250                 255
His Val Ile Cys Leu Asp Cys Phe His Leu Tyr Cys Val Thr Arg Leu
                260                 265                 270
Asn Asp Arg Gln Phe Val His Asp Pro Gln Leu Gly Tyr Ser Leu Pro
                275                 280                 285
Cys Val Ala Gly Cys Pro Asn Ser Leu Ile Lys Glu Leu His His Phe
                290                 295                 300
Arg Ile Leu Gly Glu Glu Gln Tyr Asn Arg Tyr Gln Gln Tyr Gly Ala
305                 310                 315                 320
Glu Glu Cys Val Leu Gln Met Gly Gly Val Leu Cys Pro Arg Pro Gly
                325                 330                 335
Cys Gly Ala Gly Leu Leu Pro Glu Pro Asp Gln Arg Lys Val Thr Cys
                340                 345                 350
Glu Gly Gly Asn Gly Leu Gly Cys Gly Phe Ala Phe Cys Arg Glu Cys
                355                 360                 365
Lys Glu Ala Tyr His Glu Gly Glu Cys Ser Ala Val Phe Glu Ala Ser
                370                 375                 380
Gly Thr Thr Thr Gln Ala Tyr Arg Val Asp Glu Arg Ala Ala Glu Gln
385                 390                 395                 400
Ala Arg Trp Glu Ala Ala Ser Lys Glu Thr Ile Lys Lys Thr Thr Lys
                405                 410                 415
Pro Cys Pro Arg Cys His Val Pro Val Glu Lys Asn Gly Gly Cys Met
                420                 425                 430
His Met Lys Cys Pro Gln Pro Gln Cys Arg Leu Glu Trp Cys Trp Asn
                435                 440                 445
```

Cys Gly Cys Glu Trp Asn Arg Val Cys Met Gly Asp His Trp Phe Asp
    450                 455                 460

Val
465

<210> SEQ ID NO 5
<211> LENGTH: 1664
<212> TYPE: DNA
<213> ORGANISM: Artificial Sequence
<220> FEATURE:
<223> OTHER INFORMATION: F208Y PARK2 mutant cDNA

<400> SEQUENCE: 5

```
cttcttcttt tcctacagc tcctgggcaa cgtgctggtt attgtgctgt ctcatcattt       60
tggcaaagaa ttcctcgaag atccgaaggg gttcaagctt atcatcatga tagtgtttgt     120
caggttcaac tccagccatg gtttcccagt ggaggtcgat tctgacacca gcatcttcca     180
gctcaaggag gtggttgcta agcgacaggg ggttccggct gaccagttgc gtgtgatttt     240
cgcagggaag gagctgagga atgactggac tgtgcagaat tgtgacctgg atcagcagag     300
cattgttcac attgtgcaga gaccgtggag aaaaggtcaa gaaatgaatg caactggagg     360
cgacgacccc agaaacgcgg cgggaggctg tgagcgggag ccccagagct tgactcgggt     420
ggacctcagc agctcagtcc tcccaggaga ctctgtgggg ctggctgtca ttctgcacac     480
tgacagcagg aaggactcac caccagctgg aagtccagca ggtagatcaa tctacaacag     540
cttttatgtg tattgcaaag gcccctgtca aagagtgcag ccgggaaaac tcagggtaca     600
gtgcagcacc tgcaggcagg caacgctcac cttgacccag ggtccatctt gctgggatga     660
tgtttttaatt ccaaaccgga tgagtggtga atgccaatcc ccacactgcc ctgggactag     720
tgcagaatac ttctttaaat gtggagcaca ccccacctct gacaaggaaa catcagtagc     780
tttgcacctg atcgcaacaa atagtcgaa catcacttgc attacgtgca cagacgtcag     840
gagccccgtc ctggttttcc agtgcaactc ccgccacgtg atttgcttag actgtttcca     900
cttatactgt gtgacaagac tcaatgatcg gcagtttgtt cacgacccctc aacttggcta     960
ctccctgcct tgtgtggctg gctgtcccaa ctccttgatt aaagagctcc atcacttcag    1020
gattctggga gaagagcagt acaaccggta ccagcagtat ggtgcagagg agtgtgtcct    1080
gcagatgggg ggcgtgttat gccccgccc tggctgtgga gcggggctgc tgccggagcc    1140
tgaccagagg aaagtcacct gcgaagggg caatggcctg gctgtgggt ttgccttctg    1200
ccgggaatgt aaagaagcgt accatgaagg ggagtgcagt gccgtatttg aagcctcagg    1260
aacaactact caggcctaca gagtcgatga aagagccgcc gagcaggctc gttgggaagc    1320
agcctccaaa gaaaccatca agaaaaccac caagccctgt ccccgctgcc atgtaccagt    1380
ggaaaaaaat ggaggctgca tgcacatgaa gtgtccgcag ccccagtgca ggctcgagtg    1440
gtgctggaac tgtggctgcg agtggaaccg cgtctgcatg ggggaccact ggttcgacgt    1500
gtaaagtcga caacttgttt attgcagctt ataatggtta caaataaagc aatagcatca    1560
caaatttcac aaataaagca tttttttcac tgcattctag ttgtggtttg tccaaactca    1620
tcaatgtatc ttatcatgtc tggatcagat ctgaggaacc ccta                      1664
```

<210> SEQ ID NO 6
<211> LENGTH: 465
<212> TYPE: PRT
<213> ORGANISM: Artificial Sequence
<220> FEATURE:

<223> OTHER INFORMATION: F208Y PARK2 mutant polypeptide

<400> SEQUENCE: 6

```
Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Ala Lys
            20                  25                  30

Arg Gln Gly Val Pro Ala Asp Gln Leu Arg Val Ile Phe Ala Gly Lys
            35                  40                  45

Glu Leu Arg Asn Asp Trp Thr Val Gln Asn Cys Asp Leu Asp Gln Gln
50                  55                  60

Ser Ile Val His Ile Val Gln Arg Pro Trp Arg Lys Gly Gln Glu Met
65                  70                  75                  80

Asn Ala Thr Gly Gly Asp Asp Pro Arg Asn Ala Ala Gly Gly Cys Glu
                85                  90                  95

Arg Glu Pro Gln Ser Leu Thr Arg Val Asp Leu Ser Ser Ser Val Leu
            100                 105                 110

Pro Gly Asp Ser Val Gly Leu Ala Val Ile Leu His Thr Asp Ser Arg
            115                 120                 125

Lys Asp Ser Pro Pro Ala Gly Ser Pro Ala Gly Arg Ser Ile Tyr Asn
130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Gly Pro Ser Cys Trp Asp Asp Val Leu Ile Pro Asn Arg Met
            180                 185                 190

Ser Gly Glu Cys Gln Ser Pro His Cys Pro Gly Thr Ser Ala Glu Tyr
            195                 200                 205

Phe Phe Lys Cys Gly Ala His Pro Thr Ser Asp Lys Glu Thr Ser Val
210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
                245                 250                 255

His Val Ile Cys Leu Asp Cys Phe His Leu Tyr Cys Val Thr Arg Leu
            260                 265                 270

Asn Asp Arg Gln Phe Val His Asp Pro Gln Leu Gly Tyr Ser Leu Pro
            275                 280                 285

Cys Val Ala Gly Cys Pro Asn Ser Leu Ile Lys Glu Leu His His Phe
290                 295                 300

Arg Ile Leu Gly Glu Glu Gln Tyr Asn Arg Tyr Gln Gln Tyr Gly Ala
305                 310                 315                 320

Glu Glu Cys Val Leu Gln Met Gly Gly Val Leu Cys Pro Arg Pro Gly
                325                 330                 335

Cys Gly Ala Gly Leu Leu Pro Glu Pro Asp Gln Arg Lys Val Thr Cys
            340                 345                 350

Glu Gly Gly Asn Gly Leu Gly Cys Gly Phe Ala Phe Cys Arg Glu Cys
            355                 360                 365

Lys Glu Ala Tyr His Glu Gly Glu Cys Ser Ala Val Phe Glu Ala Ser
370                 375                 380

Gly Thr Thr Thr Gln Ala Tyr Arg Val Asp Glu Arg Ala Ala Glu Gln
385                 390                 395                 400
```

```
Ala Arg Trp Glu Ala Ala Ser Lys Glu Thr Ile Lys Lys Thr Thr Lys
            405                 410                 415

Pro Cys Pro Arg Cys His Val Pro Val Glu Lys Asn Gly Gly Cys Met
        420                 425                 430

His Met Lys Cys Pro Gln Pro Gln Cys Arg Leu Glu Trp Cys Trp Asn
            435                 440                 445

Cys Gly Cys Glu Trp Asn Arg Val Cys Met Gly Asp His Trp Phe Asp
        450                 455                 460

Val
465

<210> SEQ ID NO 7
<211> LENGTH: 1664
<212> TYPE: DNA
<213> ORGANISM: Artificial Sequence
<220> FEATURE:
<223> OTHER INFORMATION: F463Y PARK2 mutant cDNA

<400> SEQUENCE: 7
```

| | | | | | |
|---|---|---|---|---|---|
| cttcttcttt | ttcctacagc | tcctgggcaa | cgtgctggtt | attgtgctgt | ctcatcattt | 60 |
| tggcaaagaa | ttcctcgaag | atccgaaggg | gttcaagctt | atcatcatga | tagtgtttgt | 120 |
| caggttcaac | tccagccatg | gtttcccagt | ggaggtcgat | tctgacacca | gcatcttcca | 180 |
| gctcaaggag | gtggttgcta | agcgacaggg | ggttccggct | gaccagttgc | gtgtgatttt | 240 |
| cgcagggaag | gagctgagga | atgactggac | tgtgcagaat | tgtgacctgg | atcagcagag | 300 |
| cattgttcac | attgtgcaga | gaccgtggag | aaaaggtcaa | gaaatgaatg | caactggagg | 360 |
| cgacgacccc | agaaacgcgg | cgggaggctg | tgagcgggag | ccccagagct | tgactcgggt | 420 |
| ggacctcagc | agctcagtcc | tcccaggaga | ctctgtgggg | ctggctgtca | ttctgcacac | 480 |
| tgacagcagg | aaggactcac | caccagctgg | aagtccagca | ggtagatcaa | tctacaacag | 540 |
| cttttatgtg | tattgcaaag | gcccctgtca | aagagtgcag | ccgggaaaac | tcagggtaca | 600 |
| gtgcagcacc | tgcaggcagg | caacgctcac | cttgacccag | gtccatcttc | tgggatga | 660 |
| tgttttaatt | ccaaaccgga | tgagtggtga | atgccaatcc | ccacactgcc | ctgggactag | 720 |
| tgcagaattt | ttctttaaat | gtggagcaca | ccccacctct | gacaaggaaa | catcagtagc | 780 |
| tttgcacctg | atcgcaacaa | atagtcggaa | catcacttgc | attacgtgca | cagacgtcag | 840 |
| gagccccgtc | ctggttttcc | agtgcaactc | ccgccacgtg | atttgcttag | actgtttcca | 900 |
| cttatactgt | gtgacaagac | tcaatgatcg | gcagtttgtt | cacgacccctc | aacttggcta | 960 |
| ctccctgcct | tgtgtggctg | gctgtcccaa | tccttgatt | aaagagctcc | atcacttcag | 1020 |
| gattctggga | gaagagcagt | acaaccggta | ccagcagtat | ggtgcagagg | agtgtgtcct | 1080 |
| gcagatgggg | ggcgtgttat | gccccgcc | tggctgtgga | gcggggctgc | tgccggagcc | 1140 |
| tgaccagagg | aaagtcacct | gcgaagggg | caatggcctg | ggctgtgggt | ttgccttctg | 1200 |
| ccgggaatgt | aaagaagcgt | accatgaagg | ggagtgcagt | gccgtatttg | aagcctcagg | 1260 |
| aacaactact | caggcctaca | gagtcgatga | aagagccgcc | gagcaggctc | gttgggaagc | 1320 |
| agcctccaaa | gaaaccatca | agaaaaccac | caagccctgt | ccccgctgcc | atgtaccagt | 1380 |
| ggaaaaaaat | ggaggctgca | tgcacatgaa | gtgtccgcag | ccccagtgca | ggctcgagtg | 1440 |
| gtgctggaac | tgtggctgcg | agtggaaccg | cgtctgcatg | ggggaccact | ggtacgacgt | 1500 |
| gtaaagtcga | caacttgttt | attgcagctt | ataatggtta | caaataaagc | aatagcatca | 1560 |
| caaatttcac | aaataaagca | ttttttttcac | tgcattctag | ttgtggtttg | tccaaactca | 1620 | tcaatgtatc ttatcatgtc tggatcagat ctgaggaacc ccta          1664

<210> SEQ ID NO 8
<211> LENGTH: 465
<212> TYPE: PRT
<213> ORGANISM: Artificial Sequence
<220> FEATURE:
<223> OTHER INFORMATION: F463Y PARK2 mutant polypeptide

<400> SEQUENCE: 8

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
    50                  55                  60

Ser Ile Val His Ile Val Gln Arg Pro Trp Arg Lys Gly Gln Glu Met
65                  70                  75                  80

Asn Ala Thr Gly Gly Asp Asp Pro Arg Asn Ala Ala Gly Gly Cys Glu
                85                  90                  95

Arg Glu Pro Gln Ser Leu Thr Arg Val Asp Leu Ser Ser Ser Val Leu
            100                 105                 110

Pro Gly Asp Ser Val Gly Leu Ala Val Ile Leu His Thr Asp Ser Arg
        115                 120                 125

Lys Asp Ser Pro Pro Ala Gly Ser Pro Ala Gly Arg Ser Ile Tyr Asn
    130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Gly Pro Ser Cys Trp Asp Asp Val Leu Ile Pro Asn Arg Met
            180                 185                 190

Ser Gly Glu Cys Gln Ser Pro His Cys Pro Gly Thr Ser Ala Glu Phe
        195                 200                 205

Phe Phe Lys Cys Gly Ala His Pro Thr Ser Asp Lys Glu Thr Ser Val
    210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
                245                 250                 255

His Val Ile Cys Leu Asp Cys Phe His Leu Tyr Cys Val Thr Arg Leu
            260                 265                 270

Asn Asp Arg Gln Phe Val His Asp Pro Gln Leu Gly Tyr Ser Leu Pro
        275                 280                 285

Cys Val Ala Gly Cys Pro Asn Ser Leu Ile Lys Glu Leu His His Phe
    290                 295                 300

Arg Ile Leu Gly Glu Glu Gln Tyr Asn Arg Tyr Gln Gln Tyr Gly Ala
305                 310                 315                 320

Glu Glu Cys Val Leu Gln Met Gly Gly Val Leu Cys Pro Arg Pro Gly
                325                 330                 335

Cys Gly Ala Gly Leu Leu Pro Glu Pro Asp Gln Arg Lys Val Thr Cys
            340                 345                 350

Glu Gly Gly Asn Gly Leu Gly Cys Gly Phe Ala Phe Cys Arg Glu Cys

```
                  355              360              365
Lys Glu Ala Tyr His Glu Gly Glu Cys Ser Ala Val Phe Glu Ala Ser
    370              375              380

Gly Thr Thr Thr Gln Ala Tyr Arg Val Asp Glu Arg Ala Ala Glu Gln
385              390              395              400

Ala Arg Trp Glu Ala Ala Ser Lys Glu Thr Ile Lys Lys Thr Thr Lys
                405              410              415

Pro Cys Pro Arg Cys His Val Pro Val Glu Lys Asn Gly Gly Cys Met
            420              425              430

His Met Lys Cys Pro Gln Pro Gln Cys Arg Leu Glu Trp Cys Trp Asn
        435              440              445

Cys Gly Cys Glu Trp Asn Arg Val Cys Met Gly Asp His Trp Tyr Asp
    450              455              460

Val
465

<210> SEQ ID NO 9
<211> LENGTH: 4718
<212> TYPE: DNA
<213> ORGANISM: Dependoparvovirus Adeno-associated virus - 1

<400> SEQUENCE: 9
ttgcccactc cctctctgcg cgctcgctcg ctcggtgggg cctgcggacc aaaggtccgc    60
agacggcaga gctctgctct gccggcccca ccgagcgagc gagcgcgcag agagggagtg   120
ggcaactcca tcactagggg taatcgcgaa gcgcctccca cgctgccgcg tcagcgctga   180
cgtaaattac gtcatagggg agtggtcctg tattagctgt cacgtgagtg cttttgcgac   240
attttgcgac accacgtggc catttagggt atatatggcc gagtgagcga gcaggatctc   300
cattttgacc gcgaaatttg aacgagcagc agccatgccg ggcttctacg agatcgtgat   360
caaggtgccg agcgacctgg acgagcacct gccgggcatt tctgactcgt ttgtgagctg   420
ggtggccgag aaggaatggg agctgccccc ggattctgac atggatctga atctgattga   480
gcaggcaccc ctgaccgtgg ccgagaagct gcagcgcgac ttcctggtcc aatggcgccg   540
cgtgagtaag gccccggagg ccctcttctt tgttcagttc gagaagggcg agtcctactt   600
ccacctccat attctggtgg agaccacggg ggtcaaatcc atggtgctgg gccgcttcct   660
gagtcagatt agggacaagc tggtgcagac catctaccgc gggatcgagc cgaccctgcc   720
caactggttc gcggtgacca agacgcgtaa tggcgccgga ggggggaaca aggtggtgga   780
cgagtgctac atccccaact acctcctgcc caagactcag cccgagctgc agtgggcgtg   840
gactaacatg gaggagtata taagcgcctg tttgaacctg gccgagcgca acggctcgt   900 ggcgcagcac ctgacccacg tcagccgac ccaggagcag aacaaggaga atctgaaccc   960
caattctgac gcgcctgtca tccggtcaaa aacctccgcg cgctacatgg agctggtcgg  1020
gtggctggtg accggggca tcacctccga gaagcagtgg atccaggagg accaggcctc  1080
gtacatctcc ttcaacgccg cttccaactc gcggtcccag atcaaggccg ctctggacaa  1140
tgccggcaag atcatggcgc tgaccaaatc cgcgcccgac tacctggtag gccccgctcc  1200 gccccgcggac attaaaacca accgcatcta ccgcatcctg gagctgaacg gctacgaacc  1260
tgcctacgcc ggctccgtct ttctcggctg ggcccagaaa aggttcggga agcgcaacac  1320
catctggctg tttgggccgg ccaccacggg caagaccaac atcgcggaag ccatcgccca  1380
cgccgtgccc ttctacggct gcgtcaactg gaccaatgag aactttccct tcaatgattg  1440
```

```
cgtcgacaag atggtgatct ggtgggagga gggcaagatg acggccaagg tcgtggagtc   1500
cgccaaggcc attctcggcg gcagcaaggt gcgcgtggac caaaagtgca agtcgtccgc   1560
ccagatcgac cccaccccg tgatcgtcac ctccaacacc aacatgtgcg ccgtgattga   1620
cgggaacagc accaccttcg agcaccagca gccgttgcag gaccggatgt tcaaatttga   1680
actcacccgc cgtctggagc atgactttgg caaggtgaca aagcaggaag tcaaagagtt   1740
cttccgctgg gcgcaggatc acgtgaccga ggtggcgcat gagttctacg tcagaaaggg   1800
tggagccaac aaaagacccg cccccgatga cgcggataaa agcgagccca agcgggcctg   1860
cccctcagtc gcggatccat cgacgtcaga gcgggaagga gctccggtgg actttgccga   1920
caggtaccaa aacaaatgtt ctcgtcacgc gggcatgctt cagatgctgt ttccctgcaa   1980
gacatgcgag agaatgaatc agaatttcaa catttgcttc acgcacggga cgagagactg   2040
ttcagagtgc ttccccggcg tgtcagaatc tcaaccggtc gtcagaaaga ggacgtatcg   2100
gaaactctgt gccattcatc atctgctggg gcgggctccc gagattgctt gctcggcctg   2160
cgatctggtc aacgtggacc tggatgactg tgtttctgag caataaatga cttaaaccag   2220
gtatggctgc cgatggttat cttccagatt ggctcgagga caacctctct gagggcattc   2280
gcgagtggtg ggacttgaaa cctggagccc cgaagcccaa agccaaccag caaaagcagg   2340
acgacggccg gggtctggtg cttcctggct acaagtacct cggacccttc aacggactcg   2400
acaaggggga gcccgtcaac gcggcggacg cagcggccct cgagcacgac aaggcctacg   2460
accagcagct caaagcgggt gacaatccgt acctgcggta taaccacgcc gacgccgagt   2520
tcaggagctc tctgcaagaa gatacgtctt ttggggggcaa cctcgggcga gcagtcttcc   2580
aggccaagaa gcgggttctc gaacctctcg gtctggttga ggaaggcgct aagacggctc   2640
ctggaaagaa acgtccggta gagcagtcgc cacaagagcc agactcctcc tcgggcatcg   2700
gcaagacagg ccagcagccc gctaaaaaga gactcaattt tggtcagact ggcgactcag   2760
agtcagtccc cgatccacaa cctctcggag aacctccagc aaccccgct gctgtgggac   2820
ctactacaat ggcttcaggc ggtggcgcac caatggcaga caataacgaa ggcgccgacg   2880
gagtgggtaa tgcctcagga aattggcatt gcgattccac atggctgggc gacagagtca   2940
tcaccaccag cacccgcacc tgggccttgc ccacctacaa taaccacctc tacaagcaaa   3000
tctccagtgc ttcaacgggg gccagcaacg acaaccacta cttcggctac agcaccccct   3060
ggggggtattt tgatttcaac agattccact gccacttttc accacgtgac tggcagcgac   3120
tcatcaacaa caattgggga ttccggccca agagactcaa cttcaaactc ttcaacatcc   3180
aagtcaagga ggtcacgacg aatgatggcg tcacaaccat cgctaataac cttaccagca   3240
cggttcaagt cttctcggac tcggagtacc agcttccgta cgtcctcggc tctgcgcacc   3300
agggctgcct ccctccgttc ccggcggacg tgttcatgat tccgcaatac ggctacctga   3360
cgctcaacaa tggcagccaa gccgtgggac gttcatcctt ttactgcctg gaatatttcc   3420
cttctcagat gctgagaacg ggcaacaact ttaccttcag ctacacctt gaggaagtgc   3480
cttttccacag cagctacgcg cacagccaga gcctggaccg gctgatgaat cctctcatcg   3540
accaataccct gtattacctg aacagaactc aaaatcagtc cggaagtgcc caaacaagg   3600
acttgctgtt tagccgtggg tctccagctg gcatgtctgt tcagcccaaa aactggctac   3660
ctggaccctg ttatcggcag cagcgcgttt ctaaaacaaa aacagacaac aacaacagca   3720
attttacctg gactggtgct tcaaaatata acctcaatgg gcgtgaatcc atcatcaacc   3780
ctggcactgc tatggcctca cacaaagacg acgaagacaa gttctttccc atgagcggtg   3840
```

-continued

| | |
|---|---|
| tcatgatttt tggaaaagag agcgccggag cttcaaacac tgcattggac aatgtcatga | 3900 |
| ttacagacga agaggaaatt aaagccacta accctgtggc caccgaaaga tttgggaccg | 3960 |
| tggcagtcaa tttccagagc agcagcacag accctgcgac cggagatgtg catgctatgg | 4020 |
| gagcattacc tggcatggtg tggcaagata gagacgtgta cctgcagggt cccatttggg | 4080 |
| ccaaaattcc tcacacagat ggacactttc acccgtctcc tcttatgggc ggctttggac | 4140 |
| tcaagaaccc gcctcctcag atcctcatca aaaacacgcc tgttcctgcg aatcctccgg | 4200 |
| cggagttttc agctacaaag tttgcttcat tcatcaccca atactccaca ggacaagtga | 4260 |
| gtgtggaaat tgaatgggag ctgcagaaag aaaacagcaa gcgctggaat cccgaagtgc | 4320 |
| agtacacatc caattatgca aaatctgcca acgttgattt tactgtggac aacaatggac | 4380 |
| tttatactga gcctcgcccc attggcaccc gttaccttac ccgtcccctg taattacgtg | 4440 |
| ttaatcaata aaccggttga ttcgtttcag ttgaactttg gtctcctgtc cttcttatct | 4500 |
| tatcggttac catggttata gcttacacat taactgcttg gttgcgcttc gcgataaaag | 4560 |
| acttacgtca tcgggttacc cctagtgatg gagttgccca ctccctctct gcgcgctcgc | 4620 |
| tcgctcggtg gggcctgcgg accaaaggtc gcgagacggc agagctctgc tctgccggcc | 4680 |
| ccaccgagcg agcgagcgcg cagagaggga gtgggcaa | 4718 |

<210> SEQ ID NO 10
<211> LENGTH: 4679
<212> TYPE: DNA
<213> ORGANISM: Dependoparvovirus Adeno-associated virus - 2

<400> SEQUENCE: 10

| | |
|---|---|
| ttggccactc cctctctgcg cgctcgctcg ctcactgagg ccgggcgacc aaaggtcgcc | 60 |
| cgacgcccgg gctttgcccg gcggcctcag tgagcgagc gagcgcgcag agagggagtg | 120 |
| gccaactcca tcactagggg ttcctggagg ggtggagtcg tgacgtgaat tacgtcatag | 180 |
| ggttagggag gtcctgtatt agaggtcacg tgagtgtttt gcgacatttt gcgacaccat | 240 |
| gtggtcacgc tgggtattta gcccgagtg agcacgcagg gtctccattt tgaagcggga | 300 |
| ggtttgaacg cgcagccgcc atgccggggt tttacgagat tgtgattaag gtccccagcg | 360 |
| accttgacga catctgcccc ggcatttctg acagctttgt gaactgggtg gccgagaagg | 420 |
| aatgggagtt gccgccagat tctgacatgg atctgaatct gattgagcag gcaccctga | 480 |
| ccgtggccga aagctgcag cgcgactttc tgacggaatg cgccgtgtg agtaaggccc | 540 |
| cggaggccct tttctttgtg caatttgaga agggagagag ctacttccac atgcacgtgc | 600 |
| tcgtggaaac caccggggtg aaatccatgg ttttgggacg tttcctgagt cagattcgcg | 660 |
| aaaaactgat tcagagaatt taccgcggga tcgagccgac tttgccaaac tggttcgcgg | 720 |
| tcacaaagac cagaaatggc gccggaggcg ggaacaaggt ggtggatgag tgctacatcc | 780 |
| ccaattactt gctccccaaa acccagcctg agctccagtg ggcgtggact aatatggaac | 840 |
| agtatttaag cgcctgtttg aatctcacgg agcgtaaacg gttggtggcg cagcatctga | 900 |
| cgcacgtgtc gcagacgcag gagcagaaca aagagaatca gaatcccaat ctgatgcgc | 960 |
| cggtgatcag atcaaaaact tcagccaggt acatggagct ggtcgggtgg ctcgtggaca | 1020 |
| aggggattac ctcggagaag cagtggatcc aggaggacca ggcctcatac atctccttca | 1080 |
| atgcggcctc caactcgcgg tcccaaatca aggctgcctt ggacaatgcg ggaaagatta | 1140 |
| tgagcctgac taaaaccgcc cccgactacc tggtgggcca gcagcccgtg gaggacattt | 1200 |

```
ccagcaatcg gatttataaa attttggaac taaacgggta cgatccccaa tatgcggctt    1260
ccgtctttct gggatgggcc acgaaaaagt tcggcaagag gaacaccatc tggctgtttg    1320
ggcctgcaac taccgggaag accaacatcg cggaggccat agcccacact gtgcccttct    1380
acgggtgcgt aaactggacc aatgagaact ttcccttcaa cgactgtgtc gacaagatgg    1440
tgatctggtg ggaggagggg aagatgaccg ccaaggtcgt ggagtcggcc aaagccattc    1500
tcggaggaag caaggtgcgc gtggaccaga aatgcaagtc ctcggcccag atagacccga    1560
ctcccgtgat cgtcacctcc aacaccaaca tgtgcgccgt gattgacggg aactcaacga    1620
ccttcgaaca ccagcagccg ttgcaagacc ggatgttcaa atttgaactc acccgccgtc    1680
tggatcatga ctttgggaag gtcaccaagc aggaagtcaa agacttttc cggtgggcaa     1740 aggatcacgt ggttgaggtg gagcatgaat tctacgtcaa aaagggtgga gccaagaaaa    1800
gacccgcccc cagtgacgca gatataagtg agcccaaacg ggtgcgcgag tcagttgcgc    1860
agccatcgac gtcagacgcg gaagcttcga tcaactacgc agacaggtac caaaacaaat    1920
gttctcgtca cgtgggcatg aatctgatgc tgtttccctg cagacaatgc gagagaatga    1980
atcagaattc aaatatctgc ttcactcacg gacagaaaga ctgtttagag tgctttcccg    2040
tgtcagaatc tcaacccgtt tctgtcgtca aaaaggcgta tcagaaactg tgctacattc    2100
atcatatcat gggaaaggtg ccagacgctt gcactgcctg cgatctggtc aatgtggatt    2160
tggatgactg catctttgaa caataaatga tttaaatcag gtatgctgc cgatggttat     2220 cttccagatt ggctcgagga cactctctct gaaggaataa gacagtggtg gaagctcaaa    2280
cctggcccac caccaccaaa gcccgcgagag cggcataagg acgacagcag gggtcttgtg   2340
cttcctgggt acaagtacct cggacccttc aacggactcg acaagggaga gccggtcaac    2400
gaggcagacg ccgcggccct cgagcacgac aaagcctacg accggcagct cgacagcgga    2460
gacaacccgt acctcaagta caaccacgcc gacgcggagt ttcaggagcg ccttaaagaa    2520
gatacgtctt ttgggggcaa cctcggacga gcagtcttcc aggcgaaaaa gagggttctt    2580
gaacctctgg gcctggttga ggaacctgtt aagacggctc cgggaaaaaa gaggccggta    2640
gagcactctc ctgtggagcc agactcctcc tcgggaaccg gaaaggcggg ccagcagcct    2700
gcaagaaaaa gattgaattt tggtcagact ggagacgcag actcagtacc tgaccccag    2760 cctctcggac agccaccagc agccccctct ggtctgggaa ctaatacgat ggctacaggc    2820
agtggcgcac caatggcaga caataacgag ggcgccgacg gagtgggtaa ttcctcggga   2880
aattggcatt gcgattccac atggatgggc gacagagtca tcaccaccag cacccgaacc    2940
tgggccctgc ccacctacaa caaccacctc tacaaacaaa tttccagcca atcaggagcc    3000
tcgaacgaca atcactactt tggctacagc accccttggg ggtattttga cttcaacaga    3060
ttccactgcc acttttcacc acgtgactgg caaagactca tcaacaacaa ctgggggattc    3120 cgacccaaga gactcaactt caagctcttt aacattcaag tcaaagaggt cacgcagaat    3180
gacggtacga cgacgattgc caataacctt accagcacgg ttcaggtgtt tactgactcg    3240
gagtaccagc tcccgtacgt cctcggctcg gcgcatcaag gatgcctccc gccgttccca    3300
gcagacgtct tcatggtgcc acagtatgga tacctcaccc tgaacaacgg gagtcaggca    3360
gtaggacgct cttcatttta ctgcctggag tactttcctt ctcagatgct gcgtaccgga    3420
aacaacttta ccttcagcta cacttttgag gacgttcctt tccacagcag ctacgctcac    3480
agccagagtc tggaccgtct catgaatcct ctcatcgacc agtacctgta ttacttgagc    3540
agaacaaaca ctccaagtgg aaccaccacg cagtcaaggc ttcagttttc tcaggccgga    3600
```

```
gcgagtgaca ttcgggacca gtctaggaac tggcttcctg gaccctgtta ccgccagcag    3660
cgagtatcaa agacatctgc ggataacaac aacagtgaat actcgtggac tggagctacc    3720
aagtaccacc tcaatggcag agactctctg gtgaatccgg gcccggccat ggcaagccac    3780
aaggacgatg aagaaaagtt ttttcctcag agcggggttc tcatctttgg gaagcaaggc    3840
tcagagaaaa caaatgtgga cattgaaaag gtcatgatta cagacgaaga ggaaatcagg    3900
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcaggggccc atctgggcaa agattccaca cacggacgga    4080 catttcacc cctctcccct catgggtgga ttcggactta acaccctcc tccacagatt    4140 ctcatcaaga caccccggt acctgcgaat ccttcgacca ccttcagtgc ggcaaagttt    4200
gcttccttca tcacacagta ctccacggga caggtcagcg tggagatcga gtgggagctg    4260
cagaaggaaa acagcaaacg ctggaatccc gaaattcagt acacttccaa ctacaacaag    4320
tctgttaatg tggactttac tgtggacact aatggcgtgt attcagagcc tcgccccatt    4380
ggcaccagat acctgactcg taatctgtaa ttgcttgtta atcaataaac cgtttaattc    4440
gtttcagttg aactttggtc tctgcgtatt tctttcttat ctagtttcca tggctacgta    4500
gataagtagc atggcgggtt aatcattaac tacaaggaac ccctagtgat ggagttggcc    4560
actccctctc tgcgcgctcg ctcgctcact gaggccgggc gaccaaaggt cgcccgacgc    4620
ccgggctttg cccgggcggc ctcagtgagc gagcgagcgc gcagagaggg agtggccaa     4679
```

<210> SEQ ID NO 11
<211> LENGTH: 4722
<212> TYPE: DNA
<213> ORGANISM: Dependoparvovirus Adeno-associated virus - 3

<400> SEQUENCE: 11

```
tggccactcc ctctatgcgc actcgctcgc tcggtggggc ctggcgacca aggtcgccaa      60
gacggacgtg ctttgcacgt ccggccccac cgagcgagcg agtgcgcata gagggagtgg     120
ccaactccat cactagaggt atggcagtga cgtaacgcga agcgcgcgaa gcgagaccac     180
gcctaccagc tgcgtcagca gtcaggtgac ccttttgcga cagtttgcga caccacgtgg     240
ccgctgaggg tatatattct cgagtgagcg aaccaggagc tccattttga ccgcgaaatt     300
tgaacgagca gcagccatgc cggggttcta cgagattgtc ctgaaggtcc gagtgacct     360 ggacgagcac ctgccgggca tttctaactc gtttgttaac tgggtggccg agaaggaatg     420
ggagctgccg ccggattctg acatggatcc gaatctgatt gagcaggcac ccctgaccgt     480
ggccgaaaag cttcagcgcg agttcctggt ggagtggcgc cgcgtgagta aggcccggga     540
ggccctcttt tttgtccagt tcgaaaaggg ggagacctac ttccacctgc acgtgctgat     600
tgagaccatc ggggtcaaat ccatggtggt cggccgctac gtgagccaga ttaaagagaa     660
gctggtgacc cgcatctacc gcggggtcga gccgcagctt ccgaactggt tcgcggtgac     720
caaaacgcga aatggcgccg ggggcgggaa caaggtggtg gacgactgct acatccccaa     780
ctacctgctc cccaagaccc agcccgagct ccagtgggcg tggactaaca tggaccagta     840
tttaagcgcc tgtttgaatc tcgcggagcg taaacggctg gtggcgcagc atctgacgca     900
cgtgtcgcag acgcaggagc agaacaaaga gaatcagaac cccaattctg acgcgccggt     960
catcaggtca aaaacctcag ccaggtacat ggagctggtc gggtggctgg tggaccgcgg    1020
```

```
gatcacgtca gaaaagcaat ggattcagga ggaccaggcc tcgtacatct ccttcaacgc    1080
cgcctccaac tcgcggtccc agatcaaggc cgcgctggac aatgcctcca agatcatgag    1140
cctgacaaag acggctccgg actacctggt gggcagcaac ccgccggagg acattaccaa    1200
aaatcggatc taccaaatcc tggagctgaa cgggtacgat ccgcagtacg cggcctccgt    1260
cttcctgggc tgggcgcaaa agaagttcgg gaagaggaac accatctggc tctttgggcc    1320
ggccacgacg gtaaaaacca acatcgcgga agccatcgcc cacgccgtgc ccttctacgg    1380
ctgcgtaaac tggaccaatg agaactttcc cttcaacgat tgcgtcgaca agatggtgat    1440
ctggtgggag gagggcaaga tgacggccaa ggtcgtggag agcgccaagg ccattctggg    1500
cggaagcaag gtgcgcgtgg accaaaagtg caagtcatcg gcccagatcg aacccactcc    1560
cgtgatcgtc acctccaaca ccaacatgtg cgccgtgatt gacgggaaca gcaccacctt    1620
cgagcatcag cagccgctgc aggaccggat gtttaaattt gaacttaccc gccgtttgga    1680
ccatgacttt gggaaggtca ccaaacagga agtaaaggac tttttccggt gggcttccga    1740
tcacgtgact gacgtggctc atgagttcta cgtcagaaag ggtggagcta agaaacgccc    1800
cgcctccaat gacgcggatg taagcgagcc aaaacggcag tgcacgtcac ttgcgcagcc    1860
gacaacgtca gacgcggaag caccggcgga ctacgcggac aggtaccaaa acaaatgttc    1920
tcgtcacgtg ggcatgaatc tgatgctttt ccctgtaaaa acatgcgaga gaatgaatca    1980
aatttccaat gtctgtttta cgcatggtca aagagactgt ggggaatgct tccctggaat    2040
gtcagaatct caacccgttt ctgtcgtcaa aagaagact tatcagaaac tgtgtccaat    2100
tcatcatatc ctgggaaggg cacccgagat tgcctgttcg gcctgcgatt tggccaatgt    2160
ggacttggat gactgtgttt ctgagcaata aatgacttaa accaggtatg gctgctgacg    2220
gttatcttcc agattggctc gaggacaacc tttctgaagg cattcgtgag tggtgggctc    2280
tgaaacctgg agtccctcaa cccaaagcga accaacaaca ccaggacaac cgtcggggtc    2340
ttgtgcttcc gggttacaaa tacctcggac ccggtaacgg actcgacaaa ggagagccgg    2400
tcaacgaggc ggacgcggca gccctcgaac acgacaaagc ttacgaccag cagctcaagg    2460
ccggtgacaa cccgtacctc aagtacaacc acgccgacgc cgagtttcag gagcgtcttc    2520
aagaagatac gtcttttggg ggcaaccttg gcagagcagt cttccaggcc aaaaagagga    2580
tccttgagcc tcttggtctg gttgaggaag cagctaaaac ggctcctgga agaagaggc    2640 ctgtagatca gtctcctcag gaaccggact catcatctgg tgttggcaaa tcgggcaaac    2700
agcctgccag aaaaagacta aatttcggtc agactggcga ctcagagtca gtcccagacc    2760
ctcaacctct cggagaacca ccagcagccc ccacaagttt gggatctaat acaatggctt    2820
caggcggtgg cgcaccaatg gcagacaata acgagggtgc cgatggagtg ggtaattcct    2880
caggaaattg gcattgcgat tcccaatggc tgggcgacag agtcatcacc accagcacca    2940
gaacctgggc cctgcccact acaacaacc atctctacaa gcaaatctcc agccaatcag    3000
gagcttcaaa cgacaaccac tactttggct acagcacccc ttgggggtat tttgacttta    3060
acagattcca ctgccacttc tcaccacgtg actggcagcg actcattaac aacaactggg    3120
gattccggcc caagaaactc agcttcaagc tcttcaacat ccaagttaaa gaggtcacgc    3180
agaacgatgg cacgacgact attgccaata accttaccag cacggttcaa gtgtttacgg    3240
actcggagta tcagctcccg tacgtgctcg ggtcggcgca ccaaggctgt ctcccgccgt    3300
ttccagcgga cgtcttcatg gtccctcagt atggatacct cacctgaac aacgaagtc     3360 aagcggtggg acgctcatcc tttactgcc tggagtactt cccttcgcag atgctaagga    3420
```

```
ctggaaataa cttccaattc agctatacct tcgaggatgt accttttcac agcagctacg    3480
ctcacagcca gagtttggat cgcttgatga atcctcttat tgatcagtat ctgtactacc    3540
tgaacagaac gcaaggaaca acctctggaa caaccaacca atcacggctg ctttttagcc    3600
aggctgggcc tcagtctatg tctttgcagg ccagaaattg gctacctggg ccctgctacc    3660
ggcaacagag actttcaaag actgctaacg acaacaacaa cagtaacttt ccttggacag    3720
cggccagcaa atatcatctc aatggccgcg actcgctggt gaatccagga ccagctatgg    3780
ccagtcacaa ggacgatgaa gaaaaatttt tccctatgca cggcaatcta atatttggca    3840
aagaagggac aacggcaagt aacgcagaat tagataatgt aatgattacg gatgaagaag    3900
agattcgtac caccaatcct gtggcaacag agcagtatgg aactgtggca ataaacttgc    3960
agagctcaaa tacagctccc acgactagaa ctgtcaatga tcagggggcc ttacctggca    4020
tggtgtggca agatcgtgac gtgtaccttc aaggacctat ctgggcaaag attcctcaca    4080
cggatggaca ctttcatcct tctcctctga tgggaggctt tggactgaaa catccgcctc    4140
ctcaaatcat gatcaaaaat actccggtac cggcaaatcc tccgacgact ttcagcccgg    4200
ccaagtttgc ttcatttatc actcagtact ccactggaca ggtcagcgtg gaaattgagt    4260
gggagctaca gaaagaaaac agcaaacgtt ggaatccaga gattcagtac acttccaact    4320
acaacaagtc tgttaatgtg gactttactg tagacactaa tggtgtttat agtgaacctc    4380
gcccctattg gaacccggta tctcacacga aacttgtaat ctggttaatc aataaaccgt    4440
ttaattcgtt tcagttgaac tttggctctt gtgcacttct tatcttatct tgtttccatg    4500
gctactgcgt agataagcag cggcctgcgg cgcttgcgct tcgcggttta caactgctgg    4560
ttaatattta actctcgcca tacctctagt gatggagttg gccactccct ctatgcgcac    4620
tcgctcgctc ggtggggccg gacgtgcaaa gcacgtccgt ctggcgacct ttggtcgcca    4680
ggccccaccg agcgagcgag tgcgcataga gggagtggcc aa                      4722
```

<210> SEQ ID NO 12
<211> LENGTH: 4767
<212> TYPE: DNA
<213> ORGANISM: Dependoparvovirus Adeno-associated virus - 4

<400> SEQUENCE: 12

```
ttggccactc cctctatgcg cgctcgctca ctcactcggc cctggagacc aaaggtctcc      60
agactgccgg cctctggccg gcagggccga gtgagtgagc gagcgcgcat agagggagtg     120
gccaactcca tcatctaggt ttgcccactg acgtcaatgt gacgtcctag ggttagggag     180
gtccctgtat tagcagtcac gtgagtgtcg tatttcgcgg agcgtagcgg agcgcatacc     240
aagctgccac gtcacagcca cgtggtccgt ttgcgacagt ttgcgacacc atgtggtcag     300
gagggtatat aaccgcgagt gagccagcga ggagctccat tttgcccgcg aattttgaac     360
gagcagcagc catgccgggg ttctacgaga tcgtgctgaa ggtgcccagc gacctggacg     420
agcacctgcc cggcatttct gactcttttg tgagctgggt ggccgagaag gaatgggagc     480
tgccgccgga ttctgacatg gacttgaatc tgattgagca ggcacccctg accgtggccg     540
aaaagctgca acgcgagttc ctggtcgagt ggcgccgcgt gagtaaggcc ccggaggccc     600
tcttctttgt ccagttcgag aagggggaca gctacttcca cctgcacatc ctggtggaga     660
ccgtgggcgt caaatccatg gtggtgggcc gctacgtgag ccagattaaa gagaagctgg     720
tgacccgcat ctaccgcggg gtcgagccgc agcttccgaa ctggttcgcg gtgaccaaga     780
```

```
cgcgtaatgg cgccggaggc gggaacaagg tggtggacga ctgctacatc cccaactacc    840
tgctccccaa gacccagccc gagctccagt gggcgtggac taacatggac cagtatataa    900
gcgcctgttt gaatctcgcg gagcgtaaac ggctggtggc gcagcatctg acgcacgtgt    960
cgcagacgca ggagcagaac aaggaaaacc agaaccccaa ttctgacgcg ccggtcatca   1020
ggtcaaaaac ctccgccagg tacatggagc tggtcgggtg gctggtggac cgcgggatca   1080
cgtcagaaaa gcaatggatc caggaggacc aggcgtccta catctccttc aacgccgcct   1140
ccaactcgcg gtcacaaatc aaggccgcgc tggacaatgc ctccaaaatc atgagcctga   1200
caaagacggc tccggactac ctggtgggcc agaacccgcc ggaggacatt ccagcaacc    1260 gcatctaccg aatcctcgag atgaacgggt acgatccgca gtacgcggcc tccgtcttcc   1320
tgggctgggc gcaaaagaag ttcgggaaga ggaacaccat ctggctcttt ggccggcca    1380 cgacgggtaa aaccaacatc gcggaagcca tcgcccacgc cgtgcccttc tacggctgcg   1440
tgaactggac caatgagaac tttccgttca acgattgcgt cgacaagatg gtgatctggt   1500
gggaggaggg caagatgacg gccaaggtcg tagagagcgc caaggccatc ctgggcggaa   1560
gcaaggtgcg cgtggaccaa aagtgcaagt catcggccca gatcgaccca actcccgtga   1620
tcgtcacctc caacaccaac atgtgcgcgg tcatcgacgg aaactcgacc accttcgagc   1680
accaacaacc actccaggac cggatgttca agttcgagct caccaagcgc ctggagcacg   1740
actttggcaa ggtcaccaag caggaagtca agactttttt ccgtgggcg tcagatcacg   1800 tgaccgaggt gactcacgag ttttacgtca gaaagggtgg agctagaaag aggcccgccc   1860
ccaatgacgc agatataagt gagcccaagc gggcctgtcc gtcagttgcg cagccatcga   1920
cgtcagacgc ggaagctccg gtggactacg cggacaggta ccaaaacaaa tgttctcgtc   1980
acgtgggtat gaatctgatg cttttccct gccggcaatg cgagagaatg aatcagaatg   2040
tggacatttg cttcacgcac ggggtcatgg actgtgccga gtgcttcccc gtgtcagaat   2100
ctcaacccgt gtctgtcgtc agaaagcgga cgtatcagaa actgtgtccg attcatcaca   2160
tcatggggag ggcgcccgag gtggcctgct cggcctgcga actggccaat gtggacttgg   2220
atgactgtga catggaacaa taaatgactc aaaccagata tgactgacgg ttaccttcca   2280
gattggctag aggacaacct ctctgaaggc gttcgagagt ggtgggcgct gcaacctgga   2340
gcccctaaac ccaaggcaaa tcaacaacat caggacaacg ctcggggtct tgtgcttccg   2400
ggttacaaat acctcggacc cggcaacgga ctcgacaagg gggaacccgt caacgcagcg   2460
gacgcggcag ccctcgagca cgacaaggcc tacgaccagc agctcaaggc cggtgacaac   2520
ccctacctca gtacaaccca cgccgacgcg gagttccagc agcggcttca gggcgacaca   2580
tcgtttgggg gcaacctcgg cagagcagtc ttccaggcca aaagagggt tcttgaacct   2640 cttggtctgg ttgagcaagc gggtgagacg gctcctggaa agaagagacc gttgattgaa   2700 tcccccagc agcccgactc ctccacgggg atcggcaaaa aggcaagca gccggctaaa   2760 aagaagctcg ttttcgaaga cgaaactgga gcaggcgacg gaccccctga gggatcaact   2820
tccggagcca tgtctgatga cagtgagatg cgtgcagcag ctggcggagc tgcagtcgag   2880
ggcggacaag gtgccgatgg agtgggtaat gcctcgggtg attggcattg cgattccacc   2940
tggtctgagg gccacgtcac gaccaccagc accagaacct gggtcttgcc cacctacaac   3000
aaccacctct acaagcgact cggagagagc ctgcagtcca acacctacaa cggattctcc   3060
accccctggg gatactttga cttcaaccgc ttccactgcc acttctcacc acgtgactgg   3120
cagcgactca tcaacaacaa ctgggggcatg cgacccaaag ccatgcgggt caaaatcttc   3180
```

```
aacatccagg tcaaggaggt cacgacgtcg aacggcgaga caacggtggc taataacctt    3240
accagcacgg ttcagatctt tgcggactcg tcgtacgaac tgccgtacgt gatggatgcg    3300
ggtcaagagg gcagcctgcc tccttttccc aacgacgtct ttatggtgcc ccagtacggc    3360
tactgtggac tggtgaccgg caacacttcg cagcaacaga ctgacagaaa tgccttctac    3420
tgcctggagt actttccttc gcagatgctg cggactggca acaactttga aattacgtac    3480
agttttgaga aggtgccttt ccactcgatg tacgcgcaca gccagagcct ggaccggctg    3540
atgaaccctc tcatcgacca gtacctgtgg ggactgcaat cgaccaccac cggaaccacc    3600
ctgaatgccg ggactgccac caccaacttt accaagctgc ggcctaccaa cttttccaac    3660
tttaaaaaga actggctgcc cgggccttca atcaagcagc agggcttctc aaagactgcc    3720
aatcaaaact acaagatccc tgccaccggg tcagacagtc tcatcaaata cgagacgcac    3780
agcactctgg acggaagatg gagtgccctg acccccggac ctccaatggc cacggctgga    3840
cctgcggaca gcaagttcag caacagccag ctcatctttg cggggcctaa acagaacggc    3900
aacacggcca ccgtacccgg gactctgatc ttcacctctg aggaggagct ggcagccacc    3960
aacgccaccg atacggacat gtggggcaac ctacctggcg tgaccagag caacagcaac    4020 ctgccgaccg tggacagact gacagccttg ggagccgtgc ctggaatggt ctggcaaaac    4080
agagacattt actaccaggg tcccatttgg gccaagattc tcataccga tggacacttt    4140 cacccctcac cgctgattgg tgggtttggg ctgaaacacc cgcctcctca aattttatc    4200 aagaacaccc cggtacctgc gaatcctgca acgaccttca gctctactcc ggtaaactcc    4260
ttcattactc agtacagcac tggccaggtg tcggtgcaga ttgactggga gatccagaag    4320
gagcggtcca aacgctggaa ccccgaggtc cagtttacct ccaactacgg acagcaaaac    4380
tctctgttgt gggctcccga tgcggctggg aaatacactg agcctaggc tatcggtacc    4440 cgctacctca cccaccacct gtaataacct gttaatcaat aaaccggttt attcgtttca    4500
gttgaacttt ggtctccgtg tccttcttat cttatctcgt ttccatggct actgcgtaca    4560
taagcagcgg cctgcggcgc ttgcgcttcg cggtttacaa ctgccggtta atcagtaact    4620
tctggcaaac cagatgatgg agttggccac attagctatg cgcgctcgct cactcactcg    4680
gccctggaga ccaaaggtct ccagactgcc ggcctctggc cggcagggcc gagtgagtga    4740
gcgagcgcgc atagagggag tggccaa                                       4767
```

<210> SEQ ID NO 13
<211> LENGTH: 4642
<212> TYPE: DNA
<213> ORGANISM: Dependoparvovirus Adeno-associated virus - 5

<400> SEQUENCE: 13

```
ctctccccc tgtcgcgttc gctcgctcgc tggctcgttt gggggggtgg cagctcaaag      60
agctgccaga cgacggccct ctggccgtcg ccccccaaa cgagccagcg agcgagcgaa     120
cgcgacaggg gggagagtgc cacactctca agcaagggg ttttgtaagc agtgatgtca     180
taatgatgta atgcttattg tcacgcgata gttaatgatt aacagtcatg tgatgtgttt     240
tatccaatag gaagaaagcg cgcgtatgag ttctcgcgag acttccgggg tataaaagac     300
cgagtgaacg agcccgccgc cattctttgc tctggactgc tagaggaccc tcgctgccat     360
ggctaccttc tatgaagtca ttgttcgcgt cccatttgac gtggaggaac atctgcctgg     420
aatttctgac agctttgtgg actgggtaac tggtcaaatt tgggagctgc ctccagagtc     480
```

```
agatttaaat ttgactctgg ttgaacagcc tcagttgacg gtggctgata gaattcgccg    540
cgtgttcctg tacgagtgga acaaattttc caagcaggag tccaaattct ttgtgcagtt    600
tgaaaaggga tctgaatatt ttcatctgca cacgcttgtg gagacctccg gcatctcttc    660
catggtcctc ggccgctacg tgagtcagat tcgcgcccag ctggtgaaag tggtcttcca    720
gggaattgaa ccccagatca acgactgggt cgccatcacc aaggtaaaga agggcggagc    780
caataaggtg gtggattctg gtatattcc cgcctacctg ctgccgaagg tccaaccgga     840
gcttcagtgg gcgtggacaa acctggacga gtataaattg gccgccctga atctggagga    900
gcgcaaacgg ctcgtcgcgc agtttctggc agaatcctcg cagcgctcgc aggaggcggc    960
ttcgcagcgt gagttctcgg ctgacccggt catcaaaagc aagacttccc agaaatacat   1020
ggcgctcgtc aactggctcg tggagcacgg catcacttcc gagaagcagt ggatccagga   1080
aaatcaggag agctacctct ccttcaactc caccggcaac tctcggagcc agatcaaggc   1140
cgcgctcgac aacgcgacca aaattatgag tctgacaaaa agcgcggtgg actacctcgt   1200
ggggagctcc gttcccgagg acatttcaaa aaacagaatc tggcaaattt ttgagatgaa   1260
tggctacgac ccggcctacg cgggatccat cctctacggc tggtgtcagc gctccttcaa   1320
caagaggaac accgtctggc tctacggacc cgccacgacc ggcaagacca acatcgcgga   1380
ggccatcgcc cacactgtgc ccttttacgg ctgcgtgaac tggaccaatg aaaactttcc   1440
ctttaatgac tgtgtggaca aaatgctcat ttggtgggag gagggaaaga tgaccaacaa   1500
ggtggttgaa tccgccaagg ccatcctggg gggctcaaag gtgcgggtcg atcagaaatg   1560
taaatcctct gttcaaattg attctacccc tgtcattgta acttccaata caaacatgtg   1620
tgtggtggtg gatgggaatt ccacgacctt tgaacaccag cagccgctgg aggaccgcat   1680
gttcaaattt gaactgacta gcggctcccg ccagattttt ggcaagatta ctaagcagga   1740
agtcaaggac ttttttgctt gggcaaaggt caatcaggtg ccggtgactc acgagtttaa   1800
agttcccagg gaattggcgg gaactaaagg ggcggagaaa tctctaaaac gcccactggg   1860
tgacgtcacc aatactagct ataaaagtct ggagaagcgg gccaggctct catttgttcc   1920
cgagacgcct cgcagttcag acgtgactgt tgatcccgct cctctgcgac cgctcaattg   1980
gaattcaagg tatgattgca aatgtgacta tcatgctcaa tttgacaaca tttctaacaa   2040
atgtgatgaa tgtgaatatt tgaatcgggg caaaaatgga tgtatctgtc acaatgtaac   2100
tcactgtcaa atttgtcatg ggattccccc ctgggaaaag gaaaacttgt cagattttgg   2160
ggattttgac gatgccaata agaacagta aataaagcga gtagtcatgt cttttgttga    2220
tcaccctcca gattggttgg aagaagttgg tgaaggtctt cgcgagtttt tgggccttga   2280
agcgggccca ccgaaaccaa acccaatca gcagcatcaa gatcaagccc gtggtcttgt    2340
gctgcctggt tataactatc tcggacccgg aaacggtctc gatcgaggag agcctgtcaa   2400
cagggcagac gaggtcgcgc gagagcacga catctcgtac aacgagcagc ttgaggcggg   2460
agacaacccc tacctcaagt acaaccacgc ggacgccgag tttcaggaga agctcgccga   2520
cgacacatcc ttcgggggaa acctcggaaa ggcagtcttt caggccaaga aaagggttct   2580 cgaaccttt ggcctggttg aagagggtgc taagacggcc cctaccggaa agcggataga    2640
cgaccacttt ccaaaaagaa agaaggctcg gaccgaagag gactccaagc cttccacctc   2700
gtcagacgcc gaagctggac ccagcggatc ccagcagctg caaatcccag cccaaccagc   2760
ctcaagtttg ggagctgata caatgtctgc ggggaggtggc ggcccattgg gcgacaataa   2820
ccaaggtgcc gatggagtgg gcaatgcctc gggagattgg cattgcgatt ccacgtggat   2880
```

```
gggggacaga gtcgtcacca agtccacccg aacctgggtg ctgcccagct acaacaacca    2940
ccagtaccga gagatcaaaa gcggctccgt cgacggaagc aacgccaacg cctactttgg    3000
atacagcacc ccctgggggt actttgactt taaccgcttc cacagccact ggagccccg     3060
agactggcaa agactcatca acaactactg gggcttcaga ccccggtccc tcagagtcaa    3120
aatcttcaac attcaagtca aagaggtcac ggtgcaggac tccaccacca ccatcgccaa    3180
caacctcacc tccaccgtcc aagtgtttac ggacgacgac taccagctgc cctacgtcgt    3240
cggcaacggg accgagggat gcctgccggc cttccctccg caggtcttta cgctgccgca    3300
gtacggttac cgcgacgctga accgcgacaa cacagaaaat cccaccgaga ggagcagctt    3360
cttctgccta gagtactttc ccagcaagat gctgagaacg ggcaacaact ttgagtttac    3420
ctacaacttt gaggaggtgc ccttccactc cagcttcgct cccagtcaga acctgttcaa    3480
gctggccaac ccgctggtgg accagtactt gtaccgcttc gtgagcacaa ataacactgg    3540
cggagtccag ttcaacaaga acctggccgg agatacgcc aacacctaca aaaactggtt     3600
cccggggccc atgggccgaa cccagggctg gaacctgggc tccggggtca ccgcgccag     3660
tgtcagcgcc ttcgccacga ccaataggat ggagctcgag ggcgcgagtt accaggtgcc    3720
cccgcagccg aacggcatga ccaacaacct ccagggcagc aacacctatg ccctggagaa    3780
cactatgatc ttcaacagcc agccggcgaa cccgggcacc accgcacgt acctcgaggg    3840
caacatgctc atcaccagcg agagcgagac gcagccggtg aaccgcgtgg cgtacaacgt    3900
cggcgggcag atggccacca caaccgagc tccaccact gccccgcga ccggcacgta      3960
caacctccag gaaatcgtgc ccggcagcgt gtggatggag agggacgtgt acctccaagg    4020
acccatctgg gccaagatcc cagagacggg ggcgcacttt caccctctc cggccatggg    4080
cggattcgga ctcaaacacc caccgccat gatgctcatc aagaacacgc ctgtgcccgg    4140
aaatatcacc agcttctcgg acgtgcccgt cagcagcttc atcacccagt acagcaccgg    4200
gcaggtcacc gtggagatgg agtgggagct caagaaggaa actccaaga ggtggaaccc    4260
agagatccag tacacaaaca actacaacga cccccagtttt gtggactttg ccccggacag    4320
caccggggaa tacagaacca ccagacctat cggaaccccga taccttaccc gacccctta    4380
acccattcat gtcgcatacc ctcaataaac cgtgtattcg tgtcagtaaa atactgcctc    4440
ttgtggtcat tcaatgaata acagcttaca acatctacaa aacctccttg cttgagagtg    4500
tggcactctc cccctgtcg cgttcgctcg ctcgctggct cgtttggggg ggtggcagct    4560
caaagagctg ccagacgacg gccctctggc cgtcgccccc caaacgagc cagcgagcga    4620
gcgaacgcga caggggggag ag                                             4642

<210> SEQ ID NO 14
<211> LENGTH: 4683
<212> TYPE: DNA
<213> ORGANISM: Dependoparvovirus Adeno-associated virus - 6

<400> SEQUENCE: 14
ttggccactc cctctctgcg cgctcgctcg ctcactgagg ccgggcgacc aaaggtcgcc      60
cgacgcccgg gctttgcccg gcggcctca gtgagcgagc gagcgcgcag agaggagtg     120
gccaactcca tcactagggg ttcctggagg ggtggagtcg tgacgtgaat tacgtcatag    180
ggttagggag gtcctgtatt agaggtcacg tgagtgtttt gcgacatttt gcgacaccat    240
gtggtcacgc tgggtattta agcccgagtg agcacgcagg gtctccattt tgaagcggga    300
```

-continued

```
ggtttgaacg cgcagcgcca tgccggggtt ttacgagatt gtgattaagg tccccagcga    360
ccttgacgag catctgcccg gcatttctga cagctttgtg aactgggtgg ccgagaagga    420
atgggagttg ccgccagatt ctgacatgga tctgaatctg attgagcagg cacccctgac    480
cgtggccgag aagctgcagc gcgacttcct ggtccagtgg cgccgcgtga gtaaggcccc    540
ggaggccctc ttctttgttc agttcgagaa gggcgagtcc tacttccacc tccatattct    600
ggtggagacc acgggggtca atccatggt gctgggccgc ttcctgagtc agattaggga    660
caagctggtg cagaccatct accgcgggat cgagccgacc ctgcccaact ggttcgcggt    720
gaccaagacg cgtaatggcg ccggagggg gaacaaggtg gtggacgagt gctacatccc    780
caactacctc ctgcccaaga ctcagcccga gctgcagtgg gcgtggacta acatggagga    840
gtatataagc gcgtgtttaa acctggccga gcgcaaacgg ctcgtggcgc acgacctgac    900
ccacgtcagc cagacccagg agcagaacaa ggagaatctg aaccccaatt ctgacgcgcc    960
tgtcatccgg tcaaaaacct ccgcacgcta catggagctg gtcgggtggc tggtggaccg   1020
gggcatcacc tccgagaagc agtggatcca ggaggaccag gcctcgtaca tctccttcaa   1080
cgccgcctcc aactcgcggt cccagatcaa ggccgctctg acaatgccg gcaagatcat   1140 ggcgctgacc aaatccgcgc ccgactacct ggtaggcccc gctccgcccg ccgacattaa   1200
aaccaaccgc atttaccgca tcctggagct gaacggctac gaccctgcct acgccggctc   1260
cgtctttctc ggctgggccc agaaaaggtt cggaaaacgc aacaccatct ggctgtttgg   1320
gccggccacc acgggcaaga ccaacatcgc ggaagccatc gcccacgccg tgcccttcta   1380
cggctgcgtc aactggacca atgagaactt tcccttcaac gattgcgtcg acaagatggt   1440
gatctggtgg gaggagggca agatgacggc caaggtcgtg gagtccgcca aggccattct   1500
cggcggcagc aaggtgcgcg tggaccaaaa gtgcaagtcg tccgcccaga tcgatcccac   1560
ccccgtgatc gtcacctcca acaccaacat gtgcgccgtg attgacggga acagcaccac   1620
cttcgagcac cagcagccgt tgcaggaccg gatgttcaaa tttgaactca cccgccgtct   1680
ggagcatgac tttggcaagg tgacaaagca ggaagtcaaa gagttcttcc gctgggcgca   1740
ggatcacgtg accgaggtgg cgcatgagtt ctacgtcaga agggtggag ccaacaagag   1800 acccgcccc gatgacgcgg ataaaagcga gcccaagcgg gcctgccct cagtcgcgga   1860 tccatcgacg tcagacgcgg aaggagctcc ggtggacttt gccgacaggt accaaaacaa   1920
atgttctcgt cacgcgggca tgcttcagat gctgttccc tgcaaaacat gcgagagaat   1980
gaatcagaat ttcaacattt gcttcacgca cgggaccaga gactgttcag aatgtttccc   2040
cggcgtgtca gaatctcaac cggtcgtcag aaagaggacg tatcggaaac tctgtgccat   2100
tcatcatctg ctggggcggg ctcccgagat tgcttgctcg gcctgcgatc tggtcaacgt   2160
ggatctggat gactgtgttt ctgagcaata aatgacttaa accaggtatg gctgccgatg   2220
gttatcttcc agattggctc gaggacaacc tctctgaggg cattcgcgag tggtgggact   2280
tgaaacctgg agccccgaaa cccaaagcca accagcaaaa gcaggacgac ggccgggtc   2340 tggtgcttcc tggctacaag tacctcggac ccttcaacgg actcgacaag ggggagcccg   2400
tcaacgcggc ggatgcagcg gccctcgagc acgacaaggc ctacgaccag cagctcaaag   2460
cgggtgacaa tccgtacctg cggtataacc acgccgacgc cgagtttcag gagcgtctgc   2520
aagaagatac gtcttttggg ggcaacctcg gcgagcagt cttccaggcc aagaagaggg   2580
ttctcgaacc ttttggtctg gttgaggaag gtgctaagac ggctcctgga aagaaacgtc   2640
cggtagagca gtcgccacaa gagccagact cctcctcggg cattggcaag acaggccagc   2700
```

```
agcccgctaa aaagagactc aattttggtc agactggcga ctcagagtca gtccccgacc    2760
cacaacctct cggagaacct ccagcaaccc ccgctgctgt gggacctact acaatggctt    2820
caggcggtgg cgcaccaatg cagacaata  acgaaggcgc cgacggagtg gtaatgcct     2880
caggaaattg gcattgcgat tccacatggc tgggcgacag agtcatcacc accagcaccc    2940
gaacatgggc cttgcccacc tataacaacc acctctacaa gcaaatctcc agtgcttcaa    3000
cgggggccag caacgacaac cactacttcg gctacagcac ccctgggggg tatttttgatt   3060
tcaacagatt ccactgccat ttctcaccac gtgactggca gcgactcatc aacaacaatt    3120
ggggattccg gcccaagaga ctcaacttca agctcttcaa catccaagtc aaggaggtca    3180
cgacgaatga tggcgtcacg accatcgcta ataaccttac cagcacggtt caagtcttct    3240
cggactcgga gtaccagttg ccgtacgtcc tcggctctgc gcaccagggc tgcctccctc    3300
cgttcccggc ggacgtgttc atgattccgc agtacggcta cctaacgctc aacaatggca    3360
gccaggcagt gggacggtca tccttttact gcctggaata tttcccatcg cagatgctga    3420
gaacgggcaa taactttacc ttcagctaca ccttcgagga cgtgcctttc cacagcagct    3480
acgcgcacag ccagagcctg gaccggctga tgaatcctct catcgaccag tacctgtatt    3540
acctgaacag aactcagaat cagtccggaa gtgcccaaaa caaggacttg ctgtttagcc    3600
gggggtctcc agctggcatg tctgttcagc ccaaaaactg gctacctgga ccctgttacc    3660
ggcagcagcg cgtttctaaa acaaaaacag acaacaacaa cagcaacttt acctggactg    3720
gtgcttcaaa atataacctt aatgggcgtg aatctataat caaccctggc actgctatgg    3780
cctcacacaa agacgacaaa gacaagttct ttcccatgag cggtgtcatg attttttggaa   3840
aggagagcgc cggagcttca aacactgcat tggacaatgt catgatcaca gacgaagagg    3900
aaatcaaagc cactaacccc gtggccaccg aaagatttgg gactgtggca gtcaatctcc    3960
agagcagcag cacagaccct gcgaccgagg atgtgcatgt tatgggagcc ttacctggaa    4020
tggtgtggca agacagagac gtatacctgc agggtcctat ttgggccaaa attcctcaca    4080
cggatggaca ctttcacccg tctcctctca tgggcggctt tggacttaag cacccgcctc    4140
ctcagatcct catcaaaaac acgcctgttc ctgcgaatcc tccggcagag ttttcggcta    4200
caaagtttgc ttcattcatc acccagtatt ccacaggaca agtgagcgtg gagattgaat    4260
gggagctgca gaaagaaaac agcaaacgct ggaatcccga agtgcagtat acatctaact    4320
atgcaaaatc tgccaacgtt gatttcactg tggacaacaa tggacttyat actgagcctc    4380
gccccattgg caccgttac  ctcacccgtc cctgtaatt  gtgtgttaat caataaaccg    4440
gttaattcgt gtcagttgaa ctttggtctc atgtcgttat tatcttatct ggtcaccata    4500
gcaaccggtt acacattaac tgcttagttg cgcttcgcga ataccctag  tgatggagtt    4560
gcccactccc tctatgcgcg ctcgctcgct cggtggggcc ggcagagcag agctctgccg    4620
tctgcggacc tttggtccgc aggccccacc gagcgagcga gcgcgcatag agggagtggg    4680
caa                                                                  4683
```

<210> SEQ ID NO 15
<211> LENGTH: 4721
<212> TYPE: DNA
<213> ORGANISM: Dependoparvovirus Adeno-associated virus - 7

<400> SEQUENCE: 15

```
ttggccactc cctctatgcg cgctcgctcg ctcggtgggg cctgcggacc aaaggtccgc     60
```

```
agacggcaga gctctgctct gccggccccca ccgagcgagc gagcgcgcat agagggagtg    120
gccaactcca tcactagggg taccgcgaag cgcctcccac gctgccgcgt cagcgctgac    180
gtaaatcacg tcataggggga gtggtcctgt attagctgtc acgtgagtgc ttttgcgaca    240
ttttgcgaca ccacgtggcc atttgaggta tatatggccg agtgagcgag caggatctcc    300
attttgaccg cgaaatttga acgagcagca gccatgccgg gtttctacga gatcgtgatc    360
aaggtgccga cgaccctgga cgagcacctg ccgggcattt ctgactcgtt tgtgaactgg    420
gtggccgaga aggaatggga gctgccccg gattctgaca tggatctgaa tctgatcgag    480
caggcacccc tgaccgtggc cgagaagctg cagcgcgact tcctggtcca atggcgccgc    540
gtgagtaagg ccccggaggc cctgttcttt gttcagttcg agaagggcga gagctacttc    600
caccttcacg ttctggtgga gaccacgggg gtcaagtcca tggtgctagg ccgcttcctg    660
agtcagattc gggagaagct ggtccagacc atctaccgcg gggtcgagcc cacgctgccc    720
aactggttcg cggtgaccaa gacgcgtaat ggcgccggcg ggggaacaa ggtggtggac    780 gagtgctaca tcccccaacta cctcctgccc aagacccagc ccgagctgca gtgggcgtgg    840
actaacatgg aggagtatat aagcgcgtgt ttgaacctgg ccgaacgcaa acggctcgtg    900
gcgcagcacc tgacccacgt cagccagacg caggagcaga acaaggagaa tctgaacccc    960
aattctgacg cgcccgtgat caggtcaaaa acctccgcgc gctacatgga gctggtcggg   1020
tggctggtgg accggggcat cacctccgag aagcagtgga tccaggagga ccaggcctcg   1080
tacatctcct tcaacgccgc ctccaactcg cggtcccaga tcaaggccgc gctggacaat   1140
gccggcaaga tcatgcgcct gaccaaatcc gcgcccgact acctggtggg gccctcgctg   1200
cccgcggaca ttaaaaccaa ccgcatctac cgcatcctgg agctgaacgg gtacgatcct   1260
gcctacgccg gctccgtctt tctcggctgg gcccagaaaa agttcgggaa gcgcaacacc   1320
atctggctgt ttgggcccgc caccaccggc aagaccaaca ttgcggaagc catcgcccac   1380
gccgtgccct tctacggctg cgtcaactgg accaatgaga ctttcccctt caacgattgc   1440
gtcgacaaga tggtgatctg gtgggaggag ggcaagatga cggccaaggt cgtggagtcc   1500
gccaaggcca ttctcggcgg cagcaaggtg gcgtggacc aaaagtgcaa gtcgtccgcc   1560
cagatcgacc ccaccccccgt gatcgtcacc tccaacacca acatgtgcgc cgtgattgac   1620
gggaacagca ccaccttcga gcaccagcag ccgttgcagg accggatgtt caaatttgaa   1680
ctcacccgcc gtctggagca cgactttggc aaggtgacga agcaggaagt caaagagttc   1740
ttccgctggg ccagtgatca cgtgaccgag gtggcgcatg agttctacgt cagaaagggc   1800
ggagccagca aaagacccgc ccccgatgac gcggatataa gcgagcccaa gcgggcctgc   1860
ccctcagtcg cggatccatc gacgtcagac gcggaaggag ctccggtgga ctttgccgac   1920
aggtaccaaa acaaatgttc tcgtcacgcg ggcatgattc agatgctgtt tccctgcaaa   1980
acgtgcgaga gaatgaatca gaatttcaac atttgcttca cacacggggt cagagactgt   2040
ttagagtgtt tccccggcgt gtcagaatct caaccggtcg tcagaaaaaa gacgtatcgg   2100
aaactctgcg cgattcatca tctgctgggg cgggcgcccg agattgcttg ctcggcctgc   2160
gacctggtca acgtggacct ggacgactgc gtttctgagc aataaatgac ttaaaccagg   2220
tatggctgcc gatggttatc ttccagattg gctcgaggac aacctctctg agggcattcg   2280
cgagtggtgg gacctgaaac ctggagcccc gaaacccaaa gccaaccagc aaaagcagga   2340
caacggccgg ggtctggtgc ttcctggcta caagtacctc ggaccttcca acggactcga   2400 caaggggggag cccgtcaacg cggcggacgc agcggccctc gagcacgaca aggcctacga   2460
```

```
ccagcagctc aaagcgggtg acaatccgta cctgcggtat aaccacgccg acgccgagtt    2520
tcaggagcgt ctgcaagaag atacgtcatt tgggggcaac ctcgggcgag cagtcttcca    2580
ggccaagaag cgggttctcg aacctctcgg tctggttgag aaggcgcta agacggctcc    2640 tgcaaagaag agaccggtag agccgtcacc tcagcgttcc cccgactcct ccacgggcat    2700
cggcaagaaa ggccagcagc ccgccagaaa gagactcaat ttcggtcaga ctggcgactc    2760
agagtcagtc cccgaccctc aacctctcgg agaacctcca gcagcgccct ctagtgtggg    2820
atctggtaca gtggctgcag gcggtggcgc accaatggca gacaataacg aaggtgccga    2880
cggagtgggt aatgcctcag gaaattggca ttgcgattcc acatggctgg gcgacagagt    2940
cattaccacc agcacccgaa cctgggccct gcccacctac aacaaccacc tctacaagca    3000
aatctccagt gaaactgcag gtagtaccaa cgacaacacc tacttcggct acagcacccc    3060
ctgggggtat tttgacttta acagattcca ctgccacttc tcaccacgtg actggcagcg    3120
actcatcaac aacaactggg gattccggcc aagaagctg cggttcaagc tcttcaacat    3180
ccaggtcaag gaggtcacga cgaatgacgg cgttacgacc atcgctaata accttaccag    3240
cacgattcag gtattctcgg actcggaata ccagctgccg tacgtcctcg gctctgcgca    3300
ccagggctgc ctgcctccgt tcccggcgga cgtcttcatg attcctcagt acggctacct    3360
gactctcaac aatggcagtc agtctgtggg acgttcctcc ttctactgcc tggagtactt    3420
cccctctcag atgctgagaa cgggcaacaa ctttgagttc agctacagct cgaggacgt    3480 gcctttccac agcagctacg cacacagcca gagcctggac cggctgatga atcccctcat    3540
cgaccagtac ttgtactacc tggccagaac acagagtaac ccaggaggca cagctggcaa    3600
tcgggaactg cagttttacc agggcgggcc ttcaactatg gccgaacaag ccaagaattg    3660
gttacctgga ccttgcttcc ggcaacaaag agtctccaaa acgctggatc aaaacaacaa    3720
cagcaacttt gcttggactg gtgccaccaa atatcacctg aacggcagaa actcgttggt    3780
taatcccggc gtcgccatgg caactcacaa ggacgacgag gaccgctttt tcccatccag    3840
cggagtcctg attttggaa aaactggagc aactaacaaa actacattgg aaaatgtgtt    3900
aatgacaaat gaagaagaaa ttcgtcctac taatcctgta gccacggaag aatacgggat    3960
agtcagcagc aacttacaag cggctaatac tgcagcccag acacaagttg tcaacaacca    4020
gggagcctta cctggcatgg tctgcagaa ccgggacgtg tacctgcagg gtcccatctg    4080
ggccaagatt cctcacacgg atggcaactt cacccgtcct cctttgatgg gcggctttgg    4140
acttaaacat ccgcctcctc agatcctgat caagaacact cccgttcccg ctaatcctcc    4200
ggaggtgttt actcctgcca gtttgcttc gttcatcaca cagtacagca ccggacaagt    4260
cagcgtggaa atcgagtggg agctgcagaa ggaaaacagc aagcgctgga cccggagat    4320 tcagtacacc tccaactttg aaaagcagac tggtgtggac tttgccgttg acagccaggg    4380
tgtttactct gagcctcgcc ctattggcac tcgttacctc acccgtaatc tgtaattgca    4440
tgttaatcaa taaaccggtt gattcgtttc agttgaactt tggtctcctg tgcttcttat    4500
cttatcggtt tccatagcaa ctggttacac attaactgct tgggtgcgct tcacgataag    4560
aacactgacg tcaccgcggt accctagtg atggagttgg ccactccctc tatgcgcgct    4620
cgctcgctcg gtgggcctg cggaccaaag gtccgcagac ggcagagctc tgctctgccg    4680 gcccaccga gcgagcgagc gcgcatagag ggagtggcca a                        4721
```

<210> SEQ ID NO 16

<211> LENGTH: 4393
<212> TYPE: DNA
<213> ORGANISM: Dependoparvovirus Adeno-associated virus - 8

<400> SEQUENCE: 16

```
cagagaggga gtggccaact ccatcactag gggtagcgcg aagcgcctcc cacgctgccg    60
cgtcagcgct gacgtaaatt acgtcatagg ggagtggtcc tgtattagct gtcacgtgag   120
tgcttttgcg gcattttgcg acaccacgtg gccatttgag gtatatatgg ccagtgagc    180
gagcaggatc tccattttga ccgcgaaatt tgaacgagca gcagccatgc cgggcttcta   240
cgagatcgtg atcaaggtgc cgagcgacct ggacgagcac ctgccgggca tttctgactc   300
gtttgtgaac tgggtggccg agaaggaatg ggagctgccc ccggattctg acatggatcg   360
gaatctgatc gagcaggcac ccctgaccgt ggccgagaag ctgcagcgcg acttcctggt   420
ccaatggcgc cgcgtgagta aggccccgga ggccctcttc tttgttcagt cgagaaggg   480
cgagagctac tttcacctgc acgttctggt cgagaccacg ggggtcaagt ccatggtgct   540
aggccgcttc ctgagtcaga ttcggggaaaa gcttggtcca gaccatctac ccgcggggtc   600
gagcccacc ttgcccaact ggttcgcggt gaccaaagac gcggtaatgg cgccggcggg   660
ggggaacaag gtggtggacg agtgctacat ccccaactac ctcctgccca agactcagcc   720
cgagctgcag tgggcgtgga ctaacatgga ggagtatata agcgcgtgct tgaacctggc   780
cgagcgcaaa cggctcgtgg cgcagcacct gacccacgtc agccagacgc aggagcagaa   840
caaggagaat ctgaaccca attctgacgc gcccgtgatc aggtcaaaaa cctccgcgcg   900
ctatatggag ctggtcgggt ggctggtgga ccggggcatc acctccgaga agcagtggat   960
ccaggaggac caggcctcgt acatctcctt caacgccgcc tccaactcgc ggtcccagat  1020
caaggccgcg ctgacaatg ccggcaagat catggcgctg accaaatccg cgcccgacta  1080
cctggtgggg ccctcgctgc ccgcggacat tacccagaac cgcatctacc gcatcctcgc  1140
tctcaacggc tacgaccctg cctacgccgg ctccgtcttt ctcggctggg ctcagaaaaa  1200
gttcgggaaa cgcaacacca tctggctgtt tggacccgcc accaccggca agaccaacat  1260
tgcggaagcc atcgcccacg ccgtgccctt ctacggctgc gtcaactgga ccaatgagaa  1320
cttttccttc aatgattgcg tcgacaagat ggtgatctgg tgggaggagg gcaagatgac  1380
ggccaaggtc gtggagtccg ccaaggccat tctcggcggc agcaaggtgc gcgtggacca  1440
aaagtgcaag tcgtccgccc agatcgaccc caccccgtg atcgtcacct ccaacaccaa  1500
catgtgcgcc gtgattgacg ggaacagcac caccttcgag caccagcagc ctctccagga  1560
ccggatgttt aagttcgaac tcacccgccg tctggagcac gactttggca aggtgacaaa  1620
gcaggaagtc aaagagttct tccgctgggc cagtgatcac gtgaccgagg tggcgcatga  1680
gttttacgtc agaaagggcg gagccagcaa aagacccgcc ccgatgacg cggataaaag  1740
cgagcccaag cgggcctgcc cctcagtcgc ggatccatcg acgtcagacg cggaaggagc  1800
tccggtggac tttgccgaca ggtaccaaaa caatgttct cgtcacgcgg gcatgcttca  1860
gatgctgttt ccctgcaaaa cgtgcgagag aatgaatcag aattcaaca tttgcttcac  1920
acacggggtc agagactgct cagagtgttt ccccggcgtg tcagaatctc aaccggtcgt  1980
cagaaagagg acgtatcgga aactctgtgc gattcatcat ctgctgggc gggctcccga  2040
gattgcttgc tcggcctgcg atctggtcaa cgtggacctg gatgactgtg tttctgagca  2100
ataaatgact taaaccaggt atggctgccg atggttatct tccagattgg ctcgaggaca  2160
acctctctga gggcattcgc gagtggtggg cgctgaaacc tggagccccg aagcccaaag  2220
```

-continued

```
ccaaccagca aaagcaggac gacggccggg gtctggtgct tcctggctac aagtacctcg    2280
gacccttcaa cggactcgac aagggggagc ccgtcaacgc ggcggacgca gcggccctcg    2340
agcacgacaa ggcctacgac cagcagctgc aggcgggtga caatccgtac ctgcggtata    2400
accacgccga cgccgagttt caggagcgtc tgcaagaaga tacgtctttt gggggcaacc    2460
tcgggcgagc agtcttccag gccaagaagc gggttctcga acctctcggt ctggttgagg    2520
aaggcgctaa gacggctcct ggaaagaaga gaccggtaga gccatcaccc cagcgttctc    2580
cagactcctc tacgggcatc ggcaagaaag ccaacagcc cgccagaaaa agactcaatt    2640
ttggtcagac tggcgactca gagtcagttc agacccctca acctctcgga gaacctccag    2700
cagcgccctc tggtgtggga cctaatacaa tggctgcagg cggtggcgca ccaatggcag    2760
acaataacga aggcgccgac ggagtgggta gttcctcggg aaattggcat tgcgattcca    2820
catggctggg cgacagagtc atcaccacca gcacccgaac ctgggccctg cccacctaca    2880
acaaccacct ctacaagcaa atctccaacg ggacatcggg aggagccacc aacgacaaca    2940
cctacttcgg ctacagcacc ccctgggggt attttgactt aacagattc cactgccact    3000
tttcaccacg tgactggcag cgactcatca acaacaactg gggattccgg cccaagagac    3060
tcagcttcaa gctcttcaac atccaggtca aggaggtcac gcagaatgaa ggcaccaaga    3120
ccatcgccaa taacctcacc agcaccatcc aggtgtttac ggactcggag taccagctgc    3180
cgtacgttct cggctctgcc caccagggct gcctgcctcc gttcccggcg acgtgttca    3240
tgattcccca gtacggctac ctaacactca acaacgtag tcaggccgtg ggacgctcct    3300
ccttctactg cctggaatac tttccttcgc agatgctgag aaccggcaac aacttccagt    3360
ttacttacac cttcgaggac gtgccttttc acagcagcta cgcccacagc cagagcttgg    3420
accggctgat gaatcctctg attgaccagt acctgtacta cttgtctcgg actcaaacaa    3480
caggaggcac ggcaaatacg cagactctgg gcttcagcca aggtgggcct aatacaatgg    3540
ccaatcaggc aaagaactgg ctgccaggac cctgttaccg ccaacaacgc gtctcaacga    3600
caaccgggca aaacaacaat agcaactttg cctggactgc tgggaccaaa taccatctga    3660
atggaagaaa ttcattggct aatcctggca tcgctatggc aacacacaaa gacgacgagg    3720
agcgtttttt tcccagtaac gggatcctga tttttggcaa acaaaatgct gccagagaca    3780
atgcggatta cagcgatgtc atgctcacca gcgaggaaga aatcaaaacc actaaccctg    3840
tggctacaga ggaatacggt atcgtggcag ataacttgca gcagcaaaac acggctcctc    3900
aaattggaac tgtcaacagc caggggggcct tacccggtat ggtctggcag aaccgggacg    3960
tgtacctgca gggtcccatc tgggccaaga ttcctcacac ggacggcaac ttccacccgt    4020
ctccgctgat gggcggcttt ggcctgaaac atcctccgcc tcagatcctg atcaagaaca    4080
cgcctgtacc tgcggatcct ccgaccacct tcaaccagtc aaagctgaac tctttcatca    4140
cgcaatacag caccggacag gtcagcgtgg aaattgaatg ggagctgcag aaggaaaaca    4200
gcaagcgctg gaaccccgag atccagtaca cctccaacta ctacaaatct acaagtgtgg    4260
actttgctgt taatacagaa ggcgtgtact ctgaaccccg ccccattggc acccgttacc    4320
tcacccgtaa tctgtaattg cctgttaatc aataaaccgg ttgattcgtt tcagttgaac    4380
tttggtctct gcg                                                       4393
```

```
<210> SEQ ID NO 17
<211> LENGTH: 2211
<212> TYPE: DNA
```

<213> ORGANISM: Dependoparvovirus Adeno-associated virus - 9

<400> SEQUENCE: 17

| | | | | | |
|---|---|---|---|---|---|
| atggctgccg | atggttatct | tccagattgg | ctcgaggaca | accttagtga | aggaattcgc | 60 |
| gagtggtggg | cttttgaaacc | tggagcccct | caacccaagg | caaatcaaca | acatcaagac | 120 |
| aacgctcgag | gtcttgtgct | tccgggttac | aaataccttg | acccggcaa | cggactcgac | 180 |
| aaggggagc | cggtcaacgc | agcagacgcg | gcggccctcg | agcacgacaa | ggcctacgac | 240 |
| cagcagctca | aggccggaga | caacccgtac | ctcaagtaca | accacgccga | cgccgagttc | 300 |
| caggagcggc | tcaaagaaga | tacgtctttt | gggggcaacc | tcgggcgagc | agtcttccag | 360 |
| gccaaaaaga | ggcttcttga | acctcttggt | ctggttgagg | aagcggctaa | gacggctcct | 420 |
| ggaaagaaga | ggcctgtaga | gcagtctcct | caggaaccgg | actcctccgc | gggtattggc | 480 |
| aaatcgggtg | cacagcccgc | taaaaagaga | ctcaatttcg | gtcagactgg | cgacacagag | 540 |
| tcagtcccag | accctcaacc | aatcggagaa | cctcccgcag | ccccctcagg | tgtgggatct | 600 |
| cttacaatgg | cttcaggtgg | tggcgcacca | gtggcagaca | ataacgaagg | tgccgatgga | 660 |
| gtgggtagtt | cctcgggaaa | ttggcattgc | gattcccaat | ggctggggga | cagagtcatc | 720 |
| accaccagca | cccgaacctg | ggccctgccc | acctacaaca | atcacctcta | caagcaaatc | 780 |
| tccaacagca | catctggagg | atcttcaaat | gacaacgcct | acttcggcta | cagcaccccc | 840 |
| tgggggtatt | ttgacttcaa | cagattccac | tgccacttct | caccacgtga | ctggcagcga | 900 |
| ctcatcaaca | acaactgggg | attccggcct | aagcgactca | acttcaagct | cttcaacatt | 960 |
| caggtcaaag | aggttacgga | caacaatgga | gtcaagacca | tcgccaataa | ccttaccagc | 1020 |
| acggtccagg | tcttcacgga | ctcagactat | cagctcccgt | acgtgctcgg | tcggctcac | 1080 |
| gagggctgcc | tcccgccgtt | cccagcgac | gttttcatga | ttcctcagta | cgggtatctg | 1140 |
| acgcttaatg | atggaagcca | ggccgtgggt | cgttcgtcct | tttactgcct | ggaatatttc | 1200 |
| ccgtcgcaaa | tgctaagaac | gggtaacaac | ttccagttca | gctacgagtt | tgagaacgta | 1260 |
| cctttccata | gcagctacgc | tcacagccaa | agcctggacc | gactaatgaa | tccactcatc | 1320 |
| gaccaatact | tgtactatct | ctcaaagact | attaacggtt | ctggacagaa | tcaacaaacg | 1380 |
| ctaaaattca | gtgtggccgg | acccagcaac | atggctgtcc | agggaagaaa | ctacatacct | 1440 |
| ggacccagct | accgacaaca | acgtgtctca | accactgtga | ctcaaaacaa | caacagcgaa | 1500 |
| tttgcttggc | ctggagcttc | ttcttgggct | ctcaatggac | gtaatagctt | gatgaatcct | 1560 |
| ggacctgcta | tggccagcca | caaagaagga | gaggaccgtt | tctttcctt | gtctggatct | 1620 |
| ttaattttg | gcaaacaagg | aactggaaga | dacaacgtgg | atgcggacaa | agtcatgata | 1680 |
| accaacgaag | aagaaattaa | aactactaac | ccggtagcaa | cggagtccta | tggacaagtg | 1740 |
| gccacaaacc | accagagtgc | ccaagcacag | cgcagaccg | gctggttca | aaaccaagga | 1800 |
| atacttccgg | gtatggtttg | gcaggacaga | gatgtgtacc | tgcaaggacc | catttgggcc | 1860 |
| aaaattcctc | acacggacgg | caactttcac | ccttctccgc | tgatgggagg | gtttggaatg | 1920 |
| aagcacccgc | ctcctcagat | cctcatcaaa | aacacacctg | tacctgcgga | tcctccaacg | 1980 |
| gccttcaaca | aggacaagct | gaactctttc | atcacccagt | attctactgg | ccaagtcagc | 2040 |
| gtggagatcg | agtgggagct | gcagaaggaa | aacagcaagc | gctggaaccc | ggagatccag | 2100 |
| tacacttcca | actattacaa | gtctaataat | gttgaatttg | ctgttaatac | tgaaggtgta | 2160 |
| tatagtgaac | ccgccccat | tggcaccaga | tacctgactc | gtaatctgta | a | 2211 |

<210> SEQ ID NO 18
<211> LENGTH: 4102
<212> TYPE: DNA
<213> ORGANISM: Dependoparvovirus Adeno-associated virus - 10

<400> SEQUENCE: 18

| | | | | | |
|---|---|---|---|---|---|
| atgccgggct | tctacgagat | cgtgatcaag | gtgccgagcg | acctggacga | gcacctgccg | 60 |
| ggcatttctg | actcgtttgt | gaactgggtg | gccgagaagg | aatgggagct | gccccggat | 120 |
| tctgacatgg | atcggaatct | gatcgagcag | gcacccctga | ccgtggccga | gaagctgcag | 180 |
| cgcgacttcc | tggtccactg | gcgccgcgtg | agtaaggccc | cggaggccct | cttctttgtt | 240 |
| cagttcgaga | agggcgagtc | ctactttcac | ctgcacgttc | tggtcgagac | cacgggggtc | 300 |
| aagtccatgg | tcctgggccg | cttcctgagt | cagatcagag | acaggctggt | gcagaccatc | 360 |
| taccgcgggg | tagagcccac | gctgcccaac | tggttcgcgg | tgaccaagac | gcgaaatggc | 420 |
| gccggcgggg | ggaacaaggt | ggtggacgag | tgctacatcc | ccaactacct | cctgcccaag | 480 |
| acgcagcccg | agctgcagtg | gcgtggact | aacatggagg | agtatataag | cgcgtgtctg | 540 |
| aacctcgcgg | agcgtaaacg | gctcgtggcg | cagcacctga | cccacgtcag | ccagacgcag | 600 |
| gagcagaaca | aggagaatct | gaacccgaat | tctgacgcgc | ccgtgatcag | gtcaaaaacc | 660 |
| tccgcgcgct | acatggagct | ggtcgggtgg | ctggtggacc | ggggcatcac | ctccgagaag | 720 |
| cagtggatcc | aggaggacca | ggcctcgtac | atctccttca | acgccgcctc | caactcgcgg | 780 |
| tcccagatca | aggccgcgct | ggacaatgcc | ggaaagatca | tggcgctgac | caaatccgcg | 840 |
| cccgactacc | tggtaggccc | gtccttaccc | gcggacatta | aggccaaccg | catctaccgc | 900 |
| atcctggagc | tcaacggcta | cgaccccgcc | tacgccggct | ccgtcttcct | gggctgggcg | 960 |
| cagaaaaagt | tcggtaaaag | gaatacaatt | tggctgttcg | gcccgccac | caccggcaag | 1020 |
| accaacatcg | cggaagccat | cgcccacgcc | gtgcccttct | acggctgcgt | caactggacc | 1080 |
| aatgagaact | ttccccttca | acgattgcgtc | gacaagatgg | tgatctggtg | ggaggagggc | 1140 |
| aagatgaccg | ccaaggtcgt | ggagtccgcc | aaggccattc | tgggcggaag | caaggtgcgc | 1200 |
| gtcgaccaaa | agtgcaagtc | ctcggcccag | atcgaccca | cgcccgtgat | cgtcacctcc | 1260 |
| aacaccaaca | tgtgcgccgt | gatcgacggg | aacagcacca | ccttcgagca | ccagcagccc | 1320 |
| ctgcaggacc | gcatgttcaa | gttcgagctc | acccgccgtc | tggagcacga | ctttggcaag | 1380 |
| gtgaccaagc | aggaagtcaa | agagttcttc | cgctgggctc | aggatcacgt | gactgaggtg | 1440 |
| acgcatgagt | tctacgtcag | aaagggcgga | gccaccaaaa | gacccgcccc | cagtgacgcg | 1500 |
| gatataagcg | agcccaagcg | ggcctgcccc | tcagttgcgg | agccatcgac | gtcagacgcg | 1560 |
| gaagcaccgg | tggactttgc | ggacaggtac | caaaacaaat | gttctcgtca | cgcgggcatg | 1620 |
| cttcagatgc | tgtttccctg | caagacatgc | gagagaatga | atcagaattt | caacgtctgc | 1680 |
| ttcacgcacg | gggtcagaga | ctgctcagag | tgcttccccg | gcgcgtcaga | atctcaacct | 1740 |
| gtcgtcagaa | aaagacgta | tcagaaactg | tgcgcgattc | atcatctgct | ggggcgggca | 1800 |
| cccgagattg | cgtgttcggc | ctgcgatctc | gtcaacgtgg | acttggatga | ctgtgtttct | 1860 |
| gagcaataaa | tgacttaaac | caggtatggc | tgctgacggt | tatcttccag | attggctcga | 1920 |
| ggacaacctc | tctgagggca | ttcgcgagtg | gtggacctga | aaacctggag | cccccaagcc | 1980 |
| caaggccaac | cagcagaagc | aggacgacgg | ccggggtctg | gtgcttcctg | gctacaagta | 2040 |
| cctcggaccc | ttcaacggac | tcgacaaggg | ggagcccgtc | aacgcggcgg | acgcagcggc | 2100 |
| cctcgagcac | gacaaggcct | acgaccagca | gctcaaagcg | ggtgacaatc | cgtacctgcg | 2160 |

```
gtataaccac gccgacgccg agtttcagga gcgtctgcaa aagatacgt cttttggggg    2220 caacctcggg cgagcagtct tccaggccaa gaagcgggtt ctcgaacctc tcggtctggt    2280
tgaggaagct gctaagacgg ctcctggaaa gaagagaccg gtagaaccgt cacctcagcg    2340
ttcccccgac tcctcacagg gcatcggcaa gaaaggccag cagcccgcta aaaagagact    2400
gaactttggg cagactggcg agtcagagtc agtccccgac cctcaaccaa tcggagaacc    2460
accagcaggc ccctctggtc tgggatctgg tacaatggct gcaggcggtg gcgctccaat    2520
ggcagacaat aacgaaggcg ccgacggagt gggtagttcc tcaggaaatt ggcattgcga    2580
ttccacatgg ctgggcgaca gagtcatcac caccagcacc cgaacctggg ccctgcccac    2640
ctacaacaac cacctctaca agcaaatctc caacgggaca tcgggaggaa gcaccaacga    2700
caacacctac ttcggctaca gcacccctg ggggtatttt gacttcaaca gattccactg    2760
ccacttctca ccacgtgact ggcagcgact catcaacaac aactgggat tccggccaaa    2820 aagactcagc ttcaagctct tcaacatcca ggtcaaggag gtcacgcaga atgaaggcac    2880
caagaccatc gccaataacc ttaccagcac gattcaggta tttacggact cggaatacca    2940
gctgccgtac gtcctcggct ccgcgcacca gggctgcctg cctccgttcc cggcggatgt    3000
cttcatgatt ccccagtacg gctacctgac actgaacaat ggaagtcaag ccgtaggccg    3060
ttcctccttc tactgcctgg aatattttcc atctcaaatg ctgcgaactg gaaacaattt    3120
tgaattcagc tacaccttcg aggacgtgcc tttccacagc agctacgcac acagccagag    3180
cttggaccga ctgatgaatc ctctcattga ccagtacctg tactacttat ccagaactca    3240
gtccacagga ggaactcaag gtacccagca attgttattt tctcaagctg gcctgcaaa    3300 catgtcggct caggccaaga actggctgcc tggaccttgc taccggcagc agcgagtctc    3360
cacgacactg tcgcaaaaca caacagcaa ctttgcttgg actggtgcca ccaaatatca    3420
cctgaacgga agagactctc tggtgaatcc cggtgtcgcc atggcaaccc acaaggacga    3480
cgaggaacgc ttcttcccgt cgagcggagt cctgatgttt ggaaaacagg gtgctggaag    3540
agacaatgtg gactacagca gcgttatgct aacaagcgaa gaagaaatta aaccactaa    3600 ccctgtagcc acagaacaat acggcgtggt ggctgacaac ttgcagcaag ccaatacagg    3660
gcctattgtg ggaaatgtca acagccaagg agccttacct ggcatggtct ggcagaaccg    3720
agacgtgtac ctgcagggtc ccatctgggc caagattcct cacacggacg gcaactttca    3780
cccgtctcct ctgatgggcg gctttggact taaacacccg cctccacaga tcctgatcaa    3840
gaacacgccg gtacctgcgg atcctccaac aacgttcagc caggcgaaat tggcttcctt    3900
catcacgcag tacagcaccg gacaggtcag cgtggaaatc gagtgggagc tgcagaagga    3960
gaacagcaaa cgctggaacc cagagattca gtacacttca aactactaca aatctacaaa    4020
tgtggacttt gctgtcaata cagagggaac ttattctgag cctcgcccca ttggtactcg    4080
ttatctgaca cgtaatctgt aa                                            4102
```

<210> SEQ ID NO 19
<211> LENGTH: 4087
<212> TYPE: DNA
<213> ORGANISM: Dependoparvovirus Adeno-associated virus - 11

<400> SEQUENCE: 19

```
atgccgggct tctacgagat cgtgatcaag gtgccgagcg acctggacga gcacctgccg    60
ggcatttctg actcgtttgt gaactgggtg gccgagaagg aatgggagct gccccccggat   120 tctgacatgg atcggaatct gatcgagcag gcacccctga ccgtggccga aagctgcag    180
```

```
cgcgacttcc tggtccactg gcgccgcgtg agtaaggccc cggaggccct cttctttgtt    240
cagttcgaga agggcgagtc ctacttccac ctccacgttc tcgtcgagac cacgggggtc    300
aagtccatgg tcctgggccg cttcctgagt cagatcagag acaggctggt gcagaccatc    360
taccgcgggg tcgagcccac gctgcccaac tggttcgcgg tgaccaagac gcgaaatggc    420
gccggcgggg ggaacaaggt ggtggacgag tgctacatcc ccaactacct cctgcccaag    480
acccagcccg agctgcagtg ggcgtggact aacatggagg agtatataag cgcgtgtcta    540
aacctcgcgg agcgtaaacg gctcgtggcg cagcacctga cccacgtcag ccagacgcag    600
gagcagaaca aggagaatct gaacccgaat tctgacgcgc ccgtgatcag gtcaaaaacc    660
tccgcgcgct acatggagct ggtcgggtgg ctggtggacc ggggcatcac ctccgagaag    720
cagtggatcc aggaggacca ggcctcgtac atctccttca cgccgcctc caactcgcgg    780 tcccagatca aggccgcgct ggacaatgcc ggaaagatca tggcgctgac caaatccgcg    840
cccgactacc tggtaggccc gtccttaccc gcggacatta aggccaaccg catctaccgc    900
atcctggagc tcaacggcta cgaccccgcc tacgccggct ccgtcttcct gggctgggcg    960
cagaaaaagt tcggtaaacg caacaccatc tggctgtttg gcccgccac caccggcaag    1020 accaacatcg cggaagccat agcccacgcc gtgcccttct acggctgcgt gaactggacc    1080
aatgagaact ttcccttcaa cgattgcgtc gacaagatgg tgatctggtg ggaggagggc    1140
aagatgaccg ccaaggtcgt ggagtccgcc aaggccattc tgggcggaag caaggtgcgc    1200
gtggaccaaa agtgcaagtc ctcggcccag atcgaccca cgcccgtgat cgtcacctcc    1260
aacaccaaca tgtgcgccgt gatcgacggg aacagcacca ccttcgagca ccagcagccg    1320
ctgcaggacc gcatgttcaa gttcgagctc acccgccgtc tggagcacga ctttggcaag    1380
gtgaccaagc aggaagtcaa agagttcttc cgctgggctc aggatcacgt gactgaggtg    1440
gcgcatgagt tctacgtcag aaagggcgga gccaccaaaa gacccgcccc cagtgacgcg    1500
gatataagcg agcccaagcg ggcctgcccc tcagttccgg agccatcgac gtcagacgcg    1560
gaagcaccgg tggactttgc ggacaggtac caaaacaaat gttctcgtca cgcgggcatg    1620
cttcagatgc tgtttccctg caagacatgc gagagaatga atcagaattt caacgtctgc    1680
ttcacgcacg gggtcagaga ctgctcagag tgcttccccg gcgcgtcaga atctcaaccc    1740
gtcgtcagaa aaagacgta tcagaaactg tgcgcgattc atcatctgct ggggcgggca    1800
cccgagattg cgtgttcggc ctgcgatctc gtcaacgtgg acttggatga ctgtgtttct    1860
gagcaataaa tgacttaaac caggtatggc tgctgacggt tatcttccag attggctcga    1920
ggacaacctc tctgagggca ttcgcgagtg gtgggacctg aaacctggag ccccgaagcc    1980
caaggccaac cagcagaagc aggacgacgc ccggggtctg gtgcttcctg gctacaagta    2040
cctcggaccc ttcaacggac tcgacaaggg ggagcccgtc aacgcggcgg acgcagcggc    2100
cctcgagcac gacaaggcct acgaccagca gctcaaagcg ggtgacaatc cgtacctgcg    2160
gtataaccac gccgacgccg agtttcagga gcgtctgcaa gaagatacgt cttttggggg    2220
caacctcggg cgagcagtct tccaggccaa gaagagggta ctcgaacctc tgggcctggt    2280
tgaagaaggt gctaaaacgg ctcctggaaa gaagagaccg ttagagtcac acaagagcc    2340 cgactcctcc tcgggcatcg gcaaaaaagg caaacaacca gccagaaaga ggctcaactt    2400
tgaagaggac actggagccg gagacggacc ccctgaagga tcagatacca gcgccatgtc    2460
ttcagacatt gaaatgcgtg cagcaccggg cggaaatgct gtcgatgcgg gacaaggttc    2520
```

```
cgatggagtg ggtaatgcct cgggtgattg gcattgcgat tccacctggt ctgagggcaa    2580
ggtcacaaca acctcgacca gaacctgggt cttgcccacc tacaacaacc acttgtacct    2640
gcgtctcgga acaacatcaa gcagcaacac ctacaacgga ttctccaccc cctggggata    2700
ttttgacttc aacagattcc actgtcactt ctcaccacgt gactggcaaa gactcatcaa    2760
caacaactgg ggactacgac caaaagccat gcgcgttaaa atcttcaata tccaagttaa    2820
ggaggtcaca acgtcgaacg gcgagactac ggtcgctaat aaccttacca gcacggttca    2880
gatatttgcg gactcgtcgt atgagctccc gtacgtgatg gacgctggac aagaggggag    2940
cctgcctcct ttccccaatg acgtgttcat ggtgcctcaa tatggctact gtggcatcgt    3000
gactggcgag aatcagaacc aaacggacag aaacgctttc tactgcctgg agtatttttcc   3060 ttcgcaaatg ttgagaactg gcaacaactt tgaaatggct tacaactttg agaaggtgcc    3120
gttccactca atgtatgctc acagccagag cctggacaga ctgatgaatc ccctcctgga    3180
ccagtacctg tggcacttac agtcgactac ctctggagag actctgaatc aaggcaatgc    3240
agcaaccaca tttggaaaaa tcaggagtgg agactttgcc ttttacagaa gaactggct    3300 gcctgggcct tgtgttaaac agcagagatt ctcaaaaact gccagtcaaa attacaagat    3360
tcctgccagc gggggcaacg ctctgttaaa gtatgacacc cactatacct aaacaaccg    3420 ctggagcaac atcgcgcccg gacctccaat ggccacagcc ggaccttcgg atggggactt    3480
cagtaacgcc cagcttatat tccctggacc atctgttacc ggaaatacaa caacttcagc    3540
caacaatctg ttgtttacat cagaagaaga aattgctgcc accaacccaa gagacacgga    3600
catgtttggc cagattgctg acaataatca gaatgctaca actgctccca taaccggcaa    3660
cgtgactgct atgggagtgc tgcctggcat ggtgtggcaa aacagagaca tttactacca    3720
agggccaatt tgggccaaga tcccacacgc ggacggacat tttcatcctt caccgctgat    3780
tggtgggttt ggactgaaac acccgcctcc ccagatattc atcaagaaca ctcccgtacc    3840
tgccaatcct gcgacaacct tcactgcagc cagagtggac tctttcatca cacaatacag    3900
caccggccag gtcgctgttc agattgaatg ggaaattgaa aaggaacgct ccaaacgctg    3960
gaatcctgaa gtgcagttta cttcaaacta tgggaaccag tcttctatgt tgtgggctcc    4020
tgatacaact gggaagtata cagagccgcg ggttattggc tctcgttatt tgactaatca    4080
tttgtaa                                                              4087

<210> SEQ ID NO 20
<211> LENGTH: 4213
<212> TYPE: DNA
<213> ORGANISM: Dependoparvovirus Adeno-associated virus - 12

<400> SEQUENCE: 20
ttgcgacagt ttgcgacacc atgtggtcac aagaggtata taaccgcgag tgagccagcg     60
aggagctcca ttttgcccgc gaagtttgaa cgagcagcag ccatgccggg gttctacgag    120
gtggtgatca aggtgcccag cgacctggac gagcacctgc ccggcatttc tgactccttt    180
gtgaactggg tggccgagaa ggaatgggag ttgccccgg attctgacat ggatcagaat    240
ctgattgagc aggcacccct gaccgtggcc gagaagctgc agcgcgagtt cctggtggaa    300
tggcgccgag tgagtaaatt tctggaggcc aagttttttg tgcagtttga aaggggggac    360
tcgtactttc atttgcatat tctgattgaa attaccggcg tgaaatccat ggtggtgggc    420
cgctacgtga gtcagattag ggataaactg atccagcgca tctaccgcgg ggtcgagccc    480
cagctgccca actggttcgc ggtcacaaag acccgaaatg gcgccggagg cgggaacaag    540
```

```
gtggtggacg agtgctacat ccccaactac ctgctcccca aggtccagcc cgagcttcag    600
tgggcgtgga ctaacatgga ggagtatata agcgcctgtt tgaacctcgc ggagcgtaaa    660
cggctcgtgg cgcagcacct gacgcacgtc tcccagaccc aggagggcga caaggagaat    720
ctgaacccga attctgacgc gccggtgatc cggtcaaaaa cctccgccag gtacatggag    780
ctggtcgggt ggctggtgga caagggcatc acgtccgaga agcagtggat ccaggaggac    840
caggcctcgt acatctcctt caacgcggcc tccaactccc ggtcgcagat caaggcggcc    900
ctggacaatg cctccaaaat catgagcctc accaaaacgg ctccggacta tctcatcggg    960
cagcagcccg tggggacat taccaccaac cggatctaca aaatcctgga actgaacggg   1020 tacgacccc agtacgccgc ctccgtcttt ctcggctggg cccagaaaaa gtttggaaag   1080
cgcaacacca tctggctgtt tgggcccgcc accaccggca agaccaacat cgcggaagcc   1140
atcgcccacg cggtccccct ctacggctgc gtcaactgga ccaatgagaa ctttcccttc   1200
aacgactgcg tcgacaaaat ggtgatttgg tgggaggagg gcaagatgac cgccaaggtc   1260
gtagagtccg ccaaggccat tctgggcggc agcaaggtgc gcgtggacca aaaatgcaag   1320
gcctctgcgc agatcgaccc cacccccgtg atcgtcacct ccaacaccaa catgtgcgcc   1380
gtgattgacg ggaacagcac caccttcgag caccagcagc cctgcagga ccggatgttc   1440 aagtttgaac tcacccgccg cctcgaccac gactttggca aggtcaccaa gcaggaagtc   1500
aaggactttt tccggtgggc ggctgatcac gtgactgacg tggctcatga gttttacgtc   1560
acaaagggtg gagctaagaa aaggcccgcc ccctctgacg aggatataag cgagcccaag   1620
cggccgcgcg tgtcatttgc gcagccggag acgtcagacg cggaagctcc cggagacttc   1680
gccgacaggt accaaaacaa atgttctcgt cacgcgggta tgctgcagat gctctttccc   1740
tgcaagacgt gcgagagaat gaatcagaat tccaacgtct gcttcacgca cggtcagaaa   1800
gattgcgggg agtgctttcc cgggtcagaa tctcaaccgg tttctgtcgt cagaaaaacg   1860
tatcagaaac tgtgcatcct tcatcagctc cgggggggcac ccgagatcgc ctgctctgct   1920
tgcgaccaac tcaaccccga tttggacgat tgccaatttg agcaataaat gactgaaatc   1980
aggtatggct gctgacggtt atcttccaga ttggctcgag gacaacctct ctgaaggcat   2040
tcgcgagtgg tgggcgctga aacctggagc tccacaaccc aaggccaacc aacagcatca   2100
ggacaacggc aggggtcttg tgcttcctgg gtacaagtac ctcggaccct tcaacgact   2160 cgacaaggga gagccggtca acgaggcaga cgccgcggcc ctcgagcacg acaaggccta   2220
cgacaagcag ctcgagcagg gggacaaccc gtatctcaag tacaaccacg ccgacgccga   2280
gttccagcag cgcttggcga ccgacacctc ttttgggggc aacctcgggc gagcagtctt   2340
ccaggccaaa aagaggattc tcgagcctct gggtctggtt gaagagggcg ttaaaacggc   2400
tcctggaaag aaacgcccat tagaaaagac tccaaatcgg ccgaccaacc cggactctgg   2460
gaaggccccg ccaagaaaaa agcaaaaaga cggcgaacca gccgactctg ctagaaggac   2520
actcgacttt gaagactctg gagcaggaga cggaccccct gagggatcat cttccggaga   2580
aatgtctcat gatgctgaga tgcgtgcggc gccaggcgga aatgctgtcg aggcgggaca   2640
aggtgccgat ggagtgggta atgcctccgg tgattggcat tgcgattcca cctggtcaga   2700
gggccgagtc accaccacca gcacccgaac ctgggtccta cccacgtaca acaaccacct   2760
gtacctgcga atcggaacaa cggccaacag caacacctac aacggattct ccaccccctg   2820
gggatacttt gactttaacc gcttccactg ccacttttcc ccacgcgact ggcagcgact   2880
```

-continued

```
catcaacaac aactggggac tcaggccgaa atcgatgcgt gttaaaatct tcaacataca    2940
ggtcaaggag gtcacgacgt caaacggcga gactacggtc gctaataacc ttaccagcac    3000
ggttcagatc tttgcggatt cgacgtatga actcccatac gtgatggacg ccggtcagga    3060
ggggagcttt cctccgtttc caacgacgt ctttatggtt ccccaatacg atactgcgg     3120 agttgtcact ggaaaaaacc agaaccagac agacagaaat gccttttact gcctggaata    3180
ctttccatcc caaatgctaa gaactggcaa caattttgaa gtcagttacc aatttgaaaa    3240
agttcctttc cattcaatgt acgcgcacag ccagagcctg gacagaatga tgaatccttt    3300
actggatcag tacctgtggc atctgcaatc gaccactacc ggaaattccc ttaatcaagg    3360
aacagctacc accacgtacg ggaaaattac cactggagac tttgcctact acaggaaaaa    3420
ctggttgcct ggagcctgca ttaaacaaca aaaattttca aagaatgcca atcaaaacta    3480
caagattccc gccagcgggg gagacgccct tttaaagtat gacacgcata ccactctaaa    3540
tgggcgatgg agtaacatgg ctcctggacc tccaatggca accgcaggtg ccggggactc    3600
ggattttagc aacagccagc tgatctttgc cggacccaat ccgagcggta acacgaccac    3660
atcttcaaac aatttgttgt ttacctcaga agaggagatt gccacaacaa cccacgaga    3720 cacggacatg tttggacaga ttgcagataa taatcaaaat gccaccaccg cccctcacat    3780
cgctaacctg gacgctatgg gaattgttcc cggaatggtc tggcaaaaca gagacatcta    3840
ctaccagggc cctatttggg ccaaggtccc tcacacggac ggcactttc acccttcgcc    3900 gctgatggga ggatttggac tgaaacaccc gcctccacag attttcatca aaaacacccc    3960
cgtacccgcc aatcccaata ctaccttag cgctgcaagg attaattctt ttctgacgca    4020
gtacagcacc ggacaagttg ccgttcagat cgactgggaa attcagaagg agcattccaa    4080
acgctggaat cccgaagttc aatttacttc aaactacggc actcaaaatt ctatgctgtg    4140
ggctcccgac aatgctggca actaccacga actccgggct attgggtccc gtttcctcac    4200
ccaccacttg taa                                                       4213
```

<210> SEQ ID NO 21
<211> LENGTH: 623
<212> TYPE: PRT
<213> ORGANISM: Dependoparvovirus Adeno-associated virus - 1

<400> SEQUENCE: 21

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
```

```
            130                 135                 140
Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ala
        275                 280                 285

Pro Pro Ala Asp Ile Lys Thr Asn Arg Ile Tyr Arg Ile Leu Glu Leu
    290                 295                 300

Asn Gly Tyr Glu Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
    450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Leu Gln Met
    530                 535                 540

Leu Phe Pro Cys Lys Thr Cys Glu Arg Met Asn Gln Asn Phe Asn Ile
545                 550                 555                 560
```

```
Cys Phe Thr His Gly Thr Arg Asp Cys Ser Glu Cys Phe Pro Gly Val
                565                 570                 575

Ser Glu Ser Gln Pro Val Val Arg Lys Arg Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
    610                 615                 620
```

<210> SEQ ID NO 22
<211> LENGTH: 536
<212> TYPE: PRT
<213> ORGANISM: Dependoparvovirus Adeno-associated virus - 2

<400> SEQUENCE: 22

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
```

```
                305                 310                 315                 320
Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
                340                 345                 350

Phe Tyr Gly Cys Val Asn Trp Thr Asn Glu Asn Phe Pro Phe Asn Asp
                355                 360                 365

Cys Val Asp Lys Met Val Ile Trp Trp Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
            450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
                500                 505                 510

Ala Gln Pro Ser Thr Ser Asp Ala Glu Ala Ser Ile Asn Tyr Ala Asp
            515                 520                 525

Arg Leu Ala Arg Gly His Ser Leu
            530                 535

<210> SEQ ID NO 23
<211> LENGTH: 621
<212> TYPE: PRT
<213> ORGANISM: Dependoparvovirus Adeno-associated virus - 2

<400> SEQUENCE: 23

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
        50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
        130                 135                 140
```

```
Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
            165                 170                 175

Ser Ala Cys Leu Asn Leu Thr Glu Arg Lys Arg Leu Val Ala Gln His
        180                 185                 190

Leu Thr His Val Ser Gln Thr Gln Glu Gln Asn Lys Glu Asn Gln Asn
    195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
```

565                 570                 575
Ser Gln Pro Val Ser Val Lys Lys Ala Tyr Gln Lys Leu Cys Tyr
            580                 585                 590

Ile His His Ile Met Gly Lys Val Pro Asp Ala Cys Thr Ala Cys Asp
            595                 600                 605

Leu Val Asn Val Asp Leu Asp Cys Ile Phe Glu Gln
            610                 615                 620

<210> SEQ ID NO 24
<211> LENGTH: 312
<212> TYPE: PRT
<213> ORGANISM: Dependoparvovirus Adeno-associated virus - 2

<400> SEQUENCE: 24

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
    290                 295                 300

Arg Leu Ala Arg Gly His Ser Leu
305                 310

<210> SEQ ID NO 25
<211> LENGTH: 397
<212> TYPE: PRT
<213> ORGANISM: Dependoparvovirus Adeno-associated virus - 2

<400> SEQUENCE: 25

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
    290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Ser Asn Ile Cys
                325                 330                 335

Phe Thr His Gly Gln Lys Asp Cys Leu Glu Cys Phe Pro Val Ser Glu
            340                 345                 350

Ser Gln Pro Val Ser Val Val Lys Lys Ala Tyr Gln Lys Leu Cys Tyr
        355                 360                 365

Ile His His Ile Met Gly Lys Val Pro Asp Ala Cys Thr Ala Cys Asp
    370                 375                 380

```
Leu Val Asn Val Asp Leu Asp Asp Cys Ile Phe Glu Gln
385                 390                 395
```

<210> SEQ ID NO 26
<211> LENGTH: 624
<212> TYPE: PRT
<213> ORGANISM: Dependoparvovirus Adeno-associated virus - 3

<400> SEQUENCE: 26

```
Met Pro Gly Phe Tyr Glu Ile Val Leu Lys Val Pro Ser Asp Leu Asp
1               5                   10                  15

Glu His Leu Pro Gly Ile Ser Asn Ser Phe Val Asn Trp Val Ala Glu
                20                  25                  30

Lys Glu Trp Glu Leu Pro Pro Asp Ser Asp Met Asp Pro Asn Leu Ile
            35                  40                  45

Glu Gln Ala Pro Leu Thr Val Ala Glu Lys Leu Gln Arg Glu Phe Leu
        50                  55                  60

Val Glu Trp Arg Arg Val Ser Lys Ala Pro Glu Ala Leu Phe Phe Val
65                  70                  75                  80

Gln Phe Glu Lys Gly Glu Thr Tyr Phe His Leu His Val Leu Ile Glu
                85                  90                  95

Thr Ile Gly Val Lys Ser Met Val Val Gly Arg Tyr Val Ser Gln Ile
                100                 105                 110

Lys Glu Lys Leu Val Thr Arg Ile Tyr Arg Gly Val Glu Pro Gln Leu
            115                 120                 125

Pro Asn Trp Phe Ala Val Thr Lys Thr Arg Asn Gly Ala Gly Gly Gly
130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
                260                 265                 270

Ile Met Ser Leu Thr Lys Thr Ala Pro Asp Tyr Leu Val Gly Ser Asn
            275                 280                 285

Pro Pro Glu Asp Ile Thr Lys Asn Arg Ile Tyr Gln Ile Leu Glu Leu
290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
                340                 345                 350

Phe Tyr Gly Cys Val Asn Trp Thr Asn Glu Asn Phe Pro Phe Asn Asp
```

```
              355                 360                 365
Cys Val Asp Lys Met Val Ile Trp Trp Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Gln Cys Thr Ser Leu
            500                 505                 510

Ala Gln Pro Thr Thr Ser Asp Ala Glu Ala Pro Ala Asp Tyr Ala Asp
        515                 520                 525

Arg Tyr Gln Asn Lys Cys Ser Arg His Val Gly Met Asn Leu Met Leu
    530                 535                 540

Phe Pro Cys Lys Thr Cys Glu Arg Met Asn Gln Ile Ser Asn Val Cys
545                 550                 555                 560

Phe Thr His Gly Gln Arg Asp Cys Gly Glu Cys Phe Pro Gly Met Ser
                565                 570                 575

Glu Ser Gln Pro Val Ser Val Val Lys Lys Thr Tyr Gln Lys Leu
            580                 585                 590

Cys Pro Ile His His Ile Leu Gly Arg Ala Pro Glu Ile Ala Cys Ser
        595                 600                 605

Ala Cys Asp Leu Ala Asn Val Asp Leu Asp Asp Cys Val Ser Glu Gln
    610                 615                 620

<210> SEQ ID NO 27
<211> LENGTH: 623
<212> TYPE: PRT
<213> ORGANISM: Dependoparvovirus Adeno-associated virus - 4

<400> SEQUENCE: 27

Met Pro Gly Phe Tyr Glu Ile Val Leu Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Glu Phe Leu
    50                  55                  60

Val Glu Trp Arg Arg Val Ser Lys Ala Pro Glu Ala Leu Phe Phe Val
65                  70                  75                  80

Gln Phe Glu Lys Gly Asp Ser Tyr Phe His Leu His Ile Leu Val Glu
                85                  90                  95

Thr Val Gly Val Lys Ser Met Val Val Gly Arg Tyr Val Ser Gln Ile
            100                 105                 110
```

```
Lys Glu Lys Leu Val Thr Arg Ile Tyr Arg Gly Val Glu Pro Gln Leu
            115                 120                 125

Pro Asn Trp Phe Ala Val Thr Lys Thr Arg Asn Gly Ala Gly Gly Gly
130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Val Gly Gln Asn
        275                 280                 285

Pro Pro Glu Asp Ile Ser Ser Asn Arg Ile Tyr Arg Ile Leu Glu Met
290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Lys Arg Leu Glu His Asp Phe Gly Lys Val Thr Lys Gln
        450                 455                 460

Glu Val Lys Asp Phe Phe Arg Trp Ala Ser Asp His Val Thr Glu Val
465                 470                 475                 480

Thr His Glu Phe Tyr Val Arg Lys Gly Gly Ala Arg Lys Arg Pro Ala
                485                 490                 495

Pro Asn Asp Ala Asp Ile Ser Glu Pro Lys Arg Ala Cys Pro Ser Val
            500                 505                 510

Ala Gln Pro Ser Thr Ser Asp Ala Glu Ala Pro Val Asp Tyr Ala Asp
        515                 520                 525

Arg Tyr Gln Asn Lys Cys Ser Arg His Val Gly Met Asn Leu Met Leu
```

```
                530             535             540
Phe Pro Cys Arg Gln Cys Glu Arg Met Asn Gln Asn Val Asp Ile Cys
545                 550                 555                 560

Phe Thr His Gly Val Met Asp Cys Ala Glu Cys Phe Pro Val Ser Glu
                565                 570                 575

Ser Gln Pro Val Ser Val Val Arg Lys Arg Thr Tyr Gln Lys Leu Cys
                580                 585                 590

Pro Ile His His Ile Met Gly Arg Ala Pro Glu Val Ala Cys Ser Ala
                595                 600                 605

Cys Glu Leu Ala Asn Val Asp Leu Asp Asp Cys Asp Met Glu Gln
                610                 615                 620

<210> SEQ ID NO 28
<211> LENGTH: 734
<212> TYPE: PRT
<213> ORGANISM: Dependoparvovirus Adeno-associated virus - 4

<400> SEQUENCE: 28

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
                20                  25                  30

Ala Asn Gln Gln His Gln Asp Asn Ala Arg Gly Leu Val Leu Pro Gly
                35                  40                  45

Tyr Lys Tyr Leu Gly Pro Gly Asn Gly Leu Asp Lys Gly Glu Pro Val
            50                  55                  60

Asn Ala Ala Asp Ala Ala Ala Leu Glu His Asp Lys Ala Tyr Asp Gln
65              70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
                100                 105                 110

Leu Gly Arg Ala Val Phe Gln Ala Lys Lys Arg Val Leu Glu Pro Leu
            115                 120                 125

Gly Leu Val Glu Gln Ala Gly Glu Thr Ala Pro Gly Lys Lys Arg Pro
            130                 135                 140

Leu Ile Glu Ser Pro Gln Gln Pro Asp Ser Ser Thr Gly Ile Gly Lys
145             150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
                180                 185                 190

Asp Asp Ser Glu Met Arg Ala Ala Ala Gly Gly Ala Ala Val Glu Gly
                195                 200                 205

Gly Gln Gly Ala Asp Gly Val Gly Asn Ala Ser Gly Asp Trp His Cys
            210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
                260                 265                 270

Phe Asp Phe Asn Arg Phe His Cys His Phe Ser Pro Arg Asp Trp Gln
                275                 280                 285
```

```
Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
        675                 680                 685

Arg Ser Lys Arg Trp Asn Pro Glu Val Gln Phe Thr Ser Asn Tyr Gly
690                 695                 700

Gln Gln Asn Ser Leu Leu Trp Ala Pro Asp Ala Ala Gly Lys Tyr Thr
```

```
                705                 710                 715                 720
Glu Pro Arg Ala Ile Gly Thr Arg Tyr Leu Thr His His Leu
                    725                 730

<210> SEQ ID NO 29
<211> LENGTH: 610
<212> TYPE: PRT
<213> ORGANISM: Dependoparvovirus Adeno-associated virus - 5

<400> SEQUENCE: 29

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Phe Gln Gly Ile Glu Pro Gln Ile Asn
        115                 120                 125

Asp Trp Val Ala Ile Thr Lys Val Lys Lys Gly Gly Ala Asn Lys Val
130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
        195                 200                 205

Asp Pro Val Ile Lys Ser Lys Thr Ser Gln Lys Tyr Met Ala Leu Val
210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
        275                 280                 285

Ile Ser Lys Asn Arg Ile Trp Gln Ile Phe Glu Met Asn Gly Tyr Asp
    290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
                325                 330                 335

Thr Asn Ile Ala Glu Ala Ile Ala His Thr Val Pro Phe Tyr Gly Cys
            340                 345                 350
```

Val Asn Trp Thr Asn Glu Asn Phe Pro Phe Asn Asp Cys Val Asp Lys
            355                 360                 365

Met Leu Ile Trp Trp Glu Glu Gly Lys Met Thr Asn Lys Val Val Glu
    370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Asp Gly Asn Ser Thr Thr Phe Glu
            420                 425                 430

His Gln Gln Pro Leu Glu Asp Arg Met Phe Lys Phe Glu Leu Thr Lys
    435                 440                 445

Arg Leu Pro Pro Asp Phe Gly Lys Ile Thr Lys Gln Glu Val Lys Asp
    450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
                485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
    515                 520                 525

Val Thr Val Asp Pro Ala Pro Leu Arg Pro Leu Asn Trp Asn Ser Arg
    530                 535                 540

Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
                565                 570                 575

Cys His Asn Val Thr His Cys Gln Ile Cys His Gly Ile Pro Pro Trp
            580                 585                 590

Glu Lys Glu Asn Leu Ser Asp Phe Gly Asp Phe Asp Asp Ala Asn Lys
    595                 600                 605

Glu Gln
    610

<210> SEQ ID NO 30
<211> LENGTH: 623
<212> TYPE: PRT
<213> ORGANISM: Dependoparvovirus Adeno-associated virus - 6

<400> SEQUENCE: 30

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

```
Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala His Asp
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ala
        275                 280                 285

Pro Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
    450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525
```

```
Asp Arg Tyr Gln Asn Lys Cys Ser Arg His Ala Gly Met Leu Gln Met
            530                 535                 540

Leu Phe Pro Cys Lys Thr Cys Glu Arg Met Asn Gln Asn Phe Asn Ile
545                 550                 555                 560

Cys Phe Thr His Gly Thr Arg Asp Cys Ser Glu Cys Phe Pro Gly Val
                565                 570                 575

Ser Glu Ser Gln Pro Val Val Arg Lys Arg Thr Tyr Arg Lys Leu Cys
            580                 585                 590

Ala Ile His His Leu Leu Gly Arg Ala Pro Glu Ile Ala Cys Ser Ala
            595                 600                 605

Cys Asp Leu Val Asn Val Asp Leu Asp Asp Cys Val Ser Glu Gln
610                 615                 620

<210> SEQ ID NO 31
<211> LENGTH: 623
<212> TYPE: PRT
<213> ORGANISM: Dependoparvovirus Adeno-associated virus - 7

<400> SEQUENCE: 31

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Gln Thr Ile Tyr Arg Gly Val Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285
```

Leu Pro Ala Asp Ile Lys Thr Asn Arg Ile Tyr Arg Ile Leu Glu Leu
        290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
                485                 490                 495

Pro Asp Asp Ala Asp Ile Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Ile Gln Met
530                 535                 540

Leu Phe Pro Cys Lys Thr Cys Glu Arg Met Asn Gln Asn Phe Asn Ile
545                 550                 555                 560

Cys Phe Thr His Gly Val Arg Asp Cys Leu Glu Cys Phe Pro Gly Val
                565                 570                 575

Ser Glu Ser Gln Pro Val Val Arg Lys Lys Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
610                 615                 620

<210> SEQ ID NO 32
<211> LENGTH: 624
<212> TYPE: PRT
<213> ORGANISM: Dependoparvovirus Adeno-associated virus - 8

<400> SEQUENCE: 32

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile

```
                35                  40                  45
Glu Gln Ala Pro Leu Thr Val Ala Glu Lys Leu Gln Arg Asp Phe Leu
 50                  55                  60
Val Gln Trp Arg Arg Val Ser Lys Ala Pro Glu Ala Leu Phe Phe Val
 65                  70                  75                  80
Gln Phe Glu Lys Gly Glu Ser Tyr Phe His Leu His Val Leu Val Glu
                     85                  90                  95
Thr Thr Gly Val Lys Ser Met Val Leu Gly Arg Phe Leu Ser Gln Ile
            100                 105                 110
Arg Glu Lys Leu Gly Pro Asp His Leu Pro Ala Gly Ser Ser Pro Thr
        115                 120                 125
Leu Pro Asn Trp Phe Ala Val Thr Lys Asp Ala Val Met Ala Pro Ala
    130                 135                 140
Gly Gly Asn Lys Val Val Asp Glu Cys Tyr Ile Pro Asn Tyr Leu Leu
145                 150                 155                 160
Pro Lys Thr Gln Pro Glu Leu Gln Trp Ala Trp Thr Asn Met Glu Glu
                    165                 170                 175
Tyr Ile Ser Ala Cys Leu Asn Leu Ala Glu Arg Lys Arg Leu Val Ala
            180                 185                 190
Gln His Leu Thr His Val Ser Gln Thr Gln Glu Gln Asn Lys Glu Asn
        195                 200                 205
Leu Asn Pro Asn Ser Asp Ala Pro Val Ile Arg Ser Lys Thr Ser Ala
    210                 215                 220
Arg Tyr Met Glu Leu Val Gly Trp Leu Val Asp Arg Gly Ile Thr Ser
225                 230                 235                 240
Glu Lys Gln Trp Ile Gln Glu Asp Gln Ala Ser Tyr Ile Ser Phe Asn
                    245                 250                 255
Ala Ala Ser Asn Ser Arg Ser Gln Ile Lys Ala Ala Leu Asp Asn Ala
            260                 265                 270
Gly Lys Ile Met Ala Leu Thr Lys Ser Ala Pro Asp Tyr Leu Val Gly
        275                 280                 285
Pro Ser Leu Pro Ala Asp Ile Thr Gln Asn Arg Ile Tyr Arg Ile Leu
    290                 295                 300
Ala Leu Asn Gly Tyr Asp Pro Ala Tyr Ala Gly Ser Val Phe Leu Gly
305                 310                 315                 320
Trp Ala Gln Lys Lys Phe Gly Lys Arg Asn Thr Ile Trp Leu Phe Gly
                    325                 330                 335
Pro Ala Thr Thr Gly Lys Thr Asn Ile Ala Glu Ala Ile Ala His Ala
            340                 345                 350
Val Pro Phe Tyr Gly Cys Val Asn Trp Thr Asn Glu Asn Phe Pro Phe
        355                 360                 365
Asn Asp Cys Val Asp Lys Met Val Ile Trp Trp Glu Glu Gly Lys Met
    370                 375                 380
Thr Ala Lys Val Val Glu Ser Ala Lys Ala Ile Leu Gly Gly Ser Lys
385                 390                 395                 400
Val Arg Val Asp Gln Lys Cys Lys Ser Ser Ala Gln Ile Asp Pro Thr
                    405                 410                 415
Pro Val Ile Val Thr Ser Asn Thr Asn Met Cys Ala Val Ile Asp Gly
            420                 425                 430
Asn Ser Thr Thr Phe Glu His Gln Gln Pro Leu Gln Asp Arg Met Phe
        435                 440                 445
Lys Phe Glu Leu Thr Arg Arg Leu Glu His Asp Phe Gly Lys Val Thr
    450                 455                 460
```

```
Lys Gln Glu Val Lys Glu Phe Phe Arg Trp Ala Ser Asp His Val Thr
465                 470                 475                 480

Glu Val Ala His Glu Phe Tyr Val Arg Lys Gly Gly Ala Ser Lys Arg
                485                 490                 495

Pro Ala Pro Asp Asp Ala Asp Lys Ser Glu Pro Lys Arg Ala Cys Pro
            500                 505                 510

Ser Val Ala Asp Pro Ser Thr Ser Asp Ala Glu Gly Ala Pro Val Asp
            515                 520                 525

Phe Ala Asp Arg Tyr Gln Asn Lys Cys Ser Arg His Ala Gly Met Leu
530                 535                 540

Gln Met Leu Phe Pro Cys Lys Thr Cys Glu Arg Met Asn Gln Asn Phe
545                 550                 555                 560

Asn Ile Cys Phe Thr His Gly Val Arg Asp Cys Ser Glu Cys Phe Pro
                565                 570                 575

Gly Val Ser Glu Ser Gln Pro Val Val Arg Lys Arg Thr Tyr Arg Lys
            580                 585                 590

Leu Cys Ala Ile His His Leu Gly Arg Ala Pro Glu Ile Ala Cys
                595                 600                 605

Ser Ala Cys Asp Leu Val Asn Val Asp Leu Asp Cys Val Ser Glu
            610                 615                 620

<210> SEQ ID NO 33
<211> LENGTH: 622
<212> TYPE: PRT
<213> ORGANISM: Dependoparvovirus Adeno-associated virus - 10

<400> SEQUENCE: 33

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Arg Asn Leu Ile
            35                  40                  45

Glu Gln Ala Pro Leu Thr Val Ala Glu Lys Leu Gln Arg Asp Phe Leu
50                  55                  60

Val His Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Asp Arg Leu Val Gln Thr Ile Tyr Arg Gly Val Glu Pro Thr Leu
            115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
            195                 200                 205

Pro Asn Ser Asp Ala Pro Val Ile Arg Ser Lys Thr Ser Ala Arg Tyr
```

```
                 210                 215                 220
    Met Glu Leu Val Gly Trp Leu Val Asp Arg Gly Ile Thr Ser Glu Lys
    225                 230                 235                 240

Gln Trp Ile Gln Glu Asp Gln Ala Ser Tyr Ile Ser Phe Asn Ala Ala
                    245                 250                 255

Ser Asn Ser Arg Ser Gln Ile Lys Ala Ala Leu Asp Asn Ala Gly Lys
                260                 265                 270

Ile Met Ala Leu Thr Lys Ser Ala Pro Asp Tyr Leu Val Gly Pro Ser
                275                 280                 285

Leu Pro Ala Asp Ile Lys Ala Asn Arg Ile Tyr Arg Ile Leu Glu Leu
    290                 295                 300

Asn Gly Tyr Asp Pro Ala Tyr Ala Gly Ser Val Phe Leu Gly Trp Ala
    305                 310                 315                 320

Gln Lys Lys Phe Gly Lys Arg Asn Thr Ile Trp Leu Phe Gly Pro Ala
                    325                 330                 335

Thr Thr Gly Lys Thr Asn Ile Ala Glu Ala Ile Ala His Ala Val Pro
                340                 345                 350

Phe Tyr Gly Cys Val Asn Trp Thr Asn Glu Asn Phe Pro Phe Asn Asp
                355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
    385                 390                 395                 400

Val Asp Gln Lys Cys Lys Ser Ser Ala Gln Ile Asp Pro Thr Pro Val
                    405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
                435                 440                 445

Glu Leu Thr Arg Arg Leu Glu His Asp Phe Gly Lys Val Thr Lys Gln
    450                 455                 460

Glu Val Lys Glu Phe Phe Arg Trp Ala Gln Asp His Val Thr Glu Val
    465                 470                 475                 480

Thr His Glu Phe Tyr Val Arg Lys Gly Gly Ala Thr Lys Arg Pro Ala
                    485                 490                 495

Pro Ser Asp Ala Asp Ile Ser Glu Pro Lys Arg Ala Cys Pro Ser Val
                500                 505                 510

Ala Glu Pro Ser Thr Ser Asp Ala Glu Ala Pro Val Asp Phe Ala Asp
                515                 520                 525

Arg Tyr Gln Asn Lys Cys Ser Arg His Ala Gly Met Leu Gln Met Leu
    530                 535                 540

Phe Pro Cys Lys Thr Cys Glu Arg Met Asn Gln Asn Phe Asn Val Cys
    545                 550                 555                 560

Phe Thr His Gly Val Arg Asp Cys Ser Glu Cys Phe Pro Gly Ala Ser
                    565                 570                 575

Glu Ser Gln Pro Val Val Arg Lys Lys Thr Tyr Gln Lys Leu Cys Ala
                580                 585                 590

Ile His His Leu Leu Gly Arg Ala Pro Glu Ile Ala Cys Ser Ala Cys
                595                 600                 605

Asp Leu Val Asn Val Asp Leu Asp Cys Val Ser Glu Gln
                610                 615                 620

<210> SEQ ID NO 34
```

```
<211> LENGTH: 622
<212> TYPE: PRT
<213> ORGANISM: Dependoparvovirus Adeno-associated virus - 11

<400> SEQUENCE: 34
```

| | | | | | | | | | | | | | | |
|---|---|---|---|---|---|---|---|---|---|---|---|---|---|---|
| Met | Pro | Gly | Phe | Tyr | Glu | Ile | Val | Ile | Lys | Val | Pro | Ser | Asp | Leu | Asp |
| 1 | | | | 5 | | | | | 10 | | | | | 15 | |

| Glu | His | Leu | Pro | Gly | Ile | Ser | Asp | Ser | Phe | Val | Asn | Trp | Val | Ala | Glu |
|---|---|---|---|---|---|---|---|---|---|---|---|---|---|---|---|
| | | | 20 | | | | | 25 | | | | | 30 | | |

| Lys | Glu | Trp | Glu | Leu | Pro | Pro | Asp | Ser | Asp | Met | Asp | Arg | Asn | Leu | Ile |
|---|---|---|---|---|---|---|---|---|---|---|---|---|---|---|---|
| | | | 35 | | | | | 40 | | | | | 45 | | |

| Glu | Gln | Ala | Pro | Leu | Thr | Val | Ala | Glu | Lys | Leu | Gln | Arg | Asp | Phe | Leu |
|---|---|---|---|---|---|---|---|---|---|---|---|---|---|---|---|
| | 50 | | | | | 55 | | | | | 60 | | | | |

| Val | His | Trp | Arg | Arg | Val | Ser | Lys | Ala | Pro | Glu | Ala | Leu | Phe | Phe | Val |
|---|---|---|---|---|---|---|---|---|---|---|---|---|---|---|---|
| 65 | | | | | 70 | | | | | 75 | | | | | 80 |

| Gln | Phe | Glu | Lys | Gly | Glu | Ser | Tyr | Phe | His | Leu | His | Val | Leu | Val | Glu |
|---|---|---|---|---|---|---|---|---|---|---|---|---|---|---|---|
| | | | | 85 | | | | | 90 | | | | | 95 | |

| Thr | Thr | Gly | Val | Lys | Ser | Met | Val | Leu | Gly | Arg | Phe | Leu | Ser | Gln | Ile |
|---|---|---|---|---|---|---|---|---|---|---|---|---|---|---|---|
| | | | | 100 | | | | | 105 | | | | | 110 | |

| Arg | Asp | Arg | Leu | Val | Gln | Thr | Ile | Tyr | Arg | Gly | Val | Glu | Pro | Thr | Leu |
|---|---|---|---|---|---|---|---|---|---|---|---|---|---|---|---|
| | | 115 | | | | | 120 | | | | | 125 | | | |

| Pro | Asn | Trp | Phe | Ala | Val | Thr | Lys | Thr | Arg | Asn | Gly | Ala | Gly | Gly | Gly |
|---|---|---|---|---|---|---|---|---|---|---|---|---|---|---|---|
| | 130 | | | | | 135 | | | | | 140 | | | | |

| Asn | Lys | Val | Val | Asp | Glu | Cys | Tyr | Ile | Pro | Asn | Tyr | Leu | Leu | Pro | Lys |
|---|---|---|---|---|---|---|---|---|---|---|---|---|---|---|---|
| 145 | | | | | 150 | | | | | 155 | | | | | 160 |

| Thr | Gln | Pro | Glu | Leu | Gln | Trp | Ala | Trp | Thr | Asn | Met | Glu | Glu | Tyr | Ile |
|---|---|---|---|---|---|---|---|---|---|---|---|---|---|---|---|
| | | | | 165 | | | | | 170 | | | | | 175 | |

| Ser | Ala | Cys | Leu | Asn | Leu | Ala | Glu | Arg | Lys | Arg | Leu | Val | Ala | Gln | His |
|---|---|---|---|---|---|---|---|---|---|---|---|---|---|---|---|
| | | | 180 | | | | | 185 | | | | | 190 | | |

| Leu | Thr | His | Val | Ser | Gln | Thr | Gln | Glu | Gln | Asn | Lys | Glu | Asn | Leu | Asn |
|---|---|---|---|---|---|---|---|---|---|---|---|---|---|---|---|
| | | 195 | | | | | 200 | | | | | 205 | | | |

| Pro | Asn | Ser | Asp | Ala | Pro | Val | Ile | Arg | Ser | Lys | Thr | Ser | Ala | Arg | Tyr |
|---|---|---|---|---|---|---|---|---|---|---|---|---|---|---|---|
| | 210 | | | | | 215 | | | | | 220 | | | | |

| Met | Glu | Leu | Val | Gly | Trp | Leu | Val | Asp | Arg | Gly | Ile | Thr | Ser | Glu | Lys |
|---|---|---|---|---|---|---|---|---|---|---|---|---|---|---|---|
| 225 | | | | | 230 | | | | | 235 | | | | | 240 |

| Gln | Trp | Ile | Gln | Glu | Asp | Gln | Ala | Ser | Tyr | Ile | Ser | Phe | Asn | Ala | Ala |
|---|---|---|---|---|---|---|---|---|---|---|---|---|---|---|---|
| | | | | 245 | | | | | 250 | | | | | 255 | |

| Ser | Asn | Ser | Arg | Ser | Gln | Ile | Lys | Ala | Ala | Leu | Asp | Asn | Ala | Gly | Lys |
|---|---|---|---|---|---|---|---|---|---|---|---|---|---|---|---|
| | | | 260 | | | | | 265 | | | | | 270 | | |

| Ile | Met | Ala | Leu | Thr | Lys | Ser | Ala | Pro | Asp | Tyr | Leu | Val | Gly | Pro | Ser |
|---|---|---|---|---|---|---|---|---|---|---|---|---|---|---|---|
| | | 275 | | | | | 280 | | | | | 285 | | | |

| Leu | Pro | Ala | Asp | Ile | Lys | Ala | Asn | Arg | Ile | Tyr | Arg | Ile | Leu | Glu | Leu |
|---|---|---|---|---|---|---|---|---|---|---|---|---|---|---|---|
| | 290 | | | | | 295 | | | | | 300 | | | | |

| Asn | Gly | Tyr | Asp | Pro | Ala | Tyr | Ala | Gly | Ser | Val | Phe | Leu | Gly | Trp | Ala |
|---|---|---|---|---|---|---|---|---|---|---|---|---|---|---|---|
| 305 | | | | | 310 | | | | | 315 | | | | | 320 |

| Gln | Lys | Lys | Phe | Gly | Lys | Arg | Asn | Thr | Ile | Trp | Leu | Phe | Gly | Pro | Ala |
|---|---|---|---|---|---|---|---|---|---|---|---|---|---|---|---|
| | | | | 325 | | | | | 330 | | | | | 335 | |

| Thr | Thr | Gly | Lys | Thr | Asn | Ile | Ala | Glu | Ala | Ile | Ala | His | Ala | Val | Pro |
|---|---|---|---|---|---|---|---|---|---|---|---|---|---|---|---|
| | | | | 340 | | | | | 345 | | | | | 350 | |

| Phe | Tyr | Gly | Cys | Val | Asn | Trp | Thr | Asn | Glu | Asn | Phe | Pro | Phe | Asn | Asp |
|---|---|---|---|---|---|---|---|---|---|---|---|---|---|---|---|
| | | | 355 | | | | | 360 | | | | | 365 | | |

| Cys | Val | Asp | Lys | Met | Val | Ile | Trp | Trp | Glu | Glu | Gly | Lys | Met | Thr | Ala |
|---|---|---|---|---|---|---|---|---|---|---|---|---|---|---|---|
| | | 370 | | | | | 375 | | | | | 380 | | | |

| Lys | Val | Val | Glu | Ser | Ala | Lys | Ala | Ile | Leu | Gly | Gly | Ser | Lys | Val | Arg |

```
            385                 390                 395                 400
Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
                435                 440                 445

Glu Leu Thr Arg Arg Leu Glu His Asp Phe Gly Lys Val Thr Lys Gln
            450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Thr Lys Arg Pro Ala
                485                 490                 495

Pro Ser Asp Ala Asp Ile Ser Glu Pro Lys Arg Ala Cys Pro Ser Val
                500                 505                 510

Pro Glu Pro Ser Thr Ser Asp Ala Glu Ala Pro Val Asp Phe Ala Asp
            515                 520                 525

Arg Tyr Gln Asn Lys Cys Ser Arg His Ala Gly Met Leu Gln Met Leu
    530                 535                 540

Phe Pro Cys Lys Thr Cys Glu Arg Met Asn Gln Asn Phe Asn Val Cys
545                 550                 555                 560

Phe Thr His Gly Val Arg Asp Cys Ser Glu Cys Phe Pro Gly Ala Ser
                565                 570                 575

Glu Ser Gln Pro Val Val Arg Lys Lys Thr Tyr Gln Lys Leu Cys Ala
                580                 585                 590

Ile His His Leu Leu Gly Arg Ala Pro Glu Ile Ala Cys Ser Ala Cys
        595                 600                 605

Asp Leu Val Asn Val Asp Leu Asp Cys Val Ser Glu Gln
    610                 615                 620

<210> SEQ ID NO 35
<211> LENGTH: 621
<212> TYPE: PRT
<213> ORGANISM: Dependoparvovirus Adeno-associated virus - 12

<400> SEQUENCE: 35

Met Pro Gly Phe Tyr Glu Val Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Gln Asn Leu Ile
            35                  40                  45

Glu Gln Ala Pro Leu Thr Val Ala Glu Lys Leu Gln Arg Glu Phe Leu
        50                  55                  60

Val Glu Trp Arg Arg Val Ser Lys Phe Leu Glu Ala Lys Phe Phe Val
65                  70                  75                  80

Gln Phe Glu Lys Gly Asp Ser Tyr Phe His Leu His Ile Leu Ile Glu
                85                  90                  95

Ile Thr Gly Val Lys Ser Met Val Val Gly Arg Tyr Val Ser Gln Ile
                100                 105                 110

Arg Asp Lys Leu Ile Gln Arg Ile Tyr Arg Gly Val Glu Pro Gln Leu
            115                 120                 125

Pro Asn Trp Phe Ala Val Thr Lys Thr Arg Asn Gly Ala Gly Gly Gly
        130                 135                 140
```

```
Asn Lys Val Val Asp Glu Cys Tyr Ile Pro Asn Tyr Leu Leu Pro Lys
145                 150                 155                 160

Val Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gly Asp Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Ile Gly Gln Gln
        275                 280                 285

Pro Val Gly Asp Ile Thr Thr Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ala Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Ala Asp His Val Thr Asp Val
465                 470                 475                 480

Ala His Glu Phe Tyr Val Thr Lys Gly Gly Ala Lys Lys Arg Pro Ala
                485                 490                 495

Pro Ser Asp Glu Asp Ile Ser Glu Pro Lys Arg Pro Arg Val Ser Phe
            500                 505                 510

Ala Gln Pro Glu Thr Ser Asp Ala Glu Ala Pro Gly Asp Phe Ala Asp
        515                 520                 525

Arg Tyr Gln Asn Lys Cys Ser Arg His Ala Gly Met Leu Gln Met Leu
    530                 535                 540

Phe Pro Cys Lys Thr Cys Glu Arg Met Asn Gln Asn Ser Asn Val Cys
545                 550                 555                 560

Phe Thr His Gly Gln Lys Asp Cys Gly Glu Cys Phe Pro Gly Ser Glu
```

```
                    565                 570                 575
Ser Gln Pro Val Ser Val Arg Lys Thr Tyr Gln Lys Leu Cys Ile
            580                 585                 590

Leu His Gln Leu Arg Gly Ala Pro Glu Ile Ala Cys Ser Ala Cys Asp
            595                 600                 605

Gln Leu Asn Pro Asp Leu Asp Cys Gln Phe Glu Gln
    610                 615                 620

<210> SEQ ID NO 36
<211> LENGTH: 736
<212> TYPE: PRT
<213> ORGANISM: Dependoparvovirus Adeno-associated virus - 1

<400> SEQUENCE: 36

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320
```

```
Val Lys Glu Val Thr Thr Asn Asp Gly Val Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 37
<211> LENGTH: 735
<212> TYPE: PRT
<213> ORGANISM: Dependoparvovirus Adeno-associated virus - 2

<400> SEQUENCE: 37

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

-continued

```
Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
        420                 425                 430

Leu Met Asn Pro Leu Ile Asp Gln Tyr Leu Tyr Tyr Leu Ser Arg Thr
    435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
        580                 585                 590

Ala Asp Val Asn Thr Gln Gly Val Leu Pro Gly Met Val Trp Gln Asp
    595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
        660                 665                 670

Tyr Ser Thr Gly Gln Val Ser Val Glu Ile Glu Trp Glu Leu Gln Lys
    675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 38
<211> LENGTH: 598
<212> TYPE: PRT
<213> ORGANISM: Dependoparvovirus Adeno-associated virus - 2

<400> SEQUENCE: 38

Met Ala Pro Gly Lys Lys Arg Pro Val Glu His Ser Pro Val Glu Pro
1               5                   10                  15

Asp Ser Ser Gly Thr Gly Lys Ala Gly Gln Gln Pro Ala Arg Lys
            20                  25                  30
```

```
Arg Leu Asn Phe Gly Gln Thr Gly Asp Ala Asp Ser Val Pro Asp Pro
         35                  40                  45

Gln Pro Leu Gly Gln Pro Pro Ala Ala Pro Ser Gly Leu Gly Thr Asn
 50                  55                  60

Thr Met Ala Thr Gly Ser Gly Ala Pro Met Ala Asp Asn Asn Glu Gly
 65                  70                  75                  80

Ala Asp Gly Val Gly Asn Ser Ser Gly Asn Trp His Cys Asp Ser Thr
                 85                  90                  95

Trp Met Gly Asp Arg Val Ile Thr Thr Ser Thr Arg Thr Trp Ala Leu
             100                 105                 110

Pro Thr Tyr Asn Asn His Leu Tyr Lys Gln Ile Ser Ser Gln Ser Gly
         115                 120                 125

Ala Ser Asn Asp Asn His Tyr Phe Gly Tyr Ser Thr Pro Trp Gly Tyr
         130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                 165                 170                 175

Lys Leu Phe Asn Ile Gln Val Lys Glu Val Thr Gln Asn Asp Gly Thr
             180                 185                 190

Thr Thr Ile Ala Asn Asn Leu Thr Ser Thr Val Gln Val Phe Thr Asp
         195                 200                 205

Ser Glu Tyr Gln Leu Pro Tyr Val Leu Gly Ser Ala His Gln Gly Cys
210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                 245                 250                 255

Cys Leu Glu Tyr Phe Pro Ser Gln Met Leu Arg Thr Gly Asn Asn Phe
             260                 265                 270

Thr Phe Ser Tyr Thr Phe Glu Asp Val Pro Phe His Ser Ser Tyr Ala
         275                 280                 285

His Ser Gln Ser Leu Asp Arg Leu Met Asn Pro Leu Ile Asp Gln Tyr
         290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                 325                 330                 335

Ser Arg Asn Trp Leu Pro Gly Pro Cys Tyr Arg Gln Gln Arg Val Ser
             340                 345                 350

Lys Thr Ser Ala Asp Asn Asn Ser Glu Tyr Ser Trp Thr Gly Ala
         355                 360                 365

Thr Lys Tyr His Leu Asn Gly Arg Asp Ser Leu Val Asn Pro Gly Pro
 370                 375                 380

Ala Met Ala Ser His Lys Asp Asp Glu Glu Lys Phe Phe Pro Gln Ser
385                 390                 395                 400

Gly Val Leu Ile Phe Gly Lys Gln Gly Ser Glu Lys Thr Asn Val Asp
                 405                 410                 415

Ile Glu Lys Val Met Ile Thr Asp Glu Glu Ile Arg Thr Thr Asn
             420                 425                 430

Pro Val Ala Thr Glu Gln Tyr Gly Ser Val Ser Thr Asn Leu Gln Arg
         435                 440                 445
```

Gly Asn Arg Gln Ala Ala Thr Ala Asp Val Asn Thr Gln Gly Val Leu
            450                 455                 460

Pro Gly Met Val Trp Gln Asp Arg Asp Val Tyr Leu Gln Gly Pro Ile
465                 470                 475                 480

Trp Ala Lys Ile Pro His Thr Asp Gly His Phe His Pro Ser Pro Leu
                485                 490                 495

Met Gly Gly Phe Gly Leu Lys His Pro Pro Gln Ile Leu Ile Lys
            500                 505                 510

Asn Thr Pro Val Pro Ala Asn Pro Ser Thr Thr Phe Ser Ala Ala Lys
            515                 520                 525

Phe Ala Ser Phe Ile Thr Gln Tyr Ser Thr Gly Gln Val Ser Val Glu
530                 535                 540

Ile Glu Trp Glu Leu Gln Lys Glu Asn Ser Lys Arg Trp Asn Pro Glu
545                 550                 555                 560

Ile Gln Tyr Thr Ser Asn Tyr Asn Lys Ser Val Asn Val Asp Phe Thr
                565                 570                 575

Val Asp Thr Asn Gly Val Tyr Ser Glu Pro Arg Pro Ile Gly Thr Arg
                580                 585                 590

Tyr Leu Thr Arg Asn Leu
            595

<210> SEQ ID NO 39
<211> LENGTH: 533
<212> TYPE: PRT
<213> ORGANISM: Dependoparvovirus Adeno-associated virus - 2

<400> SEQUENCE: 39

Met Ala Thr Gly Ser Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Gln Ser Gly Ala
    50                  55                  60

Ser Asn Asp Asn His Tyr Phe Gly Tyr Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn Asn Trp Gly Phe Arg Pro Lys Arg Leu Asn Phe Lys
            100                 105                 110

Leu Phe Asn Ile Gln Val Lys Glu Val Thr Gln Asn Asp Gly Thr Thr
        115                 120                 125

Thr Ile Ala Asn Asn Leu Thr Ser Thr Val Gln Val Phe Thr Asp Ser
    130                 135                 140

Glu Tyr Gln Leu Pro Tyr Val Leu Gly Ser Ala His Gln Gly Cys Leu
145                 150                 155                 160

Pro Pro Phe Pro Ala Asp Val Phe Met Val Pro Gln Tyr Gly Tyr Leu
                165                 170                 175

Thr Leu Asn Asn Gly Ser Gln Ala Val Gly Arg Ser Ser Phe Tyr Cys
            180                 185                 190

Leu Glu Tyr Phe Pro Ser Gln Met Leu Arg Thr Gly Asn Asn Phe Thr
        195                 200                 205

Phe Ser Tyr Thr Phe Glu Asp Val Pro Phe His Ser Ser Tyr Ala His
    210                 215                 220

Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Thr Gln Ser
                245                 250                 255

Arg Leu Gln Phe Ser Gln Ala Gly Ala Ser Asp Ile Arg Asp Gln Ser
            260                 265                 270

Arg Asn Trp Leu Pro Gly Pro Cys Tyr Arg Gln Gln Arg Val Ser Lys
            275                 280                 285

Thr Ser Ala Asp Asn Asn Asn Ser Glu Tyr Ser Trp Thr Gly Ala Thr
            290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
                325                 330                 335

Val Leu Ile Phe Gly Lys Gln Gly Ser Glu Lys Thr Asn Val Asp Ile
            340                 345                 350

Glu Lys Val Met Ile Thr Asp Glu Glu Ile Arg Thr Thr Asn Pro
            355                 360                 365

Val Ala Thr Glu Gln Tyr Gly Ser Val Ser Thr Asn Leu Gln Arg Gly
370                 375                 380

Asn Arg Gln Ala Ala Thr Ala Asp Val Asn Thr Gln Gly Val Leu Pro
385                 390                 395                 400

Gly Met Val Trp Gln Asp Arg Asp Val Tyr Leu Gln Gly Pro Ile Trp
                405                 410                 415

Ala Lys Ile Pro His Thr Asp Gly His Phe His Pro Ser Pro Leu Met
            420                 425                 430

Gly Gly Phe Gly Leu Lys His Pro Pro Gln Ile Leu Ile Lys Asn
            435                 440                 445

Thr Pro Val Pro Ala Asn Pro Ser Thr Thr Phe Ser Ala Ala Lys Phe
450                 455                 460

Ala Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Asn Lys Ser Val Asn Val Asp Phe Thr Val
            500                 505                 510

Asp Thr Asn Gly Val Tyr Ser Glu Pro Arg Pro Ile Gly Thr Arg Tyr
            515                 520                 525

Leu Thr Arg Asn Leu
            530

<210> SEQ ID NO 40
<211> LENGTH: 736
<212> TYPE: PRT
<213> ORGANISM: Dependoparvovirus Adeno-associated virus - 3

<400> SEQUENCE: 40

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
                20                  25                  30

Lys Ala Asn Gln Gln His Gln Asp Asn Arg Arg Gly Leu Val Leu Pro
            35                  40                  45

Gly Tyr Lys Tyr Leu Gly Pro Gly Asn Gly Leu Asp Lys Gly Glu Pro

```
                50                  55                  60
Val Asn Glu Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                     85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Ile Leu Glu Pro
                115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Thr Ser Leu Gly Ser Asn Thr Met Ala Ser Gly Gly Gly
                195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
                435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480
```

```
Gly Pro Cys Tyr Arg Gln Gln Arg Leu Ser Lys Thr Ala Asn Asp Asn
                485                 490                 495
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
            515                 520                 525
Asp Asp Glu Glu Lys Phe Phe Pro Met His Gly Asn Leu Ile Phe Gly
        530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
                565                 570                 575
Tyr Gly Thr Val Ala Asn Asn Leu Gln Ser Ser Asn Thr Ala Pro Thr
            580                 585                 590
Thr Arg Thr Val Asn Asp Gln Gly Ala Leu Pro Gly Met Val Trp Gln
        595                 600                 605
Asp Arg Asp Val Tyr Leu Gln Gly Pro Ile Trp Ala Lys Ile Pro His
        610                 615                 620
Thr Asp Gly His Phe His Pro Ser Pro Leu Met Gly Gly Phe Gly Leu
625                 630                 635                 640
Lys His Pro Pro Pro Gln Ile Met Ile Lys Asn Thr Pro Val Pro Ala
                645                 650                 655
Asn Pro Pro Thr Thr Phe Ser Pro Ala Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
690                 695                 700
Tyr Asn Lys Ser Val Asn Val Asp Phe Thr Val Asp Thr Asn Gly Val
705                 710                 715                 720
Tyr Ser Glu Pro Arg Pro Ile Gly Thr Arg Tyr Leu Thr Arg Asn Leu
                725                 730                 735
```

<210> SEQ ID NO 41
<211> LENGTH: 724
<212> TYPE: PRT
<213> ORGANISM: Dependoparvovirus Adeno-associated virus - 5

<400> SEQUENCE: 41

```
Met Ser Phe Val Asp His Pro Pro Asp Trp Leu Glu Glu Val Gly Glu
1               5                   10                  15
Gly Leu Arg Glu Phe Leu Gly Leu Glu Ala Gly Pro Pro Lys Pro Lys
                20                  25                  30
Pro Asn Gln Gln His Gln Asp Gln Ala Arg Gly Leu Val Leu Pro Gly
            35                  40                  45
Tyr Asn Tyr Leu Gly Pro Gly Asn Gly Leu Asp Arg Gly Glu Pro Val
        50                  55                  60
Asn Arg Ala Asp Glu Val Ala Arg Glu His Asp Ile Ser Tyr Asn Glu
65                  70                  75                  80
Gln Leu Glu Ala Gly Asp Asn Pro Tyr Leu Lys Tyr Asn His Ala Asp
                85                  90                  95
Ala Glu Phe Gln Glu Lys Leu Ala Asp Asp Thr Ser Phe Gly Gly Asn
            100                 105                 110
Leu Gly Lys Ala Val Phe Gln Ala Lys Lys Arg Val Leu Glu Pro Phe
```

```
            115                 120                 125
Gly Leu Val Glu Glu Gly Ala Lys Thr Ala Pro Thr Gly Lys Arg Ile
130                 135                 140

Asp Asp His Phe Pro Lys Arg Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
                180                 185                 190

Met Ser Ala Gly Gly Gly Pro Leu Gly Asp Asn Asn Gln Gly Ala
                195                 200                 205

Asp Gly Val Gly Asn Ala Ser Gly Asp Trp His Cys Asp Ser Thr Trp
210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
                260                 265                 270

Phe Asp Phe Asn Arg Phe His Ser His Trp Ser Pro Arg Asp Trp Gln
                275                 280                 285

Arg Leu Ile Asn Asn Tyr Trp Gly Phe Arg Pro Arg Ser Leu Arg Val
290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
                340                 345                 350

Leu Pro Ala Phe Pro Pro Gln Val Phe Thr Leu Pro Gln Tyr Gly Tyr
                355                 360                 365

Ala Thr Leu Asn Arg Asp Asn Thr Glu Asn Pro Thr Glu Arg Ser Ser
370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
                420                 425                 430

Gln Tyr Leu Tyr Arg Phe Val Ser Thr Asn Asn Thr Gly Gly Val Gln
                435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
                500                 505                 510

Asn Asn Leu Gln Gly Ser Asn Thr Tyr Ala Leu Glu Asn Thr Met Ile
                515                 520                 525

Phe Asn Ser Gln Pro Ala Asn Pro Gly Thr Thr Ala Thr Tyr Leu Glu
                530                 535                 540
```

-continued

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
            565                 570                 575

Thr Thr Ala Pro Ala Thr Gly Thr Tyr Asn Leu Gln Glu Ile Val Pro
                580                 585                 590

Gly Ser Val Trp Met Glu Arg Asp Val Tyr Leu Gln Gly Pro Ile Trp
            595                 600                 605

Ala Lys Ile Pro Glu Thr Gly Ala His Phe His Pro Ser Pro Ala Met
            610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 42
<211> LENGTH: 736
<212> TYPE: PRT
<213> ORGANISM: Dependoparvovirus Adeno-associated virus - 6

<400> SEQUENCE: 42

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

```
Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
        210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
        450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605
```

```
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys His Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Val Gln Tyr Thr Ser Asn
690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735
```

<210> SEQ ID NO 43
<211> LENGTH: 737
<212> TYPE: PRT
<213> ORGANISM: Dependoparvovirus Adeno-associated virus - 7

<400> SEQUENCE: 43

```
Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asn Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Ala Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Ser Val Gly Ser Gly Thr Val Ala Ala Gly Gly
        195                 200                 205
Gly Ala Pro Met Ala Asp Asn Asn Glu Gly Ala Asp Gly Val Gly Asn
    210                 215                 220
Ala Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
```

```
Leu Tyr Lys Gln Ile Ser Ser Glu Thr Ala Gly Ser Thr Asn Asp Asn
                260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
        370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
            450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670
```

```
Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 44
<211> LENGTH: 737
<212> TYPE: PRT
<213> ORGANISM: Dependoparvovirus Adeno-associated virus - 8

<400> SEQUENCE: 44

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300
```

```
Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
```

725                 730                 735
Asn

<210> SEQ ID NO 45
<211> LENGTH: 736
<212> TYPE: PRT
<213> ORGANISM: Dependoparvovirus Adeno-associated virus - 9

<400> SEQUENCE: 45

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro

```
                355                 360                 365
Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
                450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
                690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 46
<211> LENGTH: 738
<212> TYPE: PRT
<213> ORGANISM: Dependoparvovirus Adeno-associated virus - 10

<400> SEQUENCE: 46
```

-continued

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Glu Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
```

-continued

```
                420                 425                 430
Leu Asp Arg Leu Met Asn Pro Leu Ile Asp Gln Tyr Leu Tyr Tyr Leu
            435                 440                 445

Ser Arg Thr Gln Ser Thr Gly Gly Thr Gln Gly Thr Gln Gln Leu Leu
450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
            485                 490                 495

Gln Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
530                 535                 540

Phe Gly Lys Gln Gly Ala Gly Arg Asp Asn Val Asp Tyr Ser Ser Val
545                 550                 555                 560

Met Leu Thr Ser Glu Glu Ile Lys Thr Thr Asn Pro Val Ala Thr
            565                 570                 575

Glu Gln Tyr Gly Val Val Ala Asp Asn Leu Gln Gln Ala Asn Thr Gly
            580                 585                 590

Pro Ile Val Gly Asn Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
            725                 730                 735

Asn Leu
```

<210> SEQ ID NO 47
<211> LENGTH: 733
<212> TYPE: PRT
<213> ORGANISM: Dependoparvovirus Adeno-associated virus - 11

<400> SEQUENCE: 47

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
```

```
            50                  55                  60
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
130                 135                 140

Pro Leu Glu Ser Pro Gln Glu Pro Asp Ser Ser Gly Ile Gly Lys
145                 150                 155                 160

Lys Gly Lys Gln Pro Ala Arg Lys Arg Leu Asn Phe Glu Glu Asp Thr
                165                 170                 175

Gly Ala Gly Asp Gly Pro Pro Glu Gly Ser Asp Thr Ser Ala Met Ser
                180                 185                 190

Ser Asp Ile Glu Met Arg Ala Ala Pro Gly Gly Asn Ala Val Asp Ala
                195                 200                 205

Gly Gln Gly Ser Asp Gly Val Gly Asn Ala Ser Gly Asp Trp His Cys
                210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Ser Ser Asn Thr Tyr Asn Gly Phe Ser Thr Pro Trp Gly Tyr
                260                 265                 270

Phe Asp Phe Asn Arg Phe His Cys His Phe Ser Pro Arg Asp Trp Gln
                275                 280                 285

Arg Leu Ile Asn Asn Asn Trp Gly Leu Arg Pro Lys Ala Met Arg Val
                290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
                340                 345                 350

Leu Pro Pro Phe Pro Asn Asp Val Phe Met Val Pro Gln Tyr Gly Tyr
                355                 360                 365

Cys Gly Ile Val Thr Gly Glu Asn Gln Asn Gln Thr Asp Arg Asn Ala
                370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
                420                 425                 430

Gln Tyr Leu Trp His Leu Gln Ser Thr Thr Ser Gly Glu Thr Leu Asn
                435                 440                 445

Gln Gly Asn Ala Ala Thr Thr Phe Gly Lys Ile Arg Ser Gly Asp Phe
                450                 455                 460

Ala Phe Tyr Arg Lys Asn Trp Leu Pro Gly Pro Cys Val Lys Gln Gln
465                 470                 475                 480
```

-continued

```
Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Met Ala Thr Ala Gly Pro Ser
            515                 520                 525

Asp Gly Asp Phe Ser Asn Ala Gln Leu Ile Phe Pro Gly Pro Ser Val
            530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
            595                 600                 605

Ile Tyr Tyr Gln Gly Pro Ile Trp Ala Lys Ile Pro His Ala Asp Gly
            610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
            675                 680                 685

Ser Lys Arg Trp Asn Pro Glu Val Gln Phe Thr Ser Asn Tyr Gly Asn
            690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730
```

```
<210> SEQ ID NO 48
<211> LENGTH: 742
<212> TYPE: PRT
<213> ORGANISM: Dependoparvovirus Adeno-associated virus - 12

<400> SEQUENCE: 48

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
                100                 105                 110

Asn Leu Gly Arg Ala Val Phe Gln Ala Lys Lys Arg Ile Leu Glu Pro
```

```
                115                 120                 125
Leu Gly Leu Val Glu Glu Gly Val Lys Thr Ala Pro Gly Lys Lys Arg
            130                 135                 140
Pro Leu Glu Lys Thr Pro Asn Arg Pro Thr Asn Pro Asp Ser Gly Lys
145                 150                 155                 160
Ala Pro Ala Lys Lys Gln Lys Asp Gly Glu Pro Ala Asp Ser Ala
                165                 170                 175
Arg Arg Thr Leu Asp Phe Glu Asp Ser Gly Ala Gly Asp Gly Pro Pro
            180                 185                 190
Glu Gly Ser Ser Ser Gly Glu Met Ser His Asp Ala Glu Met Arg Ala
            195                 200                 205
Ala Pro Gly Gly Asn Ala Val Glu Ala Gly Gln Gly Ala Asp Gly Val
            210                 215                 220
Gly Asn Ala Ser Gly Asp Trp His Cys Asp Ser Thr Trp Ser Glu Gly
225                 230                 235                 240
Arg Val Thr Thr Thr Ser Thr Arg Thr Trp Val Leu Pro Thr Tyr Asn
                245                 250                 255
Asn His Leu Tyr Leu Arg Ile Gly Thr Thr Ala Asn Ser Asn Thr Tyr
            260                 265                 270
Asn Gly Phe Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
            290                 295                 300
Gly Leu Arg Pro Lys Ser Met Arg Val Lys Ile Phe Asn Ile Gln Val
305                 310                 315                 320
Lys Glu Val Thr Thr Ser Asn Gly Glu Thr Thr Val Ala Asn Asn Leu
                325                 330                 335
Thr Ser Thr Val Gln Ile Phe Ala Asp Ser Thr Tyr Glu Leu Pro Tyr
            340                 345                 350
Val Met Asp Ala Gly Gln Glu Gly Ser Phe Pro Pro Phe Pro Asn Asp
            355                 360                 365
Val Phe Met Val Pro Gln Tyr Gly Tyr Cys Gly Val Val Thr Gly Lys
            370                 375                 380
Asn Gln Asn Gln Thr Asp Arg Asn Ala Phe Tyr Cys Leu Glu Tyr Phe
385                 390                 395                 400
Pro Ser Gln Met Leu Arg Thr Gly Asn Asn Phe Glu Val Ser Tyr Gln
                405                 410                 415
Phe Glu Lys Val Pro Phe His Ser Met Tyr Ala His Ser Gln Ser Leu
                420                 425                 430
Asp Arg Met Met Asn Pro Leu Leu Asp Gln Tyr Leu Trp His Leu Gln
            435                 440                 445
Ser Thr Thr Thr Gly Asn Ser Leu Asn Gln Gly Thr Ala Thr Thr Thr
            450                 455                 460
Tyr Gly Lys Ile Thr Thr Gly Asp Phe Ala Tyr Tyr Arg Lys Asn Trp
465                 470                 475                 480
Leu Pro Gly Ala Cys Ile Lys Gln Gln Lys Phe Ser Lys Asn Ala Asn
                485                 490                 495
Gln Asn Tyr Lys Ile Pro Ala Ser Gly Gly Asp Ala Leu Leu Lys Tyr
            500                 505                 510
Asp Thr His Thr Thr Leu Asn Gly Arg Trp Ser Asn Met Ala Pro Gly
            515                 520                 525
Pro Pro Met Ala Thr Ala Gly Ala Gly Asp Ser Asp Phe Ser Asn Ser
            530                 535                 540
```

```
Gln Leu Ile Phe Ala Gly Pro Asn Pro Ser Gly Asn Thr Thr Thr Ser
545                 550                 555                 560

Ser Asn Asn Leu Leu Phe Thr Ser Glu Glu Glu Ile Ala Thr Thr Asn
                565                 570                 575

Pro Arg Asp Thr Asp Met Phe Gly Gln Ile Ala Asp Asn Asn Gln Asn
            580                 585                 590

Ala Thr Thr Ala Pro His Ile Ala Asn Leu Asp Ala Met Gly Ile Val
            595                 600                 605

Pro Gly Met Val Trp Gln Asn Arg Asp Ile Tyr Tyr Gln Gly Pro Ile
        610                 615                 620

Trp Ala Lys Val Pro His Thr Asp Gly His Phe His Pro Ser Pro Leu
625                 630                 635                 640

Met Gly Gly Phe Gly Leu Lys His Pro Pro Gln Ile Phe Ile Lys
                645                 650                 655

Asn Thr Pro Val Pro Ala Asn Pro Asn Thr Thr Phe Ser Ala Ala Arg
            660                 665                 670

Ile Asn Ser Phe Leu Thr Gln Tyr Ser Thr Gly Gln Val Ala Val Gln
        675                 680                 685

Ile Asp Trp Glu Ile Gln Lys Glu His Ser Lys Arg Trp Asn Pro Glu
690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Leu Arg Ala Ile Gly Ser Arg
                725                 730                 735

Phe Leu Thr His His Leu
            740

<210> SEQ ID NO 49
<211> LENGTH: 1625
<212> TYPE: DNA
<213> ORGANISM: Artificial Sequence
<220> FEATURE:
<223> OTHER INFORMATION: WT parkin construct

<400> SEQUENCE: 49
cctgggcaac gtgctggtta ttgtgctgtc tcatcatttt ggcaaagaat tcctcgaaga      60
tccgaagggg ttcaagctta tcatcatgat agtgtttgtc aggttcaact ccagccatgg     120
tttcccagtg gaggtcgatt ctgacaccag catcttccag ctcaaggagg tggttgctaa     180
gcgacagggg gttccggctg accagttgcg tgtgattttc gcaggaaagg agctgaggaa     240
tgactggact gtgcagaatt gtgacctgga tcagcagagc attgttcaca ttgtgcagag     300
accgtggaga aaaggtcaag aaatgaatgc aactggaggc gacgacccca gaaacgcggc     360
gggaggctgt gagcgggagc cccagagctt gactcgggtg gaccctcagc agtcagtcct     420
cccaggagac tctgtggggc tggctgtcat tctgcacact gacagcagga aggactcacc     480
accagctgga agtccagcag gtagatcaat ctacaacagc ttttatgtgt attgcaaagg     540
cccctgtcaa agagtgcagc cgggaaaact cagggtacag tgcagcacct gcaggcaggc     600
aacgctcacc ttgacccagg gtccatcttg ctgggatgat gttttaattc aaaccggat     660 gagtggtgaa tgccaatccc cacactgccc tgggactagt gcagaatttt tctttaaatg     720
tggagcacac cccacctctg acaaggaaac atcagtagct ttgcacctga tcgcaacaaa     780
tagtcggaac atcacttgca ttacgtgcac agacgtcagg agccccgtcc tggttttcca     840
gtgcaactcc cgccacgtga tttgcttaga ctgtttccac ttatactgtg tgacaagact     900
```

```
caatgatcgg cagtttgttc acgaccctca acttggctac tccctgcctt gtgtggctgg      960
ctgtcccaac tccttgatta agagctcca tcacttcagg attctgggag aagagcagta     1020
caaccggtac cagcagtatg gtgcagagga gtgtgtcctg cagatggggg gcgtgttatg     1080
cccccgccct ggctgtggag cggggctgct gccggagcct gaccagagga aagtcacctg     1140 cgaaggggc aatggcctgg gctgtgggtt tgccttctgc cgggaatgta aagaagcgta      1200
ccatgaaggg gagtgcagtg ccgtatttga agcctcagga acaactactc aggcctacag     1260
agtcgatgaa agagccgccg agcaggctcg ttgggaagca gcctccaaag aaaccatcaa     1320
gaaaaccacc aagccctgtc cccgctgcca tgtaccagtg gaaaaaaatg gaggctgcat     1380
gcacatgaag tgtccgcagc cccagtgcag gctcgagtgg tgctggaact gtggctgcga     1440
gtggaaccgc gtctgcatgg gggaccactg gttcgacgtg taaagtcgac aacttgttta     1500
ttgcagctta taatggttac aaataaagca atagcatcac aaatttcaca aataaagcat     1560 tttttttcact gcattctagt tgtggtttgt ccaaactcat caatgtatct tatcatgtct     1620
ggatc                                                                1625

<210> SEQ ID NO 50
<211> LENGTH: 1625
<212> TYPE: DNA
<213> ORGANISM: Artificial Sequence
<220> FEATURE:
<223> OTHER INFORMATION: 183Y construct

<400> SEQUENCE: 50
cctgggcaac gtgctggtta ttgtgctgtc tcatcatttt ggcaaagaat tcctcgaaga       60
tccgaagggg ttcaagctta tcatcatgat agtgtttgtc aggttcaact ccagccatgg      120
tttcccagtg gaggtcgatt ctgacaccag catcttccag ctcaaggagg tggttgctaa      180
gcgacagggg gttccggctg accagttgcg tgtgattttc gcaggaaagg agctgaggaa      240
tgactggact gtgcagaatt gtgacctgga tcagcagagc attgttcaca ttgtgcagag      300
accgtggaga aaaggtcaag aaatgaatgc aactggaggc gacgacccca gaaacgcggc      360
gggaggctgt gagcgggagc cccagagctt gactcgggtg gacctcagca gctcagtcct      420
cccaggagac tctgtggggc tggctgtcat tctgcacact gacagcagga aggactcacc      480
accagctgga agtccagcag gtagatcaat ctacaacagc ttttatgtgt attgcaaagg      540
cccctgtcaa agagtgcagc cgggaaaact cagggtacag tgcagcacct gcaggcaggc      600
aacgctcacc ttgacccagg gtccatcttg ctacgatgat gttttaattc caaaccggat      660
gagtggtgaa tgccaatccc cacactgccc tgggactagt gcagaatttt tctttaaatg      720
tggagcacac cccacctctg acaaggaaac atcagtagct ttgcacctga tcgcaacaaa      780
tagtcggaac atcacttgca ttacgtgcac agacgtcagg agcccgtcc tggttttcca       840 gtgcaactcc cgccacgtga tttgcttaga ctgtttccac ttatactgtg tgacaagact      900
caatgatcgg cagtttgttc acgaccctca acttggctac tccctgcctt gtgtggctgg      960
ctgtcccaac tccttgatta agagctcca tcacttcagg attctgggag aagagcagta     1020
caaccggtac cagcagtatg gtgcagagga gtgtgtcctg cagatggggg gcgtgttatg     1080
cccccgccct ggctgtggag cggggctgct gccggagcct gaccagagga aagtcacctg     1140 cgaaggggc aatggcctgg gctgtgggtt tgccttctgc cgggaatgta aagaagcgta      1200
ccatgaaggg gagtgcagtg ccgtatttga agcctcagga acaactactc aggcctacag     1260
```

| | |
|---|---|
| agtcgatgaa agagccgccg agcaggctcg ttgggaagca gcctccaaag aaaccatcaa | 1320 |
| gaaaaccacc aagccctgtc cccgctgcca tgtaccagtg gaaaaaaatg gaggctgcat | 1380 |
| gcacatgaag tgtccgcagc cccagtgcag gctcgagtgg tgctggaact gtggctgcga | 1440 |
| gtggaaccgc gtctgcatgg gggaccactg gttcgacgtg taaagtcgac aacttgttta | 1500 |
| ttgcagctta taatggttac aaataaagca atagcatcac aaatttcaca aataaagcat | 1560 |
| tttttttcact gcattctagt tgtggttttgt ccaaactcat caatgtatct tatcatgtct | 1620 |
| ggatc | 1625 |

<210> SEQ ID NO 51
<211> LENGTH: 1625
<212> TYPE: DNA
<213> ORGANISM: Artificial Sequence
<220> FEATURE:
<223> OTHER INFORMATION: 208Y construct

<400> SEQUENCE: 51

| | |
|---|---|
| cctgggcaac gtgctggtta ttgtgctgtc tcatcatttt ggcaaagaat tcctcgaaga | 60 |
| tccgaagggg ttcaagctta tcatcatgat agtgtttgtc aggttcaact ccagccatgg | 120 |
| tttcccagtg gaggtcgatt ctgacaccag catcttccag ctcaaggagg tggttgctaa | 180 |
| gcgacagggg gttccggctg accagttgcg tgtgattttc gcaggaagg agctgaggaa | 240 |
| tgactggact gtgcagaatt gtgacctgga tcagcagagc attgttcaca ttgtgcagag | 300 |
| accgtggaga aaaggtcaag aaatgaatgc aactggaggc gacgaccca gaaacgcggc | 360 |
| gggaggctgt gagcgggagc cccagagctt gactcgggtg gacctcagca gctcagtcct | 420 |
| cccaggagac tctgtggggc tggctgtcat tctgcacact gacagcagga aggactcacc | 480 |
| accagctgga agtccagcag gtagatcaat ctacaacagc ttttatgtgt attgcaaagg | 540 |
| ccctgtcaa agagtgcagc cgggaaaact cagggtacag tgcagcacct gcaggcaggc | 600 |
| aacgctcacc ttgacccagg gtccatcttg ctgggatgat gttttaattc caaaccggat | 660 |
| gagtggtgaa tgccaatccc cacactgccc tgggactagt gcagaatact tctttaaatg | 720 |
| tggagcacac cccaccctctg acaaggaaac atcagtagct ttgcacctga tcgcaacaaa | 780 |
| tagtcggaac atcacttgca ttacgtgcac agacgtcagg agcccccgtcc tggttttcca | 840 |
| gtgcaactcc cgccacgtga tttgcttaga ctgtttccac ttatactgtg tgacaagact | 900 |
| caatgatcgg cagtttgttc acgaccctca acttggctac tccctgcctt gtgtggctgg | 960 |
| ctgtcccaac tccttgatta aagagctcca tcacttcagg attctgggag aagagcagta | 1020 |
| caaccggtac cagcagtatg gtgcagagga gtgtgtcctg cagatggggg gcgtgttatg | 1080 |
| cccccgccct ggctgtggag cggggctgct gccggagcct gaccagagga aagtcacctg | 1140 |
| cgaagggggc aatggcctgg gctgtgggtt tgccttctgc cgggaatgta agaagcgta | 1200 |
| ccatgaaggg gagtgcagtg ccgtatttga agcctcagga caactactc aggcctacag | 1260 |
| agtcgatgaa agagccgccg agcaggctcg ttgggaagca gcctccaaag aaaccatcaa | 1320 |
| gaaaaccacc aagccctgtc cccgctgcca tgtaccagtg gaaaaaaatg gaggctgcat | 1380 |
| gcacatgaag tgtccgcagc cccagtgcag gctcgagtgg tgctggaact gtggctgcga | 1440 |
| gtggaaccgc gtctgcatgg gggaccactg gttcgacgtg taaagtcgac aacttgttta | 1500 |
| ttgcagctta taatggttac aaataaagca atagcatcac aaatttcaca aataaagcat | 1560 |
| tttttttcact gcattctagt tgtggttttgt ccaaactcat caatgtatct tatcatgtct | 1620 |
| ggatc | 1625 |

<210> SEQ ID NO 52
<211> LENGTH: 1624
<212> TYPE: DNA
<213> ORGANISM: Artificial Sequence
<220> FEATURE:
<223> OTHER INFORMATION: 463Y construct

<400> SEQUENCE: 52

```
cctgggcaac gtgctggtta ttgtgctgtc tcatcatttt ggcaaagaat tcctcgaaga      60
tccgaagggg ttcaagctta tcatcatgat agtgtttgtc aggttcaact ccagccatgg     120
tttcccagtg gaggtcgatt ctgacaccag catcttccag ctcaaggagg tggttgctaa     180
gcgacagggg gttccggctg accagttgcg tgtgattttc gcagggaagg agctgaggaa     240
tgactggact gtgcagaatt gtgacctgga tcagcagagc attgttcaca ttgtgcagag     300
accgtggaga aaaggtcaag aaatgaatgc aactggaggc gacgacccca gaaacgcggc     360
gggaggctgt gagcgggagc cccagagctt gactcgggtg gacctcagca gctcagtcct     420
cccaggagac tctgtggggc tggctgtcat tctgcacact gacagcagga aggactcacc     480
accagctgga agtccagcag gtagatcaat ctacaacagc ttttatgtgt attgcaaagg     540
cccctgtcaa agagtgcagc cgggaaaact cagggtacag tgcagcacct gcaggcaggc     600
aacgctcacc ttgacccagg gtccatcttg ctgggatgat gttttaattc caaaccggat     660
gagtggtgaa tgccaatccc cacactgccc tgggactagt gcagaatttt tctttaaatg     720
tggagcacac cccacctctg acaaggaaac atcagtagct ttgcacctga tcgcaacaaa     780
tagtcggaac atcacttgca ttacgtgcac agacgtcagg agcccgtcc tggtttttcca     840
gtgcaactcc cgccacgtga tttgcttaga ctgtttccac ttatactgtg tgacaagacc     900
aatgatcggc agtttgttca cgaccctcaa cttggctact ccctgccttg tgtggctggc     960
tgtcccaact ccttgattaa agagctccat cacttcagga ttctgggaga agagcagtac    1020
aaccggtacc agcagtatgg tgcagaggag tgtgtcctgc agatgggggg cgtgttatgc    1080
ccccgccctg gctgtggagc ggggctgctg ccggagcctg accagaggaa agtcacctgc    1140
gaaggggca atggcctggg ctgtgggttt gccttctgcc gggaatgtaa agaagcgtac    1200
catgaagggg agtgcagtgc cgtatttgaa gcctcaggaa caactactca ggcctacaga    1260
gtcgatgaaa gagccgccga gcaggctcgt tgggaagcag cctccaaaga aaccatcaag    1320
aaaaccacca gccctgtcc ccgctgccat gtaccagtgg aaaaaaatgg aggctgcatg    1380
cacatgaagt gtccgcagcc ccagtgcagg ctcgagtggt gctggaactg tggctgcgag    1440
tggaaccgcg tctgcatggg ggaccactgg tacgacgtgt aaagtcgaca acttgtttat    1500
tgcagcttat aatggttaca aataaagcaa tagcatcaca aatttcacaa ataaagcatt    1560
tttttcactg cattctagtt gtggtttgtc caaactcatc aatgtatctt atcatgtctg    1620
gatc                                                                1624
```

GENE THERAPY DELIVERY OF PARKIN MUTANTS HAVING INCREASED ACTIVITY TO TREAT PARKINSON'S DISEASE

CROSS-REFERENCE TO RELATED APPLICATIONS

This application claims priority to U.S. Provisional Application No. 63/028,335 filed May 21, 2020, the contents of each of which are herein incorporated by reference in its entirety.

DESCRIPTION OF THE TEXT FILE SUBMITTED ELECTRONICALLY

The contents of the text file submitted electronically herewith are incorporated herein by reference in their entirety: a computer readable format copy of the sequence listing (filename: NYSN-012/01US_SeqList_ST25.txt, date recorded May 21, 2021, file size 254 kilobytes)

FIELD OF THE DISCLOSURE

The present disclosure relates generally to gene therapy for treatment of Parkinson's Disease. In particular, the disclosure provides compositions and methods for gene therapy in neurons.

BACKGROUND OF THE INVENTION

The Ubiquitin-Proteasome Pathway System (UPS) is a critical pathway that regulates key regulator proteins and degrades misfolded or abnormal proteins. UPS is central to multiple cellular processes, and if defective or imbalanced, it leads to pathogenesis of a variety of diseases. Posttranslational modification of proteins by ubiquitin is a fundamental cellular mechanism that regulates protein stability and activity and underlies a multitude of functions, from almost every aspect of biology. The covalent attachment of ubiquitin to specific protein substrates is achieved through the action of E3 ubiquitin ligases. These ligases comprise over 500 different proteins and are categorized into multiple classes defined by the structural element of their E3 functional activity.

Parkin, which has been implicated in disorders of the central nervous system such as Parkinson's Disease (PD), is a RING-between-RING E3 ligase that functions in the covalent attachment of ubiquitin to specific substrates, and mutations in Parkin are linked to Parkinson's disease, cancer and mycobacterial infection. The individual RING domains for Parkin have been the subject of much debate, in regards to the specific residues that coordinate Zn ions, as well as their relationship to canonical RING crossbrace structures defining classical E2-binding domains. R0 is a novel domain structure, but is more similar to Zn-finger domains than to E3 RING domains (Riley et al. 2013. *Nat Commun.* 4:1982)

There have been few reports of successful gene therapy for Parkinson's Disease, and thus there is a need in the art for new gene therapy compositions and methods of treating and preventing Parkinson's Disease.

SUMMARY OF THE INVENTION

The present disclosure is directed towards a novel approach of gene therapy to replace or repair a defective parkin gene (PARK2) in a patient with Parkinson's Disease to provide a therapeutic benefit.

In some aspects, the present disclosure provides methods of treating, preventing, or ameliorating a central nervous system disorder or a symptom thereof in a patient in need thereof, comprising administering a pharmaceutical composition comprising an AAV5 vector comprising a gene therapy construct comprising a parkin (PARK2) gene, wherein the method comprises administering the pharmaceutical composition to the brain of the patient. In some embodiments, the PARK2 gene is a variant PARK2 gene having at least 95% identity to the polynucleotide of SEQ ID NO: 1. In some embodiments, the variant PARK2 gene encodes for a variant parkin polypeptide having greater biological activity than a wild type parkin polypeptide. In some embodiments, the expressed variant parkin polypeptide demonstrates increased auto-ubiquitination compared to the wild-type parkin polypeptide of SEQ ID NO: 2. In some embodiments, the variant PARK2 gene encodes a polypeptide with a mutation at the amino acid position of 146, 183 and/or 463 of SEQ ID NO: 2. In some embodiments, the variant PARK2 gene encodes a polypeptide with a mutation at the amino acid position of 146 and/or 183 of SEQ ID NO: 2. In some embodiments, the mutation comprises substitution of the amino acid residue to a tyrosine residue. In some embodiments, the polypeptide comprises SEQ ID NO: 4, 6, or 8. In some embodiments, the variant PARK2 gene comprises the nucleic acid sequence of any one of SEQ ID NOs: 3, 5, and 7.

In some embodiments, expression of the PARK2 gene is under control of a tissue specific promoter. In some embodiments, expression of the PARK2 gene is under control of a neuron-specific promoter. In some embodiments, expression of the PARK2 gene is under control of a ubiquitous promoter. In some embodiments, the PARK2 gene is under control of a promoter selected from the list: chicken-beta-actin (CBA), human beta actin (HuBa), cytomegalovirus (cMV), CAG, PGL, EF1-alpha, GAPDFI, SV40, FIBV, human synapsin (hSYN1), alpha-internexin (INA), nestin (NES), tyrosine hydroxylase (TH), forkhead box A2 (FOXA2), calmodulin-dependent protein kinase II (CAM-KII), and neuron-specific enolase (NSE).

In some embodiments, the pharmaceutical composition is administered by intrathecal administration. In some embodiments, the pharmaceutical composition is administered to the substantia nigra of the subject's brain.

In some embodiments, administration of the pharmaceutical composition results in expression of the parkin gene in neurons and glial cells. In some embodiments, the neurons are dopaminergic neurons or oligodendrocytes. In some embodiments, the glial cells are astrocytes. In some embodiments, administration of the pharmaceutical composition increases the number of dopaminergic neurons in the patient.

In some embodiments, the central nervous system disorder is Parkinson's Disease. In some embodiments, the patient displays one or more symptoms of Parkinson's Disease. In some embodiments, the patient is at risk of developing one or more symptoms of Parkinson's Disease. In some embodiments, the one or more symptoms of Parkinson's Disease is selected from the group consisting of: motor deficits, tremors, bradykinesia (slowed movement), rigid muscles, impaired posture and balance, loss of automatic movements, speech changes, writing changes, depression, swallowing problems, decreased cardiac function, sleep disorders, dementia, cognitive problems, emotional changes (e.g. fear, anxiety, or loss of motivation), blood pressure changes, fatigue, pain, involuntary movements, shuffling gait, dizziness, amnesia, confusion, voice box spasms, distorted sense of smell, jaw stiffness or reduced facial expression, and weight loss.

In some aspects, the present disclosure provides a recombinant gene therapy vector comprising a variant parkin (PARK2) gene packaged into an AAV5 capsid for administration to a patient in need thereof.

In some aspects, the present disclosure provides a recombinant nucleic acid molecule comprising a WT or mutant parkin (PARK2) sequence, and a sequence encoding an AAV capsid protein or portion thereof. In some embodiments, the sequence encodes an AAV capsid protein selected from AAV1, AAV2, AAV3, AAV4, AAV5, AAV6, AAV7, AAV8, AAV9, AAV10, AAV11, AAV12, or AAV13 capsid protein, or a mutant AAV capsid protein at least 95% identical to an AAV capsid protein selected from AAV1, AAV2, AAV3, AAV4, AAV5, AAV6, AAV7, AAV8, AAV9, AAV10, AAV11, AAV12, or AAV13 capsid protein. In some embodiments, the sequence encoding an AAV capsid protein is selected from any one of SEQ ID NOs: 9-20. In some embodiments, the sequence encoding an AAV capsid protein or portion thereof encodes a vp1-3 capsid protein or fragment thereof. In some embodiments, the sequence encoding a vp1-3 capsid protein is selected from any one of SEQ ID NOs: 36-48. In some embodiments, the sequence encodes an AAV capsid protein at least 95% identical to an AAV5 capsid protein. In some embodiments, the sequence encodes SEQ ID NO: 13

In some embodiments, the recombinant nucleic acid molecule comprises a functional rep gene. In some embodiments, the rep gene is AAV2 rep gene.

In some embodiments, he WT or variant parkin (PARK2) sequence encodes for SEQ ID NO: 2 or a polypeptide with at least 95% sequence identity to SEQ ID NO: 2. In some embodiments, the PARK2 sequence encodes a polypeptide with a mutation at the amino acid position of 146, 183 and/or 463 of SEQ ID NO: 2. In some embodiments, the PARK2 sequence encodes a polypeptide with a mutation at the amino acid position of 146 or 183 of SEQ ID NO: 2. In some embodiments, the PARK2 sequence encodes for SEQ ID NO: 2.

In some aspects the present disclosure provides a cultured host cell comprising the recombinant nucleic acid molecule or gene therapy vector of the disclosure. In some embodiments, the recombinant nucleic acid molecule is a plasmid.

DETAILED DESCRIPTION

Definitions

Figure 1:
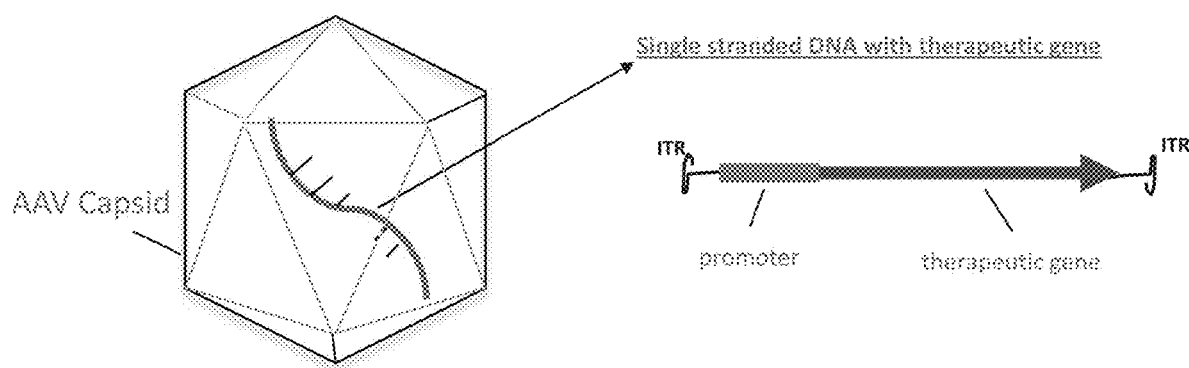
FIG. 1 shows an exemplary schematic of the gene therapy constructs disclosed herein.

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a kinase inhibitor" refers to one or more kinase inhibitors or at least one kinase inhibitor. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or pharmaceutical formulation that is sufficient to result in a desired clinical benefit after administration to a patient in need thereof.

All weight percentages (i.e., "% by weight" and "wt. %" and w/w) referenced herein, unless otherwise indicated, are measured relative to the total weight of the pharmaceutical composition.

"Ubiquitin Proteasome Pathway System (UPS)" as used herein relates to the ubiquitin proteasome pathway, conserved from yeast to mammals, and is required for the targeted degradation of most short-lived proteins in the eukaryotic cell. Targets include cell cycle regulatory proteins, whose timely destruction is vital for controlled cell division, as well as proteins unable to fold properly within the endoplasmic reticulum. Ubiquitin modification is an ATP-dependent process carried out by three classes of enzymes. An "ubiquitin activating enzyme" (E1) forms a thio-ester bond with ubiquitin, a highly conserved 76-amino acid protein. This reaction allows subsequent binding of ubiquitin to a "ubiquitin conjugating enzyme" (E2), followed by the formation of an isopeptide bond between the carboxy-terminus of ubiquitin and a lysine residue on the substrate protein. The latter reaction requires a "ubiquitin ligase" (E3). E3 ligases can be single- or multi-subunit enzymes. In some cases, the ubiquitin-binding and substrate binding domains reside on separate polypeptides brought together by adaptor proteins or culling. Numerous E3 ligases provide specificity in that each can modify only a subset of substrate proteins. Further specificity is achieved by post-translational modification of substrate proteins, including, but not limited to, phosphorylation. Effects of mono-ubiquitination include changes in subcellular localization. However, multiple ubiquitination cycles resulting in a poly-ubiquitin chain are required for targeting a protein to the proteasome for degradation. The multisubunit 26S proteasome recognizes, unfolds, and degrades poly-ubiquitinated substrates into small peptides. The reaction occurs within the cylindrical core of the proteasome complex, and peptide bond hydrolysis employs a core threonine residue as the catalytic nucleophile. It has been shown that an additional layer of complexity, in the form of multi-ubiquitin chain receptors, may lie between the poly-ubiquitination and degradation steps. These receptors react with a subset of poly-ubiquitinated substrates, aiding in their recognition by the 26S proteasome, and thereby promoting their degradation. This pathway is not only important in cellular homeostasis, but also in human disease. Because ubiquitin/proteasome-dependent degradation is often employed in control of the cell division cycle and cell growth, researchers have found that proteasome inhibitors hold some promise of being developed into potential cancer therapeutic agents.

Protein degradation through the ubiquitin-proteasome system is the major pathway of non-lysosomal proteolysis of intracellular proteins. It plays important roles in a variety of fundamental cellular processes such as regulation of cell cycle progression, division, development and differentiation, apoptosis, cell trafficking, and modulation of the immune and inflammatory responses. The central element of this system is the covalent linkage of ubiquitin to targeted proteins, which are then recognized by the 26S proteasome, an adenosine triphosphate-dependent, multi-catalytic protease. Damaged, oxidized, or misfolded proteins as well as regulatory proteins that control many critical cellular functions are among the targets of this degradation process. Aberration of this system leads to the dysregulation of cellular homeostasis and the development of multiple diseases (Wang et al. *Cell Mol Immunol.* 2006 August; 3(4): 255-61).

"Parkin ligase" or "Parkin" as used herein relates to a protein which in humans is encoded by the PARK2 gene. (Kitada T, Asakawa S, Hattori N, Matsumine H, Yamamura Y, Minoshima S, Yokochi M, Mizuno Y, Shimizu N (April 1998). "Mutations in the parkin gene cause autosomal recessive juvenile parkinsonism". *Nature* 392 (6676): 605-608. doi:10.1038/33416. PMID 9560156. Matsumine H, Yamamura Y, Hattori N, Kobayashi T, Kitada T, Yoritaka A, Mizuno Y (April 1998). "A microdeletion of D6S305 in a family of autosomal recessive juvenile parkinsonism (PARK2)". *Genomics* 49 (1): 143-146. doi:10.1006/geno.1997.5196. PMID 9570960. The protein is a component of a multiprotein E3 ubiquitin ligase complex which in turn is part of the ubiquitin-proteasome system that mediates the targeting of proteins for degradation. Mutations in the PARK2 gene are known to cause a familial form of Parkinson's disease known as autosomal recessive juvenile Parkinson's disease (AR-JP).

"Ligase" as used herein, is an enzyme that can catalyze the joining of two or more compounds or biomolecules by bonding them together with a new chemical bond. The "ligation" of the two usually with accompanying hydrolysis of a small chemical group dependent to one of the larger compounds or biomolecules, or the enzyme catalyzing the linking together of two compounds, e.g., enzymes that catalyze joining of groups C—O, C—S, C—N, etc. Ubiquitin-protein (E3) ligases are a large family of highly diverse enzymes selecting proteins for ubiquitination.

"Ub Ligases" are involved in disease pathogenesis for oncology, inflammation & infectious disease. E3 ligase belonging to the RING-between-RING (RBR) family of E3 ligases containing both canonical RING domains and a catalytic cysteine residue usually restricted to HECT E3 ligases; termed 'RING/HECT hybrid' enzymes. Mutations in Parkin linked to Parkinson's disease, cancer and mycobacterial infection. Parkin is recognized as a neuroprotective protein with a role in mitochondrial integrity. Human genetic data implicate loss of Parkin activity as a mechanism for pathogenesis of Parkinson's disease (PD).

"Zinc Finger (ZnF) Domain" as used herein relates to a protein structure characterized by coordinating zinc ions to stabilize the functional activity. ZnF stabilize the binding of Ub, Deubiquitinating Enzymes (DUBs), and Ligases (E3) in the UPS.

The present disclosure provides, in part, compositions and methods for treating, preventing, inhibiting, or delaying central nervous system degeneration. In particular, the present disclosure provides a gene therapy construct comprising a parkin (E3 ubiquitin protein ligase (PARK2)) gene or functional fragment or variant thereof, and methods of delivering the construct to a subject.

Parkin

Parkin consists of a ubiquitin-like (Ubl) domain and a 60-amino acid linker followed by RING0, a zinc finger unique to parkin (13), and three additional zinc finger domains characteristic of the RBR family. Parkin plays a role in the machinery that breaks down and degrades proteins in the cells by tagging damaged and excess proteins with ubiquitin. Parkin may also trigger the destruction of dysfunctional mitochondria, act as a tumor suppressor protein, regulate synaptic vesicles from nerve cells, and enhance cell survival by suppressing both mitochondria-dependent and mitochondria-independent apoptosis.

In some embodiments, a parkin (PARK2) variant of the present disclosure comprises one or more nucleotide mutations. In some embodiments, the parkin (PARK2) variant comprising one or more nucleotide mutations encodes a polypeptide comprising one or more amino acid substitutions, deletions, or additions. In some embodiments, the one or more amino acid substitutions replaces the wild type residue with a tyrosine.

In some embodiments, the present disclosure provides a parkin (PARK2) variant comprising one or more nucleotide mutations in the ubiquitin-like domain. In some embodiments, the present disclosure provides a parkin (PARK2) variant comprising one or more nucleotide mutations in a domain that disrupts a zinc-finer. In some embodiments, the present disclosure provides a parkin (PARK2) variant comprising one or more nucleotide mutations in an area that disrupts the interface between two zinc-finger domains. In some embodiments, the present disclosure provides a parkin (PARK2) variant comprising one or more nucleotide mutations in the RING0, RING1, and/or RING2 domains. In some embodiments, the present disclosure provides a parkin (PARK2) variant comprising one or more nucleotide mutations in the Ubl, RING0, RING1, and/or RING2 domains.

In some embodiments, the parkin (PAK2) variant demonstrates increased activity compared to a wild type parkin (e.g. a polypeptide encoded by SEQ ID NO: 1). In some embodiments, the parkin (PARK2) variant demonstrates increased ubiquitination compared to ubiquitination by a wild type parkin. In some embodiments, the variant demonstrates increased auto-ubiquitination compared to a wild type parkin. In some embodiments, the variant demonstrates increased inhibition of parkin polypeptide activity compared to a wild type parkin. In some embodiments, the variant demonstrates increased auto-inhibition of parkin polypeptide activity compared to a wild type parkin.

In some embodiments, the variant parkin that demonstrates increased activity compared to a wild type parkin is a polypeptide having the amino acid sequence of any one of SEQ ID NOs: 4, 6, and 8. In some embodiments, the parkin variant that demonstrates increased auto-ubiquitination compared to wild type parkin is a polypeptide having the amino acid sequence of any one of SEQ ID NOs: 4, 6, and 8. In some embodiments, the PARK2 variant encoding a variant parkin polypeptide having increased activity compared to a wild type parkin has a polynucleotide sequence of any one of SEQ ID NOs: 3, 4, and 7. In some embodiments, the PARK2 variant encoding a variant parkin polypeptide having increased auto-ubiquitination compared to wild type parkin has a polynucleotide sequence of any one of SEQ ID NOs: 3, 5, and 7.

In some embodiments, the present disclosure provides a polynucleotide sequence at least 75% identical to any one of SEQ ID NOs: 1, 3, 5, and/or 7. In some embodiments, the present disclosure provides a polynucleotide sequence about 75% to about 99.9% identical to any one of SEQ ID NOs: 1, 3, 5, and/or 7. In some embodiments, the present disclosure provides a polynucleotide sequence about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 98%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% to any one of SEQ ID NOs: 1, 3, 5, and/or 7. In some embodiments, the polynucleotide is DNA, cDNA, or RNA. In some embodiments, the polynucleotide is codon-optimized.

In some embodiments, the present disclosure provides gene therapy constructs comprising a polynucleotide sequence of one or more of SEQ ID NOs: 1, 3, 5, and/or 7. In some embodiments, the present disclosure provides gene therapy constructs comprising a polynucleotide sequence at least 75% identical to one or more of SEQ ID NOs: 1, 3, 5, and/or 7. In some embodiments, the present disclosure provides a gene therapy construct comprising a polynucleotide sequence about 75% to about 99.9% identical to one or more of SEQ ID NOs: 1, 3, 5, and/or 7. In some embodiments, the present disclosure provides a gene therapy construct comprising a polynucleotide sequence about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 98%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% to one or more of SEQ ID NOs: 1, 3, 5, and/or 7. In some embodiments, the polynucleotide is DNA, cDNA, or RNA. In some embodiments, the polynucleotide is codon-optimized.

In some embodiments, the present disclosure provides a polynucleotide sequence of any one of SEQ ID NOs: 1, 3, 5, and/or 7 comprising one or more nucleotide substitutions, mutations, deletions, additions, and/or truncations. In some embodiments, between about 1-20 or more nucleotides are mutated, substituted, deleted, added, and/or truncated. In some embodiments, about 1, about 2, about 3, about 4, about 5, about 6, about 7, about 8, about 9, about 10, about 11, about 12, about 13, about 14, about 15, about 16, about 17, about 18, about 19, or about 20 or more nucleotides are mutated, substituted, deleted, added, and/or truncated. In some embodiments, the polynucleotide sequence is extended or truncated at only one end. In some embodiments, the polynucleotide sequence is extended or truncated at both ends. In some embodiments, the polynucleotide sequence is extended at one end and truncated at the other.

In some embodiments, the present disclosure provides a gene therapy construct comprising a polynucleotide sequence of one or more of SEQ ID NOs: 1, 3, 5, and/or 7 comprising one or more nucleotide substitutions, mutations, deletions, additions, and/or truncations. In some embodiments, between about 1-20 or more nucleotides are mutated, substituted, deleted, added, and/or truncated. In some embodiments, about 1, about 2, about 3, about 4, about 5, about 6, about 7, about 8, about 9, about 10, about 11, about 12, about 13, about 14, about 15, about 16, about 17, about 18, about 19, or about 20 or more nucleotides are mutated, substituted, deleted, added, and/or truncated. In some embodiments, the polynucleotide sequence is extended or truncated at only one end. In some embodiments, the polynucleotide sequence is extended or truncated at both ends. In some embodiments, the polynucleotide sequence is extended at one end and truncated at the other.

In some embodiments, the present disclosure provides a polynucleotide sequence of any of SEQ ID NOs: 49-52. In some embodiments, the present disclosure provides a polynucleotide sequence at least 75% identical to any one of SEQ ID NOs: 49-52. In some embodiments, the present disclosure provides a polynucleotide sequence about 75% to about 99.9% identical to any one of SEQ ID NOs: 49-52. In some embodiments, the present disclosure provides a polynucleotide sequence about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 98%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% to any one of SEQ ID NOs: 49-52. In some embodiments, the polynucleotide is DNA, cDNA, or RNA. In some embodiments, the polynucleotide is codon-optimized.

In some embodiments, the present disclosure provides gene therapy constructs comprising a polynucleotide sequence of one or more of SEQ ID NOs: 49-52. In some embodiments, the present disclosure provides gene therapy constructs comprising a polynucleotide sequence at least 75% identical to one or more of SEQ ID NOs: 49-52. In some embodiments, the present disclosure provides a gene therapy construct comprising a polynucleotide sequence about 75% to about 99.9% identical to one or more of SEQ ID NOs: 49-52. In some embodiments, the present disclosure provides a gene therapy construct comprising a polynucleotide sequence about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 98%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% to one or more of SEQ ID NOs: 49-52. In some embodiments, the polynucleotide is DNA, cDNA, or RNA. In some embodiments, the polynucleotide is codon-optimized.

In some embodiments, the present disclosure provides a polypeptide having the amino acid sequence of any one of SEQ ID NOs: 2, 4, 6, and/or 8. In some embodiments, the present disclosure provides a polypeptide having an amino acid sequence at least 75% identical to any one of SEQ ID NOs: 2, 4, 6, and/or 8. In some embodiments, the present disclosure provides a polypeptide having an amino acid sequence about 75% to about 99.9% identical to any one of SEQ ID NOs: 2, 4, 6, and/or 8. In some embodiments, the present disclosure provides a polypeptide having an amino acid sequence about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 98%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% to any one of SEQ ID NOs: 2, 4, 6, and/or 8.

In some embodiments, the present disclosure provides a gene therapy construct comprising a parkin gene encoding the amino acid sequence of one or more of SEQ ID NOs: 2, 4, 6, and/or 8. In some embodiments, the present disclosure provides a gene therapy construct comprising a parkin gene encoding an amino acid sequence at least 75% identical to one or more of SEQ ID NOs: 2, 4, 6, and/or 8. In some embodiments, the present disclosure provides a gene therapy construct comprising a parkin gene encoding an amino acid sequence about 75% to about 99.9% identical to one or more of SEQ ID NOs: 2, 4, 6, and/or 8. In some embodiments, the present disclosure provides a gene therapy construct comprising a parkin gene encoding an amino acid sequence about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 98%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% to one or more of SEQ ID NOs: 2, 4, 6, and/or 8. In some embodiments, the present disclosure provides a polypeptide having the amino acid sequence of any one of SEQ ID NOs: 2, 4, 6, and/or 8 comprising one or more amino acid substitutions, mutations, deletions, additions, and/or truncations. In some embodiments, between about 1 and 7 or more amino acid residues are substituted, mutated, deleted, added, and/or truncated. In some embodiments, about 1, about 2, about 3, about 4, about 5, about 6, about 7, or more amino acid residues are substituted, mutated, deleted, added, and/or truncated. In some embodiments, the amino acid sequence is extended or truncated at the C-terminus. In some embodiments, the amino acid sequence is extended or truncated at the N-terminus. In some embodiments, the amino acid sequence is extended or truncated at both the N- and the C-terminus. In some embodiments, the amino acid sequence is extended at the N-terminus and truncated at both the C-terminus. In some embodiments, the amino acid sequence is extended at the C-terminus and truncated at both the N-terminus.

In some embodiments, the present disclosure provides a gene therapy construct comprising a parkin gene encoding the amino acid sequence of one or more of SEQ ID NOs: 2, 4, 6, and/or 8 comprising one or more amino acid substitutions, mutations, deletions, additions, and/or truncations. In some embodiments, between about 1 and 7 or more amino acid residues are substituted, mutated, deleted, added, and/or truncated. In some embodiments, about 1, about 2, about 3, about 4, about 5, about 6, about 7, or more amino acid residues are substituted, mutated, deleted, added, and/or truncated. In some embodiments, the amino acid sequence is extended or truncated at the C-terminus. In some embodiments, the amino acid sequence is extended or truncated at the N-terminus. In some embodiments, the amino acid sequence is extended or truncated at both the N- and the C-terminus. In some embodiments, the amino acid sequence is extended at the N-terminus and truncated at both the C-terminus. In some embodiments, the amino acid sequence is extended at the C-terminus and truncated at both the N-terminus.

In some embodiments, the present disclosure provides a parkin (PARK2) variant polypeptide comprising a mutation altering at least one amino acid residue to a tyrosine of wild type Parkin (e.g. the polypeptide encoded by SEQ ID NO: 1). In some embodiments, the present disclosure provides a parkin (PARK2) variant polypeptide comprising at least one phenylanine and/or tryptophan residue substituted with a tyrosine of wild type Parkin. In some embodiments, the present disclosure provides a parkin (PARK2) variant polypeptide comprising mutations at one or more of the 146, 208, 183, 403, 457, and/or 463 residues of wild type Parkin. In some embodiments, the present disclosure provides a parkin (PARK2) variant polypeptide comprising mutations at F146, W183, F208, W403, C457, W462, and/or F463 of wild type Parkin. In some embodiments, the present disclosure provides a parkin (PARK2) variant polypeptide comprising one or more of F146A or F146Y, W183Y, F208Y, W403A, and/or F463Y of wild type Parkin. In some embodiments, the present disclosure provides a parkin (PARK2) variant polypeptide comprising one or more of W183Y, F208Y, and/or F463Y of wild type Parkin.

In some embodiments, the present disclosure provides a parkin (PARK2) variant polypeptide comprising W183A, W183R, W183N, W183D, W183C, W183E, W183Q, W183G, W183H, W1831, W183L, W183K, W183M, W183F, W183P, W183S, W183T, W183Y or W183V of wild type Parkin.

In some embodiments, the present disclosure provides a parkin (PARK2) variant polypeptide comprising F208A, F208R, F208N, F208D, F208C, F208E, F208Q, F208G, F208H, F208L, F208L, F208K, F208M, F208P, F208S, F208T, F208W, F208Y or F208V of wild type Parkin. In some embodiments, the present disclosure provides a parkin (PARK2) variant polypeptide comprising F463A, F463R, F463N, F463D, F463C, F463E, F463Q, F463G, F463H, F463L, F463L, F463K, F463M, F463P, F463S, F463T, F463W, F463Y or F463V of wild type Parkin.

Recombinant Gene Therapy Constructs

The recombinant gene therapy construct of the present disclosure may include gene regulatory elements. In some embodiments, the recombinant gene therapy construct comprises a polynucleotide comprising, in the following 5' to 3' order, a eukaryotically active promoter sequence and the sequence encoding the wild-type parkin, or functional fragment or variant thereof. The sequence encoding the wild-type parkin, or functional fragment or variant thereof, is operably linked to the eukaryotically active promoter sequence.

In some embodiments, the present disclosure provides polynucleotide sequences comprising a polynucleotide sequence of one or more of SEQ ID NOs: 49-52 or variants thereof as disclosed herein. In some embodiments, the present disclosure provides gene therapy constructs comprising a polynucleotide sequence of one or more of SEQ ID NOs: 49-52 or variants thereof as disclosed herein.

In some embodiments, the recombinant gene therapy construct comprises a minigene. In some embodiments, the minigene comprises, at a minimum, a parkin or variant parkin as disclosed herein, and its regulatory sequences, and AAV inverted terminal repeats (ITRs).

In some embodiments, the recombinant gene therapy construct comprises one or more regulatory elements, which may be operably linked to the parkin or variant parkin nucleotide sequence to permit transcription, translation, and/or expression in a cell transfected with the plasmid vector or infected with the virus produced using the methods disclosed herein.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. Expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer, the SV40 promoter, the dihydrofolate reductase promoter, the β-actin promoter, the phosphoglycerol kinase (PGK) promoter, and the EF1α promoter. In some embodiments, the recombinant gene therapy construct comprises a ubiquitous promotor selected from the group including but not limited to, CMV, CAG, UBC, PGK, EF1-alpha, GAPDH, SV40, HBV, and chicken beta-actin (CBA) promoters.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system; the ecdysone insect promoter, the tetracycline-repressible system, the tetracycline-inducible system, the RU486-inducible system and the rapamycin-inducible system. Still other types of inducible promoters which may be useful in this context are those which are regulated by a specific physiological state, e.g., temperature, acute phase, a particular differentiation state of the cell, or in replicating cells only.

In some embodiments, the native promoter for the parkin gene is used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the promoter is a tissue-specific promoter. In some embodiments, the promoter is a neuronal or glial specific promoter. In some embodiments, the recombinant gene therapy construct comprises one or more of a neuron-specific promoter, including but not limited to, hSYN1 (human synapsin), INA (alpha-internexin), NES (nestin), TH (tyrosine hydroxylase), FOXA2 (Forkhead box A2), CaMKII (calmodulin-dependent protein kinase II), and NSE (neuron-specific enolase) promoters.

In some embodiments, the recombinant gene therapy construct comprises an enhancer. In some embodiments, the enhancer is derived from a virus or bacteria. In some embodiments, the enhancer is derived from cytomegalovirus (CMV). In some embodiments, the enhancer is CMV.IE.

In some embodiments, the recombinant gene therapy construct comprises an intron. In some embodiments, the intron is derived from a beta-actin. In some embodiments, the intron is a CBA intron. In some embodiments, the recombinant gene therapy construct comprises a poly-A signal. In some embodiments, the poly-A signal is an early poly-A sequence. In some embodiments, poly-A sequence is an SV40 early poly-A sequence.

In some embodiments, the recombinant gene therapy construct of the present disclosure comprises one or more selectable markers or reporter genes may include sequences encoding geneticin, hygromicin or purimycin resistance, among others.

The minigene can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids (or other vectors carrying the 5' AAV ITR-heterologous molecule-3'ITR) contain sequences permitting replication of the minigene in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the minigene is transfected into the cell, where it may exist transiently. Alternatively, the minigene may be stably integrated into the genome of the host cell, either chromosomally or as an episome. In some embodiments, the minigene may be present in multiple copies, optionally in head-to-head, head-to-tail, or tail-to-tail concatamers. Suitable transfection techniques are known and may readily be utilized to deliver the minigene to the host cell.

Generally, when delivering the vector comprising the minigene by transfection, the vector is delivered in an amount from about 5 µg to about 100 µg DNA, and preferably about 10 to about 50 µg DNA to about $1 \times 10^4$ cells to about $1 \times 10^{13}$ cells, and preferably about $10^5$ cells. However, the relative amounts of vector DNA to host cells may be adjusted, taking into consideration such factors as the selected vector, the delivery method and the host cells selected.

In some embodiments, the present disclosure provides host cell containing a polynucleotide sequence of one or more of SEQ ID NOs: 49-52 or variants thereof as disclosed herein. In some embodiments, the present disclosure provides host cell containing a polynucleotide sequence of one or more of SEQ ID NOs: 49-52 or variants thereof as disclosed herein.

Adeno-Associated Virus Vectors

Adeno-associated virus (AAV) is a replication-deficient parvovirus possessing a single-stranded DNA genome that is about 4.7 kb in length and includes two 145-nucleotide inverted terminal repeat (ITRs). Cis-acting sequences directing viral DNA replication (rep), encapsidation/packaging and host cell chromosome integration are contained within the AAV ITRs. Three AAV promoters (named p5, p19, and p40) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep78, rep68, rep52, and rep40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells (e.g. gene therapy). AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Moreover, AAV is extremely stable, including at conditions used to inactivate adenovirus (56° to 65° C. for several hours), thus making cold preservation of AAV less critical. AAV may even be lyophilized. Finally, AAV-infected cells are not resistant to superinfection.

AAV vectors are especially suited as a CNS gene therapy vector as they can mediate gene transfer to both mitotic and post-mitotic cells, are neurotropic, can exist stably in an episomal state, with little or no pathogenicity or cytotoxicity.

AAV vectors are, advantageously, non-replicating vectors that rarely integrates into the host genome, and thus are generally the safest viral vector of choice for gene therapy to the brain. Further, the different serotypes of AAV vectors allow targeting of the gene therapy to the desired portions of the brain. For example, AAV 8 and AAV9 primarily target the neurons, and AAV4 preferentially infects astrocytes and ependymal cells.

In some embodiments, the gene therapy construct of the present disclosure comprise AAV sequences. In some embodiments, the gene therapy construct of the present disclosure is an AAV vector. In some embodiments, the AAV vector is of the serotype AAV1, AAV2, AAV4, AAV5, AAV6, AAV7, AAV8, AAV9, AAV10, AAV11, AAV12, AAV13, or AAVrhIO. In some embodiments, the AAV comprises a capsid protein having at least 95% identity to a wild-type VP1, VP2, or VP3 capsid protein. In some embodiments, the AAV vector or portion thereof is encoded by any one of SEQ ID NOs: 9-20 or a variant or fragment thereof. In some embodiments, the AAV vector or portion thereof is encoded by SEQ ID NO: 13 or a variant or fragment thereof.

In some embodiments, the present disclosure provides a polynucleotide sequence at least 75% identical to any one of SEQ ID NOs: 9-20 or a variant or fragment thereof. In some embodiments, the present disclosure provides a polynucleotide sequence about 75% to about 99.9% identical to any one of SEQ ID NOs: 9-20. In some embodiments, the present disclosure provides a polynucleotide sequence about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 98%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% to any one of SEQ ID NOs: 19-20. In some embodiments, the polynucleotide is DNA, cDNA, or RNA. In some embodiments, the polynucleotide is codon-optimized.

In some embodiments, the polynucleotide sequence encodes an AAV rep protein or a variant or fragment thereof. In some embodiments, the AAV rep protein is rep 40, rep 58, rep 68, or rep 78 or a variant or fragment thereof. In some embodiments, the rep protein is a polypeptide having the amino acid sequence of any one of SEQ ID NOs: 21-35 or a variant or fragment thereof. In some embodiments, the rep protein is a polypeptide having the amino acid sequence of SED ID NO: 29, or a variant or fragment thereof. In some embodiments, the present disclosure provides a polypeptide having an amino acid sequence at least 75% identical to any one of SEQ ID NOs: 21-35. In some embodiments, the present disclosure provides a polypeptide having an amino acid sequence about 75% to about 99.9% identical to any one of SEQ ID NOs: 21-35. In some embodiments, the present disclosure provides a polypeptide having an amino acid sequence about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 98%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% to any one of SEQ ID NOs: 21-35.

In some embodiments, the polynucleotide sequence encodes an AAV VP protein or a variant or fragment thereof. In some embodiments, the AAV VP protein is VP1 or VP3 or a variant or fragment thereof. In some embodiments, the VP protein is a polypeptide having the amino acid sequence of any one of SEQ ID NOs: 36-48 or a variant or fragment thereof. In some embodiments, the rep protein is a polypeptide having the amino acid sequence of SED ID NO: 41, or a variant or fragment thereof. In some embodiments, the present disclosure provides a polypeptide having an amino acid sequence at least 75% identical to any one of SEQ ID NOs: 36-48. In some embodiments, the present disclosure provides a polypeptide having an amino acid sequence about 75% to about 99.9% identical to any one of SEQ ID NOs: 36-48. In some embodiments, the present disclosure provides a polypeptide having an amino acid sequence about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 98%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% to any one of SEQ ID NOs: 36-48.

In some embodiments, the AAV vector is AAV5. In some embodiments, the AAV5 vector transduces both neurons and glial cells in the brain. In some embodiments, administration of an AAV5 vector comprising a parkin nucleotide sequence disclosed herein allows expression of the parkin or parkin variant polypeptide in both neurons and glial cells. In some embodiments, expression of the parkin or parkin variant polypeptide in both neurons and glial cells increases the therapeutic effect of the gene therapy compared with expression of parkin or a parkin variant polypeptide in neurons or glial cells alone. In some embodiments, the neurons are dopaminergic neurons. In some embodiments, the neurons are oligodendrocytes. In some embodiments, the glial cells are astrocytes.

Methods of Treatment

Ubiquitination is crucial for a plethora of physiological processes, including cell survival and differentiation and innate and adaptive immunity. Proteins are built-up to cater for the structural and biochemical requirements of the cell and they are also broken-down in a highly regulated process serving more purposes than just destruction and space management. Proteins have different half-lives, determined by properties inherent to each protein substrate. Some will be long-lived, while other will rapidly be degraded. Proteolysis not only enables the cell to dispose of misfolded or damaged proteins, but also to fine-tune the concentration of essential proteins within the cell, such as the proteins involved in the cell cycle. This rapid, highly specific degradation can be achieved through the addition of at least four ubiquitin molecules to a target protein. Protein degradation is dependent on the post-translational addition of ubiquitin to the epsilon amino-group of specific lysine residues in a process called ubiquitination.

In recent years, considerable progress has been made in the understanding of the molecular action of ubiquitin in signaling pathways and how alterations in the ubiquitin system lead to the development of distinct human diseases. It has been shown that ubiquitination plays a role in the onset and progression of cancer, metabolic syndromes, neurodegenerative diseases, autoimmunity, inflammatory disorders, infection and muscle dystrophies (Popovic et al. *Nature Medicine* 20, 1242-1253 (2014)).

Ubiquitin-protein (E3) ligases are a large family of enzymes that select various proteins for ubiquitination. These ubiquitin ligases, called "Ub ligases" are known to have a role in various diseases and conditions, including but not limited to, cancer, inflammation and infectious diseases.

One specific Ub ligase is parkin ligase. Parkin ligase is a component of a multiprotein "E3" ubiquitin ligase complex, which in turn is part of the ubiquitin-proteasome system that mediates the targeting of proteins for degradation. Mutations in parkin ligase are linked to various diseases, such as Parkinson's disease, cancer and mycobacterial infection. Parkin ligase is thus an attractive target for therapeutic intervention.

In some aspects, the disclosure provides a method of inhibiting degeneration or death of a dopaminergic neuron comprising a mutation in a PARK2 gene associated with a Parkinson's Disease (PD). In some aspects, the method comprises contacting a neuron with a recombinant gene therapy construct comprising a polynucleotide encoding a wild-type parkin protein (e.g. SEQ ID NO: 2) expressed by a wild-type version of the PARK2 gene (e.g. SEQ ID NO: 1), or a functional variant or fragment thereof. Following contact with the recombinant gene therapy vector, the neuron expresses the wild-type protein, or functional variant or fragment thereof. In some embodiments, the functional variant of the wild type PARK2 gene is one or more of the polynucleotide sequences of SEQ ID NOs: 3, 5, and/or 7. In some embodiments, the functional variant of the wild type PARK2 gene is one or more of the variants of the polynucleotide sequences of any of SEQ ID NOs: 1, 3, 5, and 7 as disclosed herein. In some embodiments, the functional variant of the wild type PARK2 gene encodes a variant polypeptide having the amino acid sequence of any one of SEQ ID NOs: 2, 4, 6, and 8 or variants thereof as disclosed herein.

In some embodiments, administration of a gene construct of the present disclosure to a subject treats, prevents, delays, ameliorates, or reduces the incidence of one or more diseases or ailments selected from the group consisting of Alzheimer's Dementia, Parkinson's disease, Huntington Disease, Amyotrophic Lateral Sclerosis (ALS), Freidreich's ataxia, Spinocerebellar Ataxia, Multiple Systems Atrophy, PSP, Tauopathy, Diffuse Lewy Body Disease, Lewy Body dementia, any disorder characterized by abnormal accumulation of α-synuclein, disorders of the aging process, stroke, bacterial infection, viral infection, Mitochondrial related disease, mental retardation, deafness, blindness, diabetes, obesity, cardiovascular disease, multiple sclerosis, Sjogrens syndrome, lupus, glaucoma, including pseudoexfoliation glaucoma, Leber's Hereditary Optic Neuropathy, and rheumatoid arthritis.

In some embodiments, after transfection with a gene therapy construct of the instant disclosure, the transfected neuron and/or glial cell expresses a parkin or variant parkin polypeptide as disclosed herein. In some embodiments, after transfection with a gene therapy construct of the instant disclosure, the transfected neuron and/or glial cell expresses more parkin polypeptide as disclosed herein compared to that of a neuron and/or glial cell in a PARK2-deficient patient, or the neuron of the same patient before transfection. In some embodiments, the transfected neuron and/or glial cell expresses between about 1% to about 300% or more parkin or a functional variant thereof compared to that of a neuron and/or glial cell in a PARK2-deficient patient, or the neuron and/or glial cell of the same patient before transfection. In some embodiments, the transfected neuron and/or glial cell expresses about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more parkin or a functional variant thereof compared to that of a neuron and/or glial cell in a PARK2-deficient patient, or the neuron and/or glial cell of the same patient before transfection. In some embodiments, the transfected neuron and/or glial cell expresses more parkin or a functional variant thereof compared to that of a neuron and/or glial cell in a PARK2-deficient patient, or the neuron and/or glial cell of the same patient before transfection for about 1 week to about 10 years or more. In some embodiments, the transfected neuron and/or glial cell expresses more parkin or a functional variant thereof compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more. In some embodiments, the transfected neuron and/or glial cell expresses about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more parkin or a functional variant thereof compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more.

In some embodiments, after transfection with a gene therapy construct of the instant disclosure, the neuron and/or glial cell expressing a parkin polypeptide or a functional variant thereof as disclosed herein comprises a reduced amount of Lewy bodies compared to that of a neuron and/or glial cell in a PARK2-deficient patient, or the neuron and/or glial cell of the same patient before transfection. In some embodiments, the transfected neuron and/or glial cell demonstrates a reduction in the production of Lewy bodies between about 1% to about 300% or more compared to that of a neuron and/or glial cell in a PARK2-deficient patient, or the neuron and/or glial cell of the same patient before transfection. In some embodiments, production of Lewy bodies in the transfected neuron and/or glial cell decreases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to that of a neuron and/or glial cell in a PARK2-deficient patient, or the neuron and/or glial cell of the same patient before transfection. In some embodiments, production of Lewy bodies in the transfected neuron and/or glial cell decreases compared to that of a neuron and/or glial cell in a PARK2-deficient patient, or the neuron and/or glial cell of the same patient before transfection for about 1 week to about 10 years or more. In some embodiments, production of Lewy bodies in the transfected neuron and/or glial cell decreases compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more. In some embodiments, production of Lewy bodies in the transfected neuron and/or glial cell decreases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more.

In some embodiments, after transfection with a gene therapy construct of the instant disclosure, the neuron and/or glial cell expressing a parkin polypeptide or functional variant thereof as disclosed herein expresses a reduced amount of alpha-synuclein compared to that of a neuron and/or glial cell in a PARK2-deficient patient, or the neuron and/or glial cell of the same patient before transfection. In some embodiments, expression of alpha-synuclein in the transfected neuron and/or glial cell decreases between about 1% to about 300% or more compared to that of a neuron and/or glial cell in a PARK2-deficient patient, or the neuron and/or glial cell of the same patient before transfection. In some embodiments, expression of alpha-synuclein in the transfected neuron and/or glial cell decreases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to that of a neuron and/or glial cell in a PARK2-deficient patient, or the neuron and/or glial cell of the same patient before transfection. In some embodiments, expression of alpha-synuclein in the transfected neuron and/or glial cell decreases compared to that of a neuron and/or glial cell in a PARK2-deficient patient, or the neuron and/or glial cell of the same patient before transfection for about 1 week to about 10 years or more. In some embodiments, expression of alpha-synuclein in the transfected neuron and/or glial cell decreases compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more. In some embodiments, the expression of alpha-synuclein in the transfected neuron and/or glial cell decreases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more.

In some embodiments, after transfection with a gene therapy construct of the instant disclosure, the transfected neuron and/or glial cell expressing a parkin polypeptide or functional variant thereof as disclosed herein expresses a reduced amount of monoamine oxidases compared to that of a neuron and/or glial cell in a PARK2-deficient patient, or the neuron and/or glial cell of the same patient before transfection. In some embodiments, expression of monoamine oxidases in the transfected neuron and/or glial cell decreases between about 1% to about 300% or more compared to that of a neuron and/or glial cell in a PARK2-deficient patient, or the neuron and/or glial cell of the same patient before transfection. In some embodiments, expression of monoamine oxidases decreases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to that of a neuron and/or glial cell in a PARK2-deficient patient, or the neuron and/or glial cell of the same patient before transfection. In some embodiments, expression of monoamine oxidases in the transfected neuron and/or glial cell decreases compared to that of a neuron and/or glial cell in a PARK2-deficient patient, or the neuron and/or glial cell of the same patient before transfection for about 1 week to about 10 years or more. In some embodiments, expression of monoamine oxidases in the transfected neuron and/or glial cell decreases compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more. In some embodiments, the expression of monoamine oxidases in the transfected neuron and/or glial cell decreases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more.

In some embodiments, after transfection with a gene therapy construct of the instant disclosure, the transfected neuron and/or glial cell produces and/or releases an increased amount of dopamine compared to that of a neuron and/or glial cell in a PARK2-deficient patient, or the neuron and/or glial cell of the same patient before transfection. In some embodiments, the transfected neuron and/or glial cell produces and/or releases an increased amount of dopamine due to increased Tyrosine Hydroxylase (TH) levels due to expression of PARK-2 in the transfected neuron and/or glial cell. In some embodiments, production of dopamine in the transfected neuron and/or glial cell increases between about 1% to about 300% or more compared to that of a neuron and/or glial cell in a PARK2-deficient patient, or the neuron and/or glial cell of the same patient before transfection. In some embodiments, production of dopamine in the transfected neuron and/or glial cell increases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to that of a neuron and/or glial cell in a PARK2-deficient patient, or the neuron and/or glial cell of the same patient before transfection. In some embodiments, production of dopamine in the transfected neuron and/or glial cell increases compared to that of a neuron and/or glial cell in a PARK2-deficient patient, or the neuron and/or glial cell of the same patient before transfection for about 1 week to about 10 years or more. In some embodiments, production of dopamine in the transfected neuron and/or glial cell increases in the transfected neuron and/or glial cell compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more. In some embodiments, production of dopamine in the transfected neuron and/or glial cell increases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more.

In some embodiments, after transfection with a gene therapy construct of the instant disclosure, the transfected neuron and/or glial cell produces an increased amount of Tyrosine Hydroxylase (TH) compared to that of a neuron and/or glial cell in a PARK2-deficient patient, or the neuron of the same patient before transfection. See for example, Manfredsson et al. (2007), the contents of which are incorporated herein in their entireties for all purposes. In some embodiments, production of TH in the transfected neuron and/or glial cell increases between about 1% to about 300% or more compared to that of a neuron and/or glial cell in a PARK2-deficient patient, or the neuron and/or glial cell of the same patient before transfection. In some embodiments, production of TH in the transfected neuron increases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to that of a neuron and/or glial cell in a PARK2-deficient patient, or the neuron and/or glial cell of the same patient before transfection. In some embodiments, production of TH in the transfected neuron and/or glial cell increases compared to that of a neuron and/or glial cell in a PARK2-deficient patient, or the neuron and/or glial cell of the same patient before transfection for about 1 week to about 10 years or more. In some embodiments, production of TH in the transfected neuron and/or glial cell increases in the transfected neuron compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more. In some embodiments, production of TH in the transfected neuron and/or glial cell increases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more In some embodiments, after transfection with a gene therapy construct of the instant disclosure, the transfected neuron and/or glial cell demonstrates increased autophagy compared to that of a neuron and/or glial cell in a PARK2-deficient patient, or the neuron and/or glial cell of the same patient before transfection. In some embodiments, autophagy in the transfected neuron and/or glial cell increases between about 1% to about 300% or more compared to that of a neuron and/or glial cell in a PARK2-deficient patient, or the neuron and/or glial cell of the same patient before transfection. In some embodiments, autophagy in the transfected neuron and/or glial cell increases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to that of a neuron and/or glial cell in a PARK2-deficient patient, or the neuron and/or glial cell of the same patient before transfection. In some embodiments, autophagy in the transfected neuron and/or glial cell increases compared to that of a neuron and/or glial cell in a PARK2-deficient patient, or the neuron and/or glial cell of the same patient before transfection for about 1 week to about 10 years or more. In some embodiments, autophagy in the transfected neuron and/or glial cell increases in the transfected neuron compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more. In some embodiments, autophagy in the transfected neuron increases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to that of a neuron and/or glial cell in a PARK2-deficient patient, or the neuron and/or glial cell of the same patient before transfection for about 1 week, about 1 month, about 2 months, about 3 months, about 4 months, about 5 months, about 6 months, about 8 months, about 1 year, about 2 years, about 5 years, and/or about 10 years or more.

In some aspects the constructs of the present disclosure are administered to a patient displaying symptoms of and/or diagnosed with a central nervous system disease or disorder. In some aspects the constructs of the present disclosure are administered to a patient at risk of developing symptoms of and/or being diagnosed with a central nervous system disease or disorder. In some embodiments, the central nervous system disease or disorder is Parkinson's Disease. In some embodiments, the Parkinson's Disease is an early-onset Parkinson's Disease. In some embodiments, the patient bears a mutation or deletion in PARK2 gene. In some embodiments, the patient bears a heterozygous mutation or deletion in the PARK2 gene. In some embodiments, the patient bears a homozygous mutation or deletion in the PARK2 gene. In some embodiments, the mutation in the PARK2 gene results in a loss of function or a decrease in function of the expressed parkin polypeptide. In some embodiments, the mutation is an exon mutation, an exon deletion, stop codon, an intron mutation, an intron deletion, a splice variant, a point mutation, a frameshift mutation, a deletion mutation, a disrupter mutation, a mutation that decreases copy number, and/or a mutation that increases protein turnover.

In some embodiments, the patient bears a non-PARK2 mutation associated with the development of Parkinson's Disease. In some embodiments, the patient bears a mutation in one or more of the SNCA, PARK7, PINK1, and/or LRK2 genes. In some embodiments, the patient bears a mutation in PARK2 and in one or more of the SNCA, PARK7, PINK1, and/or LRK2 genes. In some embodiments, the mutations in the SNCA, PARK7, PINK1, and/or LRK2 genes are loss of function mutations. In some embodiments, the patient is heterozygous for the mutation in one or more of the SNCA, PARK7, PINK1, and/or LRK2 genes. In some embodiments, the patient is homozygous for the mutation in one or more of the SNCA, PARK7, PINK1, and/or LRK2 genes. In some embodiments, the mutation in one or more of the SNCA, PARK7, PINK1, and/or LRK2 genes is an exon mutation, an exon deletion, stop codon, an intron mutation, an intron deletion, a splice variant, a point mutation, a frameshift mutation, a deletion mutation, a disrupter mutation, a mutation that decreases copy number, and/or a mutation that increases protein turnover.

In some embodiments, administration of the pharmaceutical compositions and constructs of the present disclosure replaces one PARK2 gene in the patient's cell. In some embodiments, administration of the pharmaceutical compositions and constructs of the present disclosure replaces both PARK2 genes in the patient's cell. In some embodiments, administration of the pharmaceutical compositions and constructs of the present disclosure adds additional copies of the PARK2 gene in the patient's cell. In some embodiments, administration of the pharmaceutical compositions and constructs of the present disclosure adds between 1 and 10 additional PARK2 genes in the patient's cell. In some embodiments, administration of the pharmaceutical compositions and constructs of the present disclosure adds about 1, about 2, about 3, about 4, about 5, about 6, about 7, about 8, about 9, or about 10 additional PARK2 genes in the patient's cell.

In some aspects, administration of a construct of the present disclosure to a patient treats, improves, prevents, ameliorates, and/or delays one or more symptoms of Parkinson's Disease. In some embodiments, the one or more symptoms of Parkinson's Disease includes, but is not limited to, motor deficits, tremors, bradykinesia (slowed movement), rigid muscles, impaired posture and balance, loss of automatic movements, speech changes, writing changes, depression, swallowing problems, decreased cardiac function, sleep disorders, dementia, cognitive problems, emotional changes (e.g. fear, anxiety, or loss of motivation), blood pressure changes, fatigue, pain, involuntary movements, shuffling gait, dizziness, amnesia, confusion, voice box spasms, distorted sense of smell, jaw stiffness or reduced facial expression, and weight loss.

In some embodiments, after transfection with a gene therapy construct of the instant disclosure, treated patient demonstrates reduction in one or more symptoms of Parkinson's Disease compared to an untreated Parkinson's Disease patient or the same patient before treatment. In some embodiments, one or more symptoms of Parkinson's Disease are reduced between about 1% to about 300% or more compared to an untreated Parkinson's Disease patient or the same patient before treatment. In some embodiments, one or more symptoms of Parkinson's Disease is reduced by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to an untreated Parkinson's Disease patient or the same patient before treatment. In some embodiments, one or more symptoms of Parkinson's Disease are decreased compared to compared to an untreated Parkinson's Disease patient or the same patient before treatment for about 1 week to about 10 years or more. In some embodiments, one or more symptoms of Parkinson's Disease are decreased compared to an untreated Parkinson's Disease patient or the same patient before treatment for about 1 week, about 1 month, about 2 months, about 3 months, about 4 months, about 5 months, about 6 months, about 8 months, about 1 year, about 2 years, about 5 years, and/or about 10 years or more. In some embodiments, one or more symptoms of Parkinson's Disease is decreased by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to an untreated Parkinson's Disease patient or the same patient before treatment for about 1 week, about 1 month, about 2 months, about 3 months, about 4 months, about 5 months, about 6 months, about 8 months, about 1 year, about 2 years, about 5 years, and/or about 10 years or more.

In some embodiments, administration of a gene therapy construct of the present disclosure increases the number of dopaminergic neurons in the treated patient compared to an untreated Parkinson's Disease patient or the same patient before treatment. In some embodiments, the number of dopaminergic neurons in the treated patient increases between about 1% to about 300% or more compared to an untreated Parkinson's Disease patient or the same patient before treatment. In some embodiments, the number of dopaminergic neurons increases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more in a treated patient compared to an untreated Parkinson's Disease patient or the same patient before treatment. In some embodiments, the number of dopaminergic neurons increases compared to an untreated Parkinson's Disease patient or the same patient before treatment for about 1 week to about 10 years or more. In some embodiments, the number of dopaminergic neurons increases in an untreated Parkinson's Disease patient or the same patient before treatment for about 1 week, about 1 month, about 2 months, about 3 months, about 4 months, about 5 months, about 6 months, about 8 months, about 1 year, about 2 years, about 5 years, and/or about 10 years or more. In some embodiments, the number of dopaminergic neurons increases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to an untreated Parkinson's Disease patient or the same patient before treatment for about 1 week, about 1 month, about 2 months, about 3 months, about 4 months, about 5 months, about 6 months, about 8 months, about 1 year, about 2 years, about 5 years, and/or about 10 years or more.

In some embodiments, administration of a gene therapy construct of the present disclosure strengthens connections among dopaminergic neurons in the treated patient compared to an untreated Parkinson's Disease patient or the same patient before treatment. The strength or numbers of connections among dopaminergic neurons can be determined using the metabolic network analysis disclosed in Niethammer et al. (2018), the contents of which are incorporated herein in their entireties for all purposes. In some embodiments, the connection strength of dopaminergic neurons in the treated patient increases between about 1% to about 300% or more compared to an untreated Parkinson's Disease patient or the same patient before treatment. In some embodiments, the connection strength dopaminergic neurons increases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more in a treated patient compared to an untreated Parkinson's Disease patient or the same patient before treatment. In some embodiments, the connection strength of dopaminergic neurons increases compared to an untreated Parkinson's Disease patient or the same patient before treatment for about 1 week to about 10 years or more. In some embodiments, the connection strength of dopaminergic neurons increases in an untreated Parkinson's Disease patient or the same patient before treatment for about 1 week, about 1 month, about 2 months, about 3 months, about 4 months, about 5 months, about 6 months, about 8 months, about 1 year, about 2 years, about 5 years, and/or about 10 years or more. In some embodiments, the connection strength of dopaminergic neurons increases by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 90%, about 95%, about 99%, about 100%, about 200%, about 300% or more compared to an untreated Parkinson's Disease patient or the same patient before treatment for about 1 week, about 1 month, about 2 months, about 3 months, about 4 months, about 5 months, about 6 months, about 8 months, about 1 year, about 2 years, about 5 years, and/or about 10 years or more.

Pharmaceutical Compositions & Methods of Administration

The present disclosure provides pharmaceutical compositions comprising an AAV capsid incorporating a gene therapy construct of the present disclosure and one or more diluents, preservatives, stabilizers, carriers, and/or pharmaceutical excipients. In some embodiments, the preservatives include chlorobutanol, potassium sorbate, sorbic acid, sulfur dioxide, propyl gallate, the parabens, ethyl vanillin, glycerin, phenol, and parachlorophenol. In some embodiments, the stabilizers include gelatin and albumin. In some embodiments, the pharmaceutical composition is free of DNA and/or other cellular material.

The present gene therapy constructs are administered in sufficient amounts to transfect the cells and to provide sufficient levels of gene transfer and expression to provide a therapeutic benefit without undue adverse effects, or with medically acceptable physiological effects, which can be determined by those skilled in the medical arts.

The gene therapy constructs of the present disclosure may be administered using any appropriate route. In some embodiments, the gene therapy constructs of the present disclosure are administered directly to the brain. In some embodiments, the administration to the brain is local administration. In some embodiments, the gene therapy constructs of the present disclosure are administered to the substantia nigra.

In some embodiments, the gene therapy constructs of the present disclosure are administered to the cells in the brain that produce tyrosine hydroxylase (TH).

In some embodiments, local administration to the brain requires craniotomy and injection of a gene therapy construct of the present disclosure. In some embodiments, administration includes, but is not limited to, direct injection, injection into the cerebrospinal fluid (CSF), intrathecal injection, intravascular administration, cerebral, intrascisternal, inraputaminal, Intranigral, intrahippocampal, intrastiatal, intracerebroventricular, and intramuscular injection targeting motor and sensory neurons.

In some embodiments, the gene therapy construct injected is the naked polynucleotide. In some embodiments, the gene therapy construct injected is associated with one or more molecules (e.g. lipids, micelles, cationic polymers, etc.). In some embodiments, the gene therapy construct is associated with one or more proteins. In some embodiments, the one or more proteins includes a ferrying protein. In some embodiments, the one or more proteins includes a viral protein. In some embodiments, the viral protein is a capsid protein. In some embodiments, the gene therapy construct is packaged into a viral vector. In some embodiments, the viral vector is a herpes simplex vector, a lentiviral vector, an adeno-associated viral vector, or an adeno-associated vector. In some embodiments, the adeno-associated vector is AAV5.

In some embodiments, $1\times10^6$-$1\times10^{14}$ vector genomes per kilogram body mass of the subject (vg/kg) of the gene therapy construct of the present disclosure are administered to the subject. In some embodiments, $1\times10^6$-$1\times10^{14}$ vector genomes per kilogram body mass of the subject (vg/kg) of the gene therapy construct of the present disclosure are injected to the subject's brain. In some embodiments, $1\times10^6$-$1\times10^4$ vector genomes per kilogram body mass of the subject (vg/kg) of the gene therapy construct of the present disclosure are administered to the subject's CSF. In some embodiments, $1\times10^7$-$1\times10^8$ vector genomes per kilogram body mass of the subject (vg/kg) of the gene therapy construct of the present disclosure are administered to the subject. In some embodiments, $1\times10^7$-$1\times10^9$ vector genomes per kilogram body mass of the subject (vg/kg) of the gene therapy construct of the present disclosure are administered to the subject. In some embodiments, $1\times10^6$-$1\times10^{14}$, $1\times10^7$-$1\times10^{13}$, $1\times10^8$-$1\times10^{12}$, $1\times10^9$-$1\times10^{11}$, $1\times10^{10}$-$1\times10^{11}$, $1\times10^{11}$-$1\times10^{12}$, $1\times10^{12}$-$1\times10^{13}$, $1\times10^{13}$-$1\times10^{14}$ vector genomes per kilogram body mass of the subject (vg/kg) of the gene therapy construct of the present disclosure are administered to the subject.

In some embodiments, $1\times10^6$-$1\times10^{14}$ gc/mL of the gene therapy construct of the present disclosure are administered to the subject. In some embodiments, $1\times10^6$-$1\times10^4$ gc/mL of the gene therapy construct of the present disclosure are injected to the subject's brain. In some embodiments, $1\times10^6$-$1\times10^{14}$ gc/mL of the gene therapy construct of the present disclosure are administered to the subject's CSF. In some embodiments, $1\times10^7$-$1\times10^8$ gc/mL of the gene therapy construct of the present disclosure are administered to the subject. In some embodiments, $1\times10^7$-$1\times10^9$ gc/mL of the gene therapy construct of the present disclosure are administered to the subject. In some embodiments, $1\times10^6$-$1\times10^{14}$, $1\times10^7$-$1\times10^{13}$, $1\times10^8$-$1\times10^{12}$, $1\times10^9$-$1\times10^{11}$, $1\times10^{10}$-$1\times10^{11}$, $1\times10^{11}$-$1\times10^{12}$, $1\times10^{12}$-$1\times10^{13}$, $1\times10^{13}$ gc/mL of the gene therapy construct of the present disclosure are administered to the subject. In some embodiments, $1\times10^{13}$ gc/mL of the gene therapy construct of the present disclosure are administered to the subject.

In some embodiments, the dose administered to the patient is informed by the type of genetic mutation the patient bears. In some embodiments, patients bearing a heterozygous mutation (e.g. patients with one wild type PARK2 gene) will be administered a lower dose of the gene therapy construct (e.g. less than $1\times10^{13}$ gc/mL). In some embodiments, patient bearing a homozygous mutation (e.g. patients with no wild type PARK2 gene) will be administered a higher dose (e.g. $1\times10^{13}$ gc/mL or higher). In some embodiments, patients bearing a mutation in a non-PARK2 gene (e.g. one or more of the SNCA, PARK7, PINK1, and/or LRRK2 genes) will be administered a lower dose (e.g. less than $1\times10^{13}$ gc/mL).

The dose administered to a patient may also be informed by the age of the patient (e.g. pediatric, adolescent, adult) and severity of the disease. In some embodiments, a pediatric patient will be administered a lower dose than that administered to an adolescent or an adult. In some embodiments, an adolescent patient will be administered a lower dose than that administered to an adult. In some embodiments, patients displaying more severe symptoms of the disease will be administered a greater dose than patients with more mild symptoms, or patients in the early stage of the disease. In some embodiments, patients at risk of developing a disease (e.g. those bearing one or more PARK2 mutations) will be administered a lower dose than that administered to patients displaying symptoms.

The pharmaceutical compositions may be administered to a patient as many times as appropriate. In some embodiments, the pharmaceutical composition is administered to the patient daily, weekly, monthly, or yearly. In some embodiments, the pharmaceutical composition is administered between 1 and 50 times. In some embodiments, pharmaceutical composition is administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 times. In some embodiments, the dose of the pharmaceutical composition remains the same for one or more administrations. In some embodiments, the dose of the pharmaceutical composition remains the same for each administration. In some embodiments, the dose of the pharmaceutical composition changes for one or more administrations.

As taught herein, variant parkin polypeptides may contain activating mutations that result in increased polypeptide activity compared to wild type parkin. In these cases, lower levels of expression of the activated parkin variant may demonstrate activity at wild type levels or near wild type levels. Thus, in some embodiments, administration of lower doses of the activated parkin variant demonstrates an effective treatment while also demonstrating fewer deleterious side effects associated with AAV vector delivery (e.g. inflammation, edema, hemorrhage, etc.).

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein.

Examples of Non-Limiting Embodiments of the Disclosure

Embodiments of the present subject matter disclosed herein may be beneficial alone or in combination with one or more other embodiments. Without limiting the foregoing description, certain non-limiting embodiments of the disclosure, numbered 1 to 65, are provided below. As will be apparent to those of skill in the art upon reading this disclosure, each of the individually numbered embodiments may be used or combined with any of the preceding or following individually numbered embodiments. This is intended to provide support for all such combinations of embodiments and is not limited to combinations of embodiments explicitly provided below.

Embodiment 1. A method of treating, preventing, or ameliorating a central nervous system disorder or a symptom thereof comprising administering a construct comprising a parkin (PARK2) gene to a patient in need thereof.

Embodiment 2. The method of embodiment 1, wherein the PARK2 gene is a mutant PARK2 gene.

Embodiment 3. The method of embodiment 1 or 2, wherein the PARK2 gene is a mutant PARK2 gene that encodes for a protein that increases activity of parkin.

Embodiment 4. The method of any of embodiments 1-3, wherein the activating mutant PARK2 gene codes for a protein displaying increased auto-ubiquitination compared to the wild type PARK2 gene.

Embodiment 5. The method of any of embodiments 1-4, wherein the activating mutant PARK2 gene comprises the nucleic acid sequence of SEQ ID NO; 3, 5, or 7.

Embodiment 6. The method of any one of embodiments 1-5, wherein the construct is encased in a viral vector or portion thereof.

Embodiment 7. The method of any of embodiments 1-6, wherein the viral vector is an adeno-associated viral vector or portion thereof.

Embodiment 8. The method of any of embodiments 1-7, wherein the adeno-associated viral vector or portion thereof is AAV1, AAV2, AAV3, AAV4, AAV5, AAV6, AAV7, AAV8, AAV9, AAV10, AAV11, AAV12, or AAV13.

Embodiment 9. The method of any of embodiments 1-8, wherein the adeno-associated viral vector of portion thereof is AAV9.

Embodiment 10. The method of any one of embodiments 1-9, wherein the PARK2 gene is under control of a tissue specific promoter.

Embodiment 11. The method of any of embodiments 1-10, wherein the PARK2 gene is under control of a neuron-specific promoter.

Embodiment 12. The method of any of embodiments 1-11, wherein the PARK2 gene is under control of a ubiquitous promoter.

Embodiment 13. The method of any one of embodiments 1-12, wherein the PARK2 gene is under control of a promoter selected from the list: chicken-beta-actin (CBA), human beta actin (HuBa), cytomegalovirus (cMV), CAG, PGL, EF1-alpha, GAPDFI, SV40, FIBV, human synapsin (hSYN1), alpha-internexin (INA), nestin (NES), tyrosine hydroxylase (TH), forkhead box A2 (FOXA2), calmodulin-dependent protein kinase II (CAMKII), and neuron-specific enolase (NSE).

Embodiment 14. The method of any one of embodiments 1-13, wherein the construct comprises an enhancer.

Embodiment 15. The method of any of embodiments 1-14, wherein the enhancer is a CMV enhancer.

Embodiment 16. The method of any of embodiments 1-15, wherein the construct comprises an AAV inverted terminal repeat (ITR).

Embodiment 17. The method of any of embodiments 1-16, wherein the construct comprises two AAV inverted terminal repeats (ITRs) flanking the expression cassette.

Embodiment 18. The method of any one of embodiments 1-17, wherein the construct is administered directly into the brain.

Embodiment 19. The method of any one of embodiments 1-18, wherein the construct is administered by intrathecal administration.

Embodiment 20. The method of any one of embodiments 1-19, wherein the central nervous system disorder is Parkinson's Disease.

Embodiment 21. The method of any of embodiments 1-20, wherein the patient displays one or more symptoms of Parkinson's Disease.

Embodiment 22. The method of any of embodiments 1-20, wherein the patient is at risk of developing one or more symptoms of Parkinson's Disease.

Embodiment 23. The method of any of embodiments 1-22, wherein the one or more symptoms of Parkinson's Disease is selected from the group consisting of: motor deficits, tremors, bradykinesia (slowed movement), rigid muscles, impaired posture and balance, loss of automatic movements, speech changes, writing changes, depression, swallowing problems, decreased cardiac function, sleep disorders, dementia, cognitive problems, emotional changes (e.g. fear, anxiety, or loss of motivation), blood pressure changes, fatigue, pain, involuntary movements, shuffling gait, dizziness, amnesia, confusion, voice box spasms, distorted sense of smell, jaw stiffness or reduced facial expression, and weight loss.

Embodiment 24. The method of any of embodiments 1-23, wherein administration of the construct increases the number of dopaminergic neurons in the patient.

Embodiment 25. A recombinant gene therapy vector comprising a mutant parkin (PARK2) gene.

Embodiment 26. The vector of embodiment 25, wherein the PARK2 gene is a mutant PARK2 gene that encodes for a protein that increases activity of parkin.

Embodiment 27. The vector of any of embodiments 25-36, wherein the activating mutant PARK2 gene codes for a protein displaying increased auto-ubiquitination compared to the wild type PARK2 gene.

Embodiment 28. The vector of any of embodiments 25-27, wherein the mutant PARK2 gene codes for a polypeptide with a mutation at the amino acid position of 146, 183 and/or 463 of parkin.

Embodiment 29. The vector of any of embodiments 25-28, wherein the mutant PARK2 gene codes for a polypeptide with a mutation at the amino acid position of 146 and/or 183 of parkin.

Embodiment 30. The vector of any of embodiments 25-29, wherein the mutation of an amino acid is to a tyrosine residue.

Embodiment 31. The vector of any of embodiments 25-30, wherein the polypeptide comprises SEQ ID NO: 4, 6, or 8.

Embodiment 32. The vector of any of embodiments 25-31, wherein the polypeptide comprises SED ID NO: 4 or 6.

Embodiment 33. The vector of any of embodiments 25-32, wherein the construct is encased in a viral vector or portion thereof.

Embodiment 34. The vector of any of embodiments 25-33, wherein the viral vector is an adeno-associated viral vector or portion thereof.

Embodiment 35. The vector of any of embodiments 25-34, wherein the adeno-associated viral vector or portion thereof is AAV1, AAV2, AAV3, AAV4, AAV5, AAV6, AAV7, AAV8, AAV9, AAV10, AAV11, AAV12, or AAV13.

Embodiment 36. The vector of any of embodiments 25-35, wherein the adeno-associated viral vector of portion thereof is AAV9.

Embodiment 37. The vector of any of embodiments 25-36, wherein the PARK2 gene is under control of a tissue specific promoter.

Embodiment 38. The vector of any of embodiments 25-37, wherein the PARK2 gene is under control of a neuron-specific promoter.

Embodiment 39. The vector of any of embodiments 25-38, wherein the PARK2 gene is under control of a ubiquitous promoter.

Embodiment 40. The vector of any of embodiments 25-39, wherein the PARK2 gene is under control of a promoter selected from the list: chicken-beta-actin (CBA), human beta actin (HuBa), cytomegalovirus (cMV), CAG, PGL, EF1-alpha, GAPDFI, SV40, FIBV, human synapsin (hSYN1), alpha-internexin (INA), nestin (NES), tyrosine hydroxylase (TH), forkhead box A2 (FOXA2), calmodulin-dependent protein kinase II (CAMKII), and neuron-specific enolase (NSE).

Embodiment 41. The vector of any of embodiments 25-40, wherein the construct comprises an enhancer.

Embodiment 42. The vector of claim 41, wherein the enhancer is a CMV enhancer.

Embodiment 43. The vector of any of embodiments 25-42, wherein the construct comprises an AAV inverted terminal repeat (ITR).

Embodiment 44. The vector of any of embodiments 25-43, wherein the construct comprises two AAV inverted terminal repeats (ITRs) flanking the expression cassette.

Embodiment 45. An isolated polypeptide comprising SEQ ID NO: 4 or 6.

This disclosure is further illustrated by the following non-limiting examples.

EXAMPLES

Example 1—Design of Gene Therapy Constructs for AAV9 Delivery

The overall design of the gene therapy constructs used in the present disclosure is shown in FIG. 1 The PARK2 gene is represented as the cDNA human sequence, and several variants were tested: W183Y, F208Y, and F463Y along with a wild type PARK2. The expression of these cDNA sequences was controlled by a CBA promoter for maximum expression. The single-stranded DNA containing the PARK2 cDNA sequence is flanked by inverted terminal repeats (ITR) for packaging into an AAV9 capsid for intrathecal deliver to parenchymal tissue in the brain. The spread of the virus and the expression of the PARK2 transgene will be measured.

Figure 2:
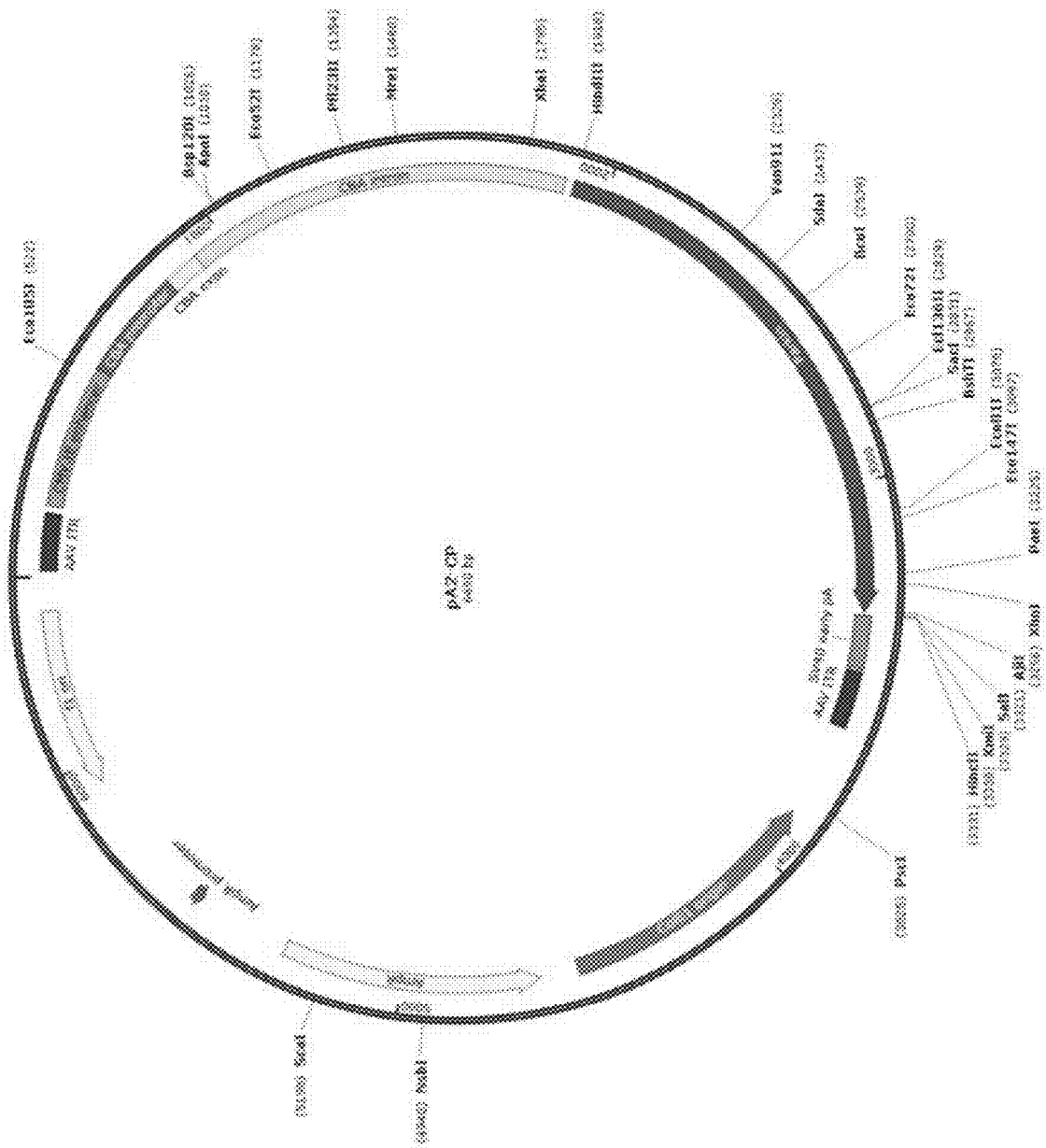
FIG. 2 shows a plasmid map of a gene therapy construct comprising a wild type Parkin cDNA sequence.
Figure 3:
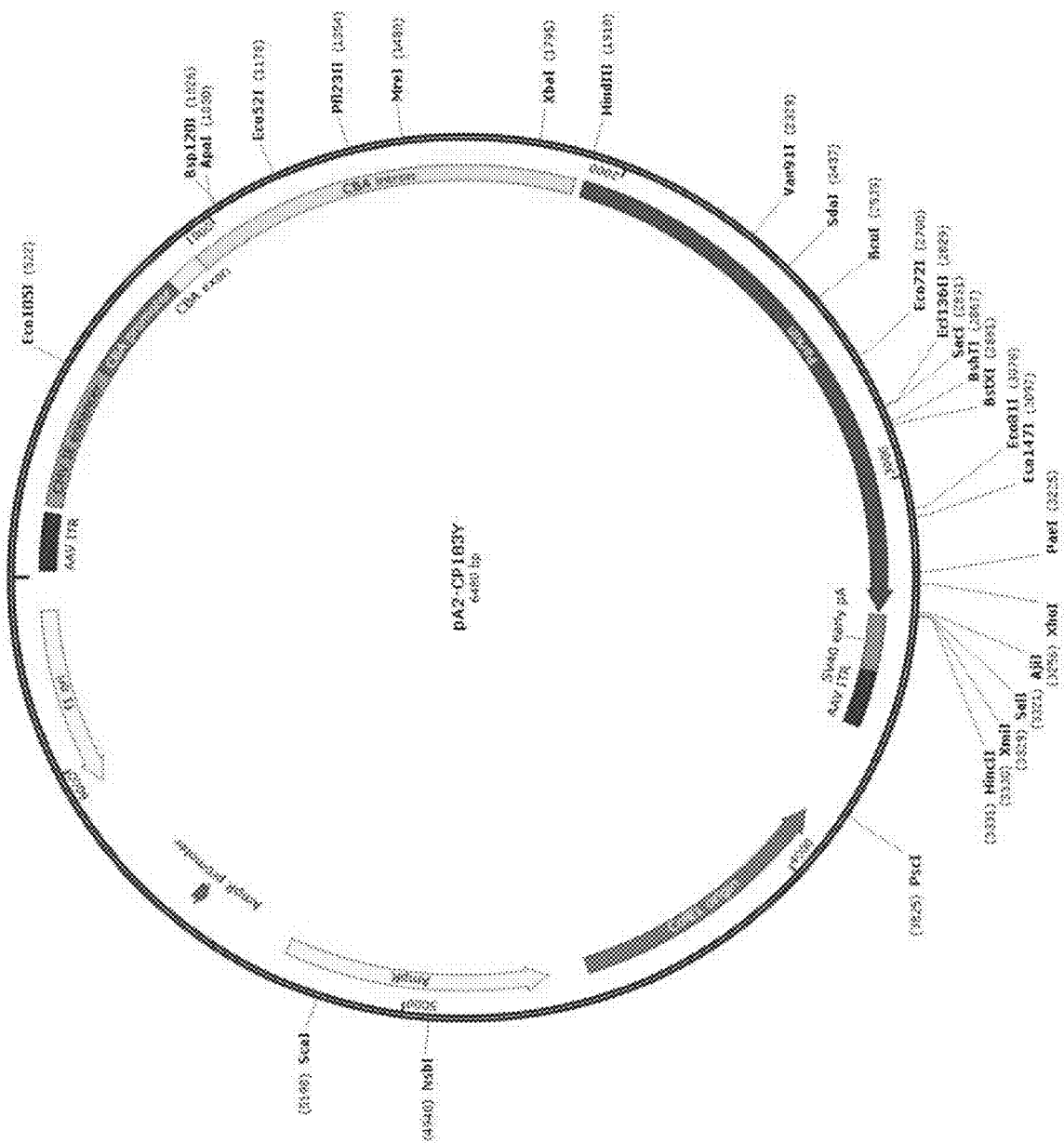
FIG. 3 shows a plasmid map of a gene therapy construct comprising a W183Y Parkin mutant cDNA sequence.
Figure 4:
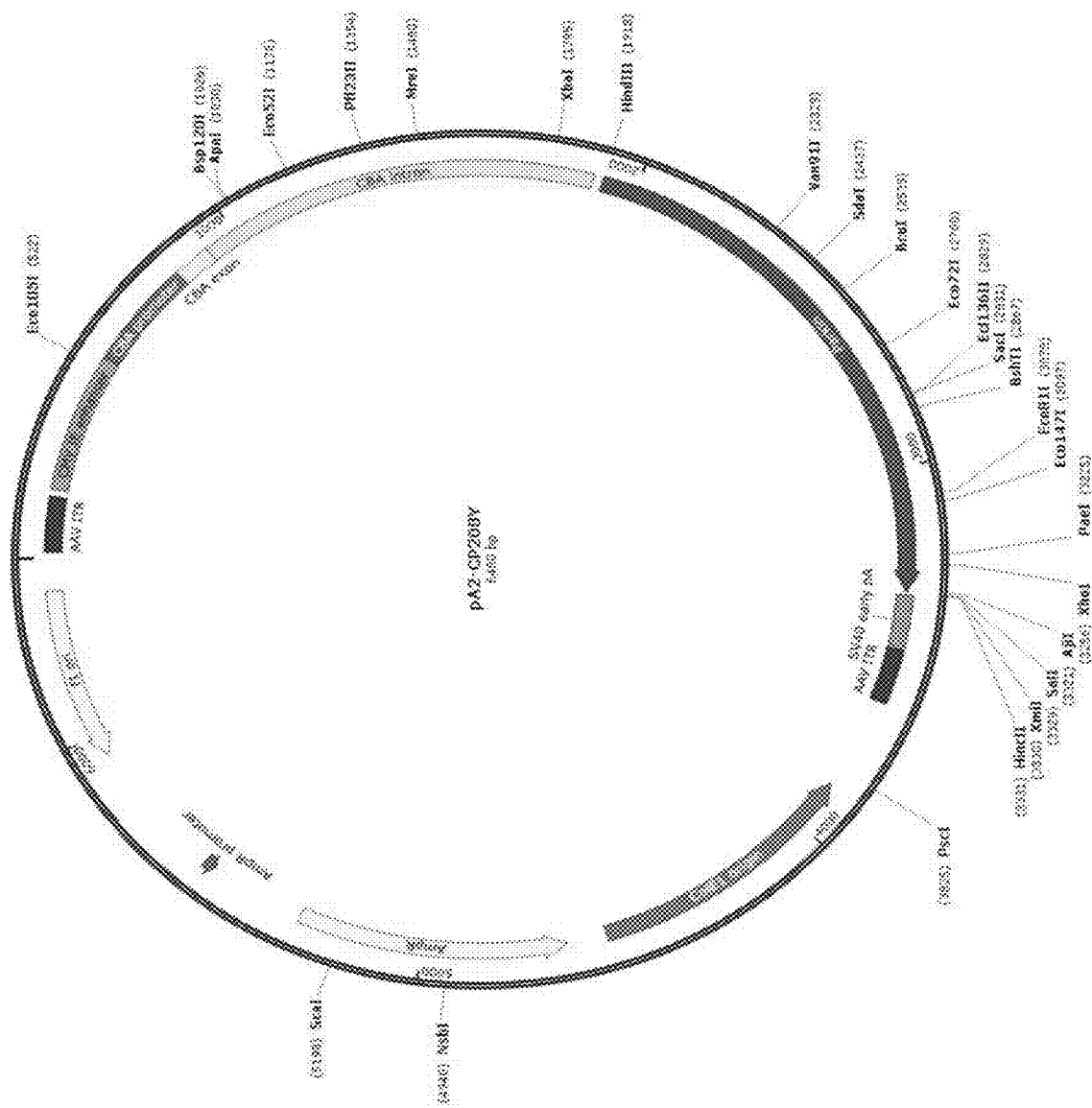
FIG. 4 shows a plasmid map of a gene therapy construct comprising a F208Y Parkin mutant cDNA sequence.
Figure 5:
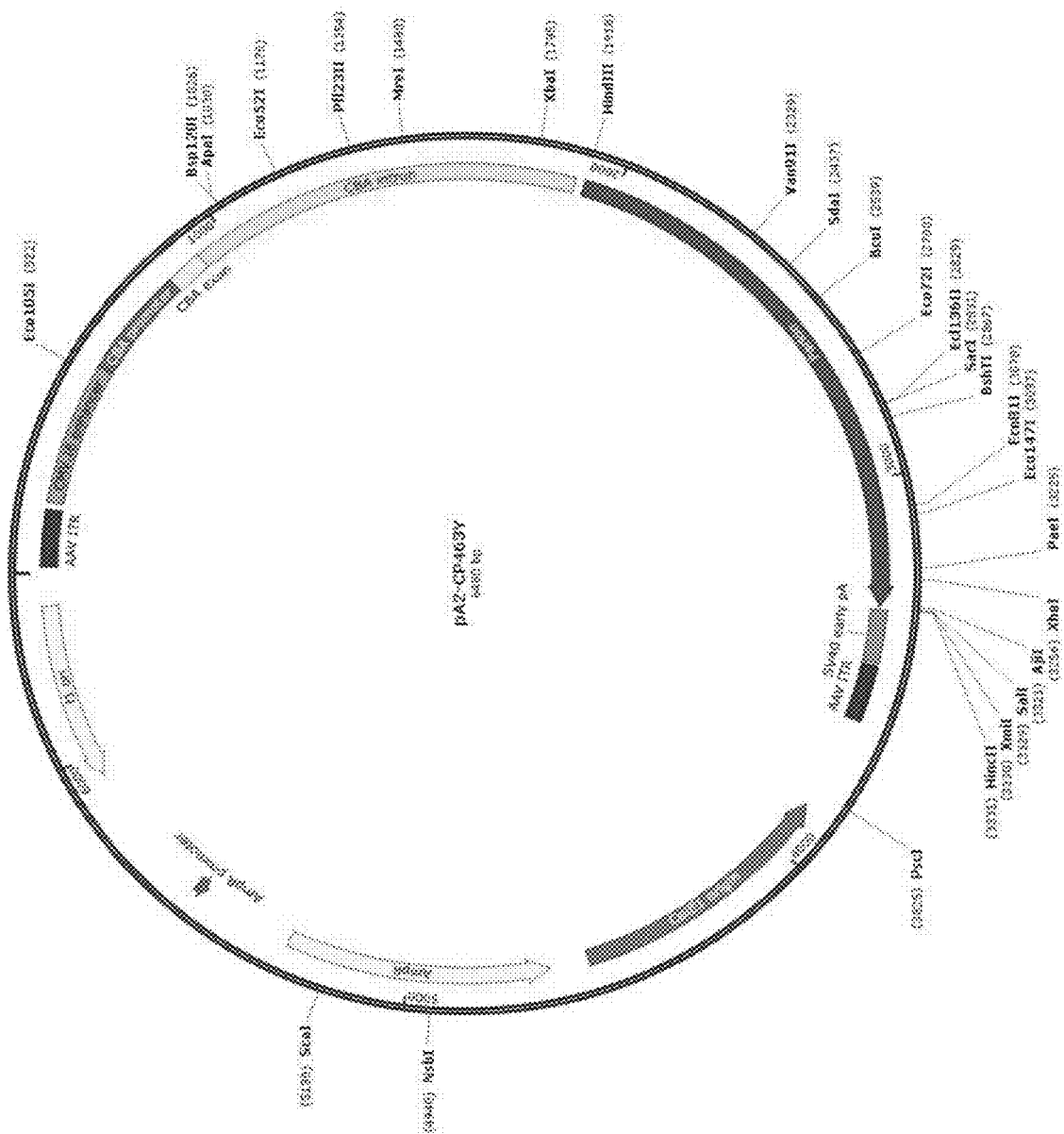
FIG. 5 shows a plasmid map of a gene therapy construct comprising a F463Y Parkin mutant cDNA sequence.

FIGS. 2-4 show the AAV9 constructs for gene therapy constructs containing the wild type parkin (PARK2), W183Y mutant, F208Y mutant, and F463Y mutants respectively.

Example 2—PARK2 Mutants Increase the Activity of Parkin

Figure 6:
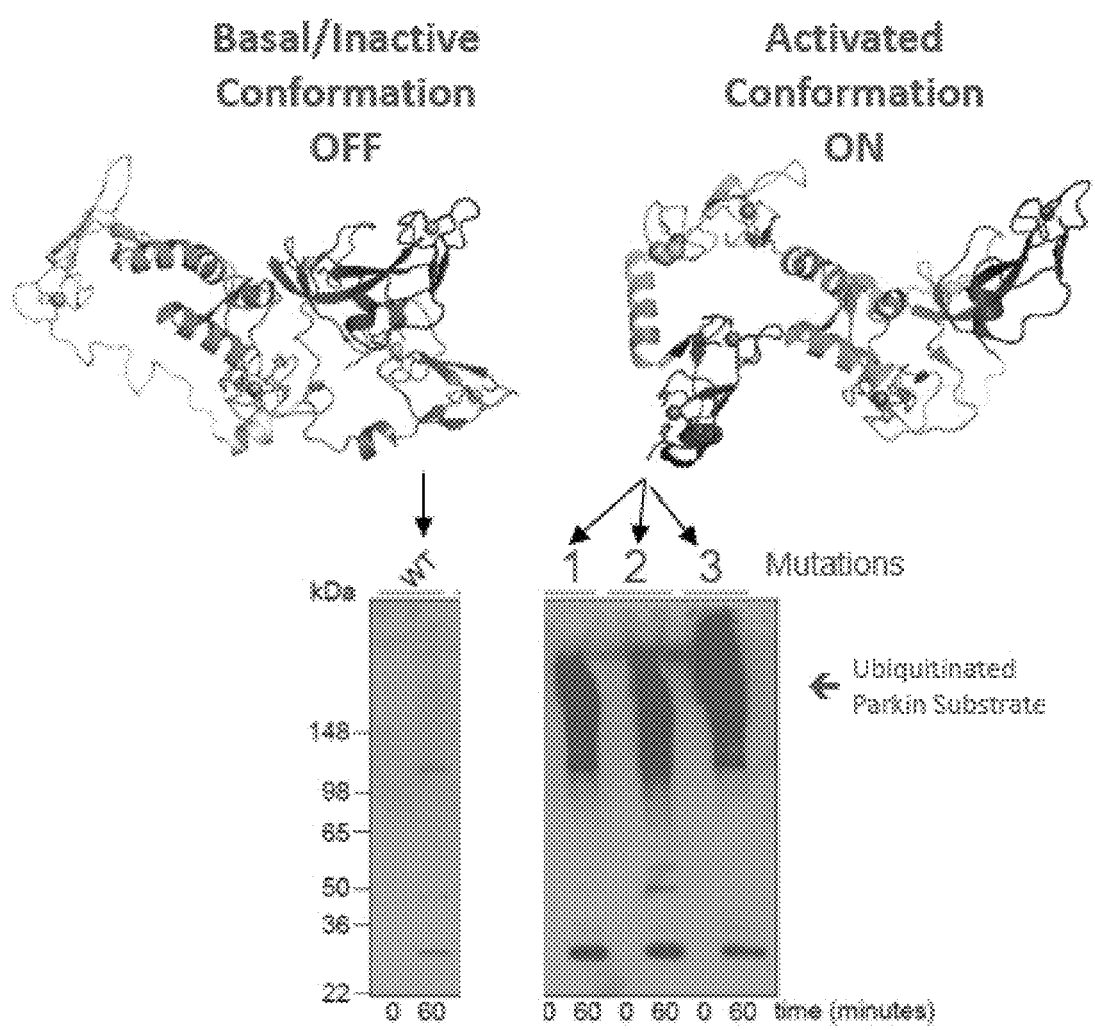
FIG. 6 shows the structure of the parkin polypeptide in both the "OFF" and "ON" state, and that the W183Y, F208Y, and F463Y parkin mutants increase activity of the parkin polypeptide.

The parkin protein is in the "OFF" state until activated with stimuli. (FIG. 6). However, the W183Y, F208Y, and F463Y mutations change this state and are activating mutations that increase activity for the "ON" state.

Figure 7A:
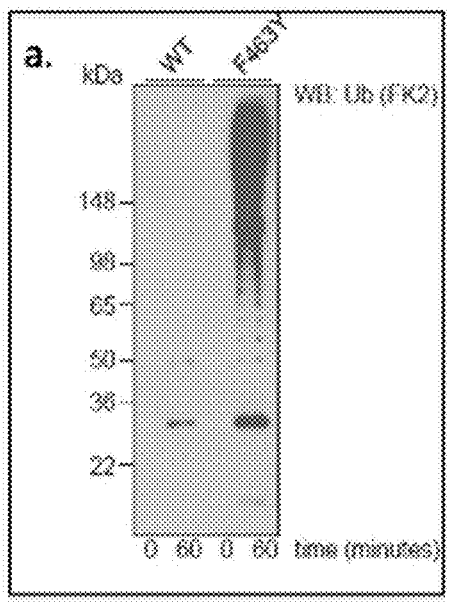
FIGS. 7A-C. Panels A & C show the purified W183Y, F208Y, and F463Y mutant polypeptides demonstrate increased auto-ubiquitination. Panel B shows that cells expressing this mutant exhibit increased functional mitophagy activity as determined by a Tom20 assay compared to wild type.
Figure 7B:
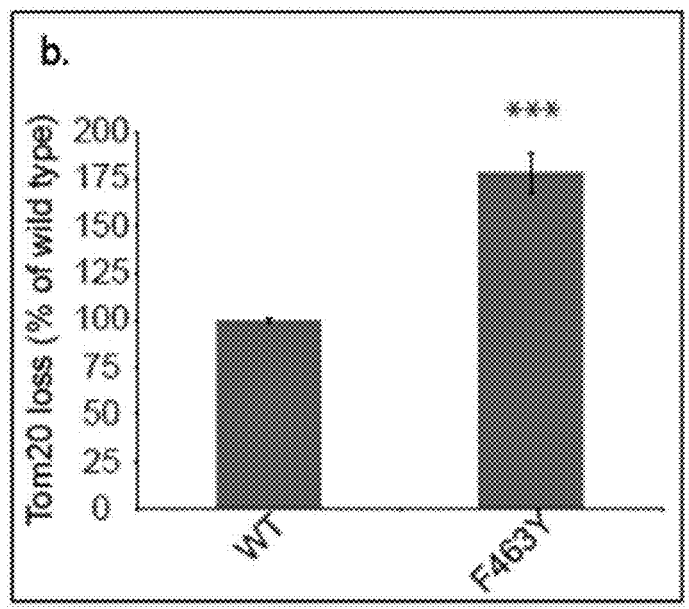
Figure 7C:
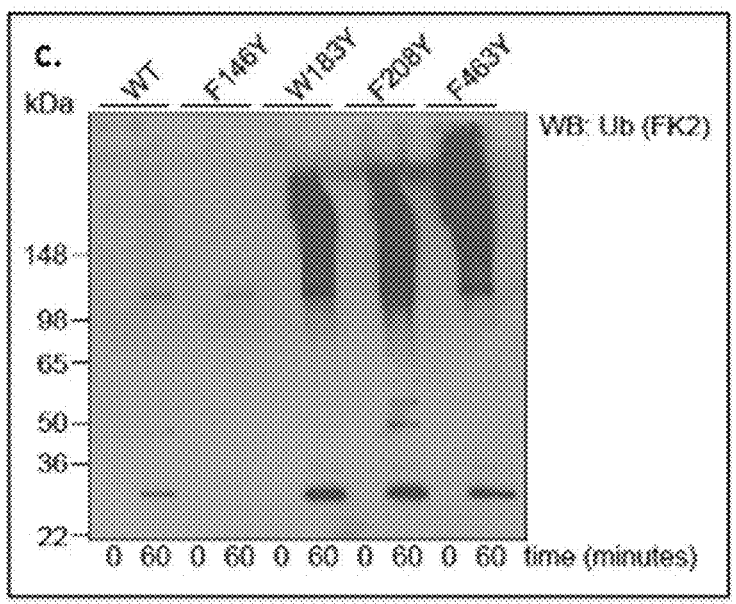
Figure 8:
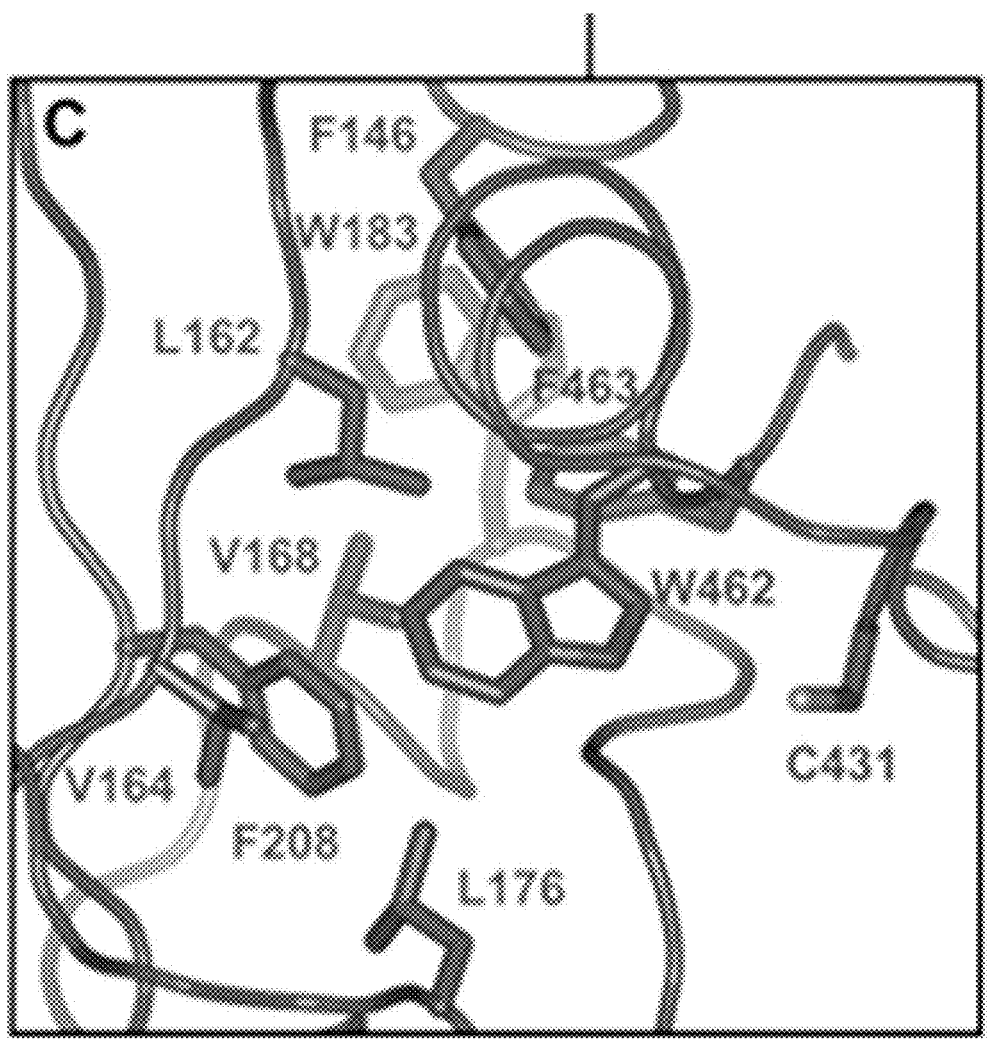
FIG. 8 shows the crystal structure of the Parkin polypeptide as a ribbon diagram demonstrating the R0 and R2 hydrophobic interface and amino acid residues described herein.

As shown in FIG. 7, the F463Y PARK2 mutant increases the activity of parkin in cells. This mutation is in the R2 residue (FIG. 7C), and contains a change from a phenylalanine (F) to tyrosine (Y) at residue 463. The crystal structure (FIG. 8) shows that the F463 residue is proximal to the active site cysteine of Parkin C431, and buried within the R0/R2 interface. Residues F146, W183, and F208 lie in the R0 region, and residues W462 and F463 lie in the R2 region.

An auto-ubiquitination assay was performed using the mutants and wild type parkin polypeptides. The principle of this assay is that the E3 Ligase Parkin catalyzes the transfer of Ubiquitin to target proteins, but also has the ability to auto-ubiquitinate. The phospho-Ubiquitin (pUb) is a purified cellular cofactor for Parkin and is added to the assay to decrease the energy barrier to activation of Parkin to auto-ubiquitinate though the E1-E2 cascade reactions. The Parkin sequences are tagged with a His marker, and the use of a Eu cryptate Ubiquitin and anti 6His-d2 that binds to the His tagged Parkin will give a signal when the Eu cryptate-Ubiquitin is auto-ubiquitinated onto the Parkin which can be monitored by TR-FRET. Mutations that increase parkin activation can be identified by an increase of the 0% activation (e.g. pUb) TR-FRET signal.

Assay Conditions:
  Enzyme Reaction (15 min pre-incubation with Parkin, pUb and activator only)
  Parkin: 196 nM
  pUb: 196 nM
  DMSO: 1% DMSO
  E1: 5 nM
  E2: 50 nM
  Ubiquitin Eu: 8.8 nM
  Reaction time: 120 minutes
  Temperature: 22° C.
  Total volume: 10 µl reaction
  Reactions may be terminated by the addition of SDS-loading buffer. Western Blot detection was performed with Anti-ubiquitin Ab (FK2) with Ab used at 1:1000 dilution.
  Reaction also be detected by taking 10 µl of Enzyme Reaction above and add 10 µl detection Reagent Z under the following conditions:
    Reaction time: 60 minutes
    Temperature: 22° C.
    Total volume: 20 µl
    Data Analysis: The Data was read in CSV files. There are two tables in those CSV files, which are the values of 655 nm (channel 1) and 615 nm (channel 2) wavelengths respectively. The data was converted to an HTRF Ratio=(Channel 1/Channel 2)*10,000

The average of all the 0 uM controls (DMSO only)=BKGD (Background–0% activation). Subtract BKGD from each HTRF Ratio value=HTRF−BKGD. The average of all the 100 uM control activator in DMSO controls=Max (100% activation). The following equation is then used to calculate % Activation for each well/candidate as follows: % Activation=(HTRF−BKGD/Max)*100.

The % Activation of compound titration is then used to find activation EC50 or highest % activation if less than 75% activation is seen for the candidate compound.

XLFIT5 model 205 was applied for the data analysis. EC50 fit model (4 Parameter Logistic Model/Sigmoidal dose-Response Model); fit=(A+((B−A)/(1+((C/x)^D)))); res=(y-fit). The parameters are:
  A: Bottom
  B: Top
  C: Relative EC50
  D: Hill Slope
Constrains set to Bottom=0 and Top=100.

FIGS. 7A & C show that the W183Y, F208Y, and F463Y mutant purified proteins demonstrate increased autoubiquitination.

Tomm20 Assay

The Tomm20 loss assay screens for the ability for cells to augment mitophagy, the process of removing damaged mitochondria which is compromised in Parkinson's Disease patients and in animal and cellular model systems for PD. Here, HeLa cells were transfected with Parkin cDNA to assess Parkin-dependent induction of mitophagy. Cells were transfected with a protein comprising one of: wild type Parkin; the W183Y parkin mutant; the F208Y parkin mutant; or the F463Y parkin mutant. 4000 cells of each transformant were seeded in each well of a 96 well plate (Parkin Elmer ViewPlate-96 F TC, cat. N. 6005182) and left to grow for 24 hours. HeLa cells were chosen for these experiments as HeLa cells do not express any endogenous Parkin protein due to genetic deletion.

Subsequently cells were incubated with vehicle (DMSO) or 6 μM CCCP for each condition run in replicate of five. After 20 hours cells were processed for immunofluorescence.

Immunofluorescence: Samples were fixed in 4% PFA for 25 minutes RT and permeabilized with PBS 0.1% Triton-X100 for 3 minutes on ice, blocked with PBS 3% BSA, 0.3% Triton-X100 for 2 hours RT, followed by overnight incubation with primary antibody at 4° C. (0.5 μg/ml rabbit Tomm20 antibody FL-145; Santa Cruz Biotechnology) diluted in PBS 0.1% BSA, 0.3% Triton-X100. The secondary goat anti-rabbit antibody conjugated with DyLight 649 (Jackson ImmunoResearch) was applied for 1 hour at room temperature at a concentration of 2.8 μg/ml in conjunction with 1 μg/ml Hoechst33342.

Cells were imaged using an Olympus ScanR automated microscope equipped with motorized stage and 20×APO planar objective. 18 images were acquired for each well using the following combination of excitation/emission filters: Hoechst33342 was excited through a 350/50 nm band pass filter and fluorescence intensity was collected through a 460/30 band pass filter. DyLight 649 was excited through a 640/30 nm band pass filter and fluorescence intensity was collected through 700/75 band pass filter. Images were processed and analyzed as described in the Image Analysis section.

Image analysis: Images were processed and analyzed using Columbus HCS Analysis software (Version 2.5.0., PerkinElmer) as follows:

Tomm20 fluorescence intensity was corrected using the parabola algorithm. Hoechst 33342 fluorescence was used to identify and count cells. Cells were segmented according to Tomm20 fluorescence intensity. Spot detection was optimized to recognize number and total cellular area of Tomm20 stained clusters (mitochondria).

Tomm20 staining intensity, spot numbers and spot area were used to train a linear classifier algorithm that discriminated between Tomm20 positive (high intensity, spot numbers and spot area) and Tomm20 negative cells (low intensity, spot numbers and spot area).

Bar graphs were generated reporting the number of Tomm20 negative cells expressed as percentage of total cells imaged for each well. Results were shown as mean±SD of a representative experiment performed in triplicate). Results were shown as mean±SD of a representative experiment performed in triplicate. +++ indicates >70% effect at 10 μM; ++ indicates 69%-31% effect at 10 μM; + indicates <30% effect at 10 μM; NA=not available.

FIG. 7B shows that the expression of the F463Y parkin mutant exhibits increased functional mitophagy activity compared to wild type parkin as screened using the Tomm20 loss assay.

Figure 9:
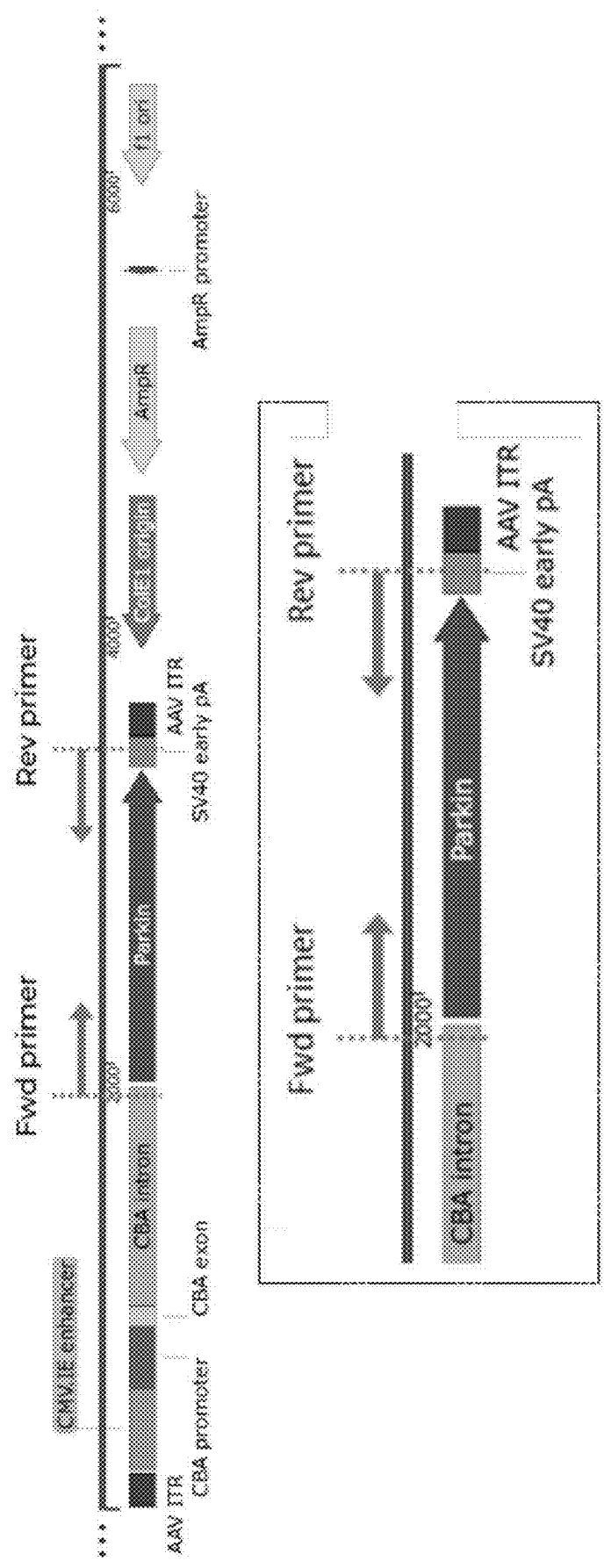
FIG. 9 shows an exemplary vector construct encoding a Parkin gene.

Example 3—Production of AAV5 Constructs for Gene Therapy Delivery of Wild Type Parkin and Mutants FIG. 9 shows plasmids used encode the recombinant AAV genome (AAV2 ITRs, chicken beta-actin promoter including a CMV enhancer element (CBA), transcript variant 1 of the human wild type Parkin gene or activating variants of the Parkin gene with single amino acid mutations at position W183Y, F208Y and F463Y, and the early polyA from SV40), essential adenoviral helper genes, AAV2 Rep and AAV5 Cap genes (Grimm et al 1998). The expression of the cDNA was controlled by a CBA promoter for maximum expression. The insertion of the Parkin gene was verified by amplifying the Parkin gene using primers outside of the Parkin sequence.

Figure 10B:
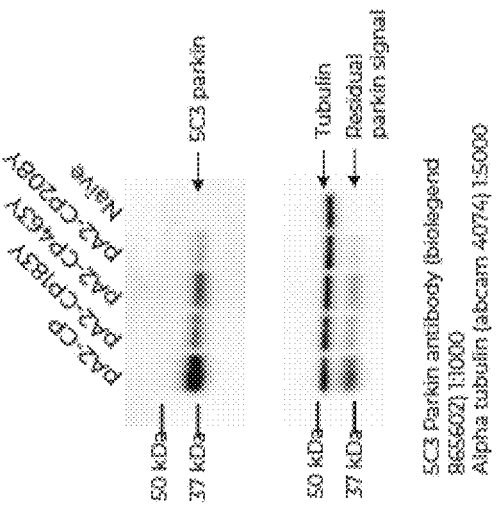
FIG. 10A-B shows expression of wild type Parkin in Hela and Hela S3 cells.
Figure 10A:
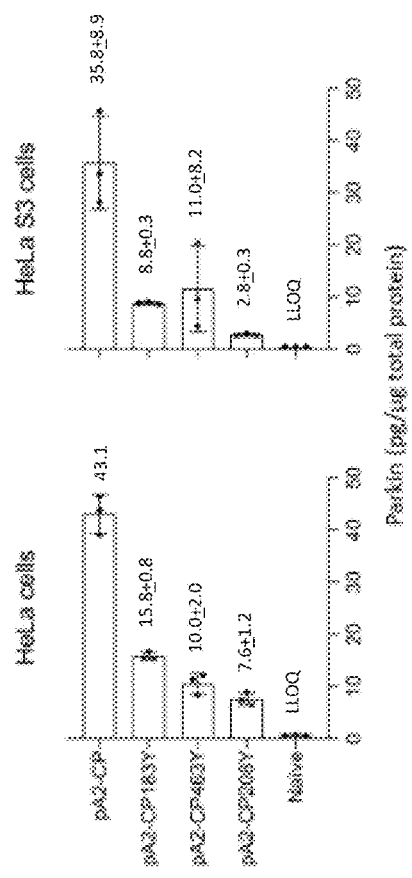

To detect expression levels, each of the vectors was transfected into HeLa and HeLa S3 cells. (FIG. 10)

HeLa S3 cells were grown in ten 175 cm$^2$ flasks and were co-transfected at a confluency of 70-80% using the calcium-phosphate precipitation method. Three days after transfection, cells were harvested using DPBS with 5 mM EDTA, resuspended in 30 ml buffer (50 mM Tris, 150 mM NaCl, pH 8.5) after centrifugation (1000 RCF for 5 minutes) and lysed by freezing in a bath of dry ice and ethanol. The lysate was thawed in a 37° C. water bath and treated with 11 units/ml Benzonase for 30 minutes. The preparation was clarified by centrifugation (3220 RCF for 25 minutes) and AAV purified using a discontinuous Iodixanol gradient, followed by anion exchange chromatography (Zolotukhin et al 1999) using a Mustang Q adsorption device (Pall). Buffer exchange to DPBS and concentration was done using a 100 kDa molecular weight cut-off centrifugation filter unit. Titers of the stock solution were determined by quantitative PCR using primers and hydrolysis probe targeting the ITR sequence (Aurnhammer et al 2012). Before being used in an experiment, vectors were diluted in DPBS and re-titered. Glass capillaries used for animal injections were pre-coated with the same AAV vector, before injection.

Figure 11:
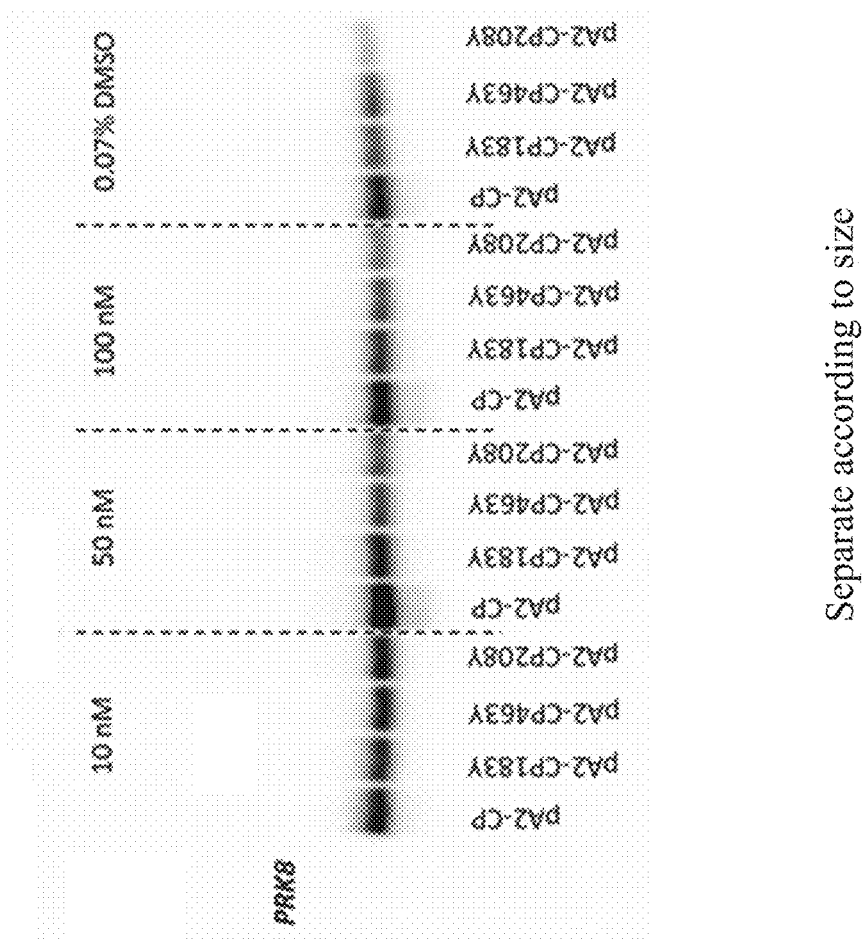
FIG. 11 shows treatment with epoximicin restores the variant parkin polypeptides to wild type levels.

To confirm activity of the variant parkin polypeptides, HeLa S3 cells were transfected by seeding 0.8 million cells/mL in a 6 well plate, and after 24 hours, transfecting the cells with 2500 ng of DNA per well in medium containing 10% FBS. Cells were transfected with: pA2-CP (wt parkin); pA2-CP183Y; pA2-CP208Y; pA2-CP463Y; a naïve control, or a pA2-CG (GFP control for visualization). 6 hours after transfection, the medium was changed to 4% FBS, and the cells were incubated for 50 hours. On day 4, the cells were treated with 10, 50, or 100 nM the proteasome inhibitor epoxomicin or vehicle (0.07% DMSO). The cells were incubated for 16 hours, and on day 5 the cells were harvested and processed. All floating cells were collected. The protein (10 μg protein/well) was visualized using anti-PRK8 and anti-FX2 antibodies. The parkin variants are synthesized at the same rate, but because they are more active, they are turned-over at a higher rate, and can appear less abundant. However, after epoxomicin treatment, the protein levels are returned to the same level as wild type parkin. (FIG. 11).

Example 4—Transduction of Rat Neuronal Cells with Construct Containing Wild Type Parkin Gene Stereotaxic Surgery:

Adult, female Sprague-Dawley rats were anesthetized by i.p. injection of 6 mL/kg of a 20:1 mixture of Fentanyl and Dormitor (Apoteksbolaget, Sweden). After placing the animal into a stereotaxic frame (Stoelting, Wood Dale, USA), rats were unilaterally injected with 2 µl of the rAAV5-CBA-Parkin (WT) vector in the substantia nigra according to the following coordinates: 5.2 mm posterior from bregma, 2.0 mm lateral from bregma, 7.2 mm ventral to dura while the tooth bar was adjusted to obtain a flat skull position. The injection rate of the viral vector was 0.1 µl every 15 sec and the capillary was held in place for 5 min after the injection before the needle was slowly retracted. Rats were killed 4 weeks after vector injections by an overdose of sodium pentobarbital and perfused via the ascending aorta first with 50 mL of 0.9% NaCl followed by 250 mL of ice-cold 4% paraformaldehyde for 5 min. Brains were removed and post-fixed in 4% PFA for 24 h and then transferred into 25% sucrose for cryoprotection. The brains were then cut into 35 µm thick coronal sections in six series and processed for histology.

Parkin and TH immunohistochemistry was performed on free-floating sections. Brain sections were washed with tris-buffered saline before the endogenous peroxidase activity was blocked by quenching with 3% H2O2 and 10% Methanol in TBS buffer for 30 min. After three washes with TBS buffer, sections were incubated in 0.05% Triton X-100 in TBS buffer (TBS-T) containing 5% of normal serum matching the species used to raise the secondary antibody for that protocol for 1 hour after which the anti-Parkin antibody [PRK8](ab77924, 1:1000, Abcam), purified anti-Parkin antibody (5C3, 1:1000, Biolegend) or TH (Pel freeze, 1:5000) was incubated with the sections for 24 hours overnight on an orbital shaker. The next day sections were rinsed with TBS-T and incubated with the corresponding biotinylated secondary antibodies (1:200, Vector Laboratories Inc, USA) in 1% BSA in TBS-T for 1 h. Sections were again washed with TBS-T and incubated with an avidin-biotin-peroxidase complex solution (Vectastain ABC kit, Vector Laboratories Inc, USA) for 1 h. Immunoreactivity was revealed with 3,3'-diaminobenzidine (DAB Safe, Saveen Werner, Sweden) and 0.01% $H_2O_2$. Sections were mounted on chromatin-gelatin coated glass slides, dehydrated in increasing alcohol solutions, cleared in xylene and coverslipped with DPX (06522, Sigma-Aldrich, Sweden).

Cresyl Violet Staining:

One series of sections was processed for cresyl violet staining. Sections were mounted on chromatin-gelatin coated glass slides and dried overnight, hydrated in decreasing alcohol solutions and stained for 30 sec in pre-filtered 0.5% cresyl violet (Sigma-Aldrich, Sweden) containing 0.1% acidic acid. After a wash in $H_2O$, sections were dehydrated in increasing alcohol solutions, cleared in xylene and coverslipped using DPX.

Discussion

Figure 12:
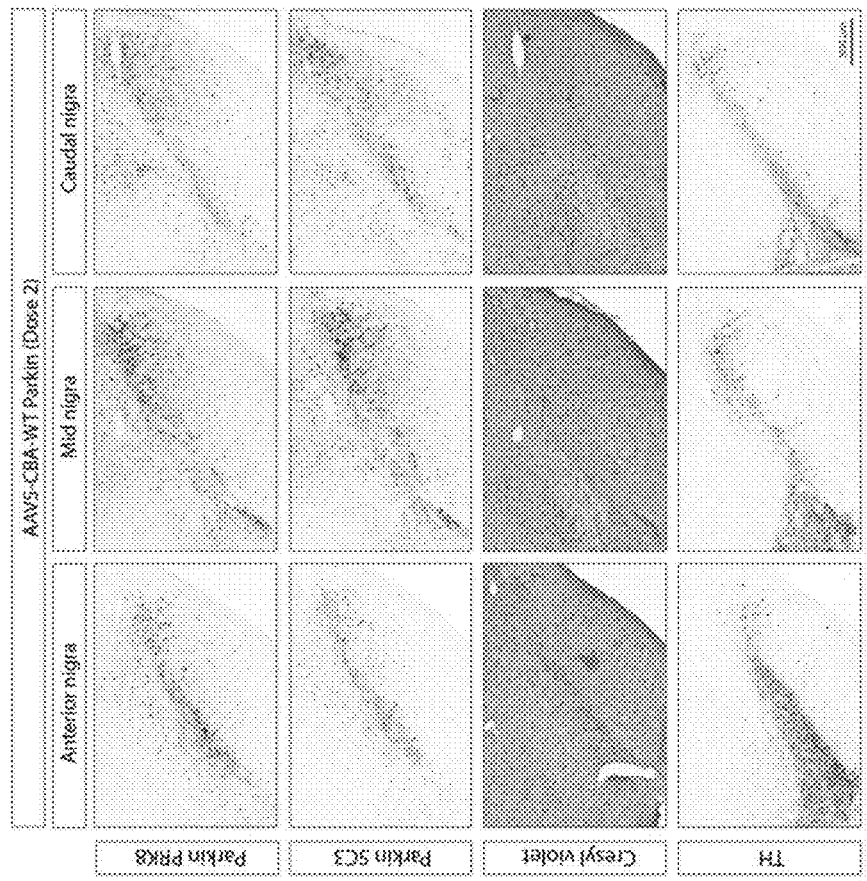
FIG. 12 shows the expression of wild type Parkin in rat neuronal cells.

Three different doses of the WT Parkin vector were tested in this experiment. Dose 1: $1.1 \times 10^{13}$ gc/mL; Dose 2: $5.7 \times 10^{13}$ gc/mL; and Dose 3: $2.0 \times 10^{14}$ gc/mL. Histology was performed 2.5 weeks after administration. FIG. 12 shows staining of the anterior nigra, mid nigra, and caudal nigra using Parkin PRK8 (1:2000 dilution), Parkin 5C3 (1:1000 dilution), Cresyl violet staining, and TH (Pelfreeze) (1:5000 dilution).

Dose 2 was selected as the optimal dose, based on no overt toxicity and good biodistribution and targeting of the substantia nigra.

This experiment confirmed that the AAV5 capsid injected into the ventral midbrain results in a predominantly neuronal transduction and high efficiency transduction of dopaminergic neurons in the rat. Dose 2 was selected to conduct in vivo experiments in Parkin knock-out rats.

Example 5—Transduction of Rat Neuronal Cells with Parkin Gene Variants

Figure 13A:
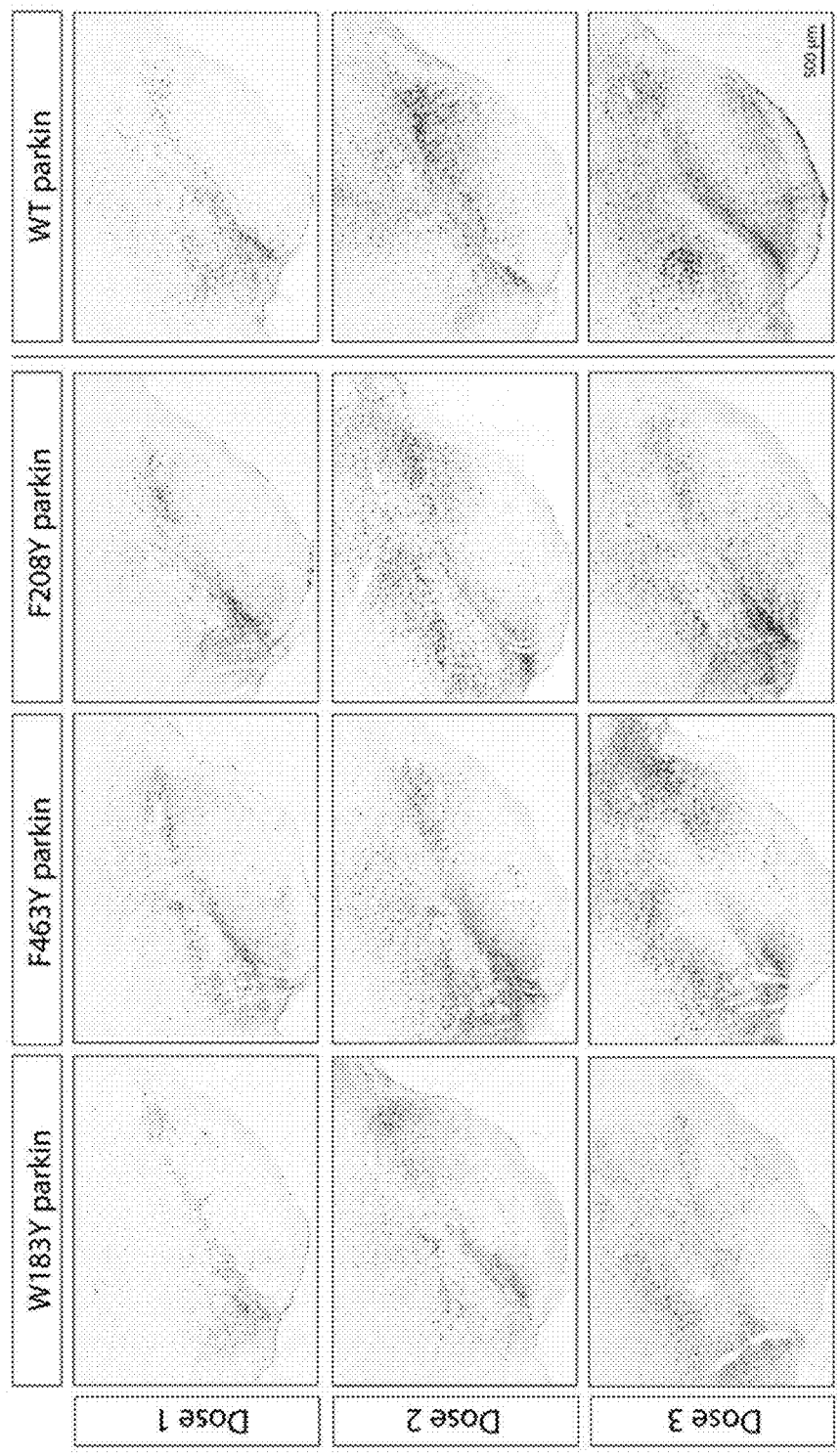
FIG. 13A-C shows expression of Parkin variants in the rat neuronal cells. Panel A shows the expression of Parkin 5C3 across the W183Y, F463Y, and F208Y mutants administered at Dose 1, Dose 2, and Dose 3. Panel B shows the histology of Dose 2 (5.9-7.2×1013 gc/mL) for the variants. Panel C shows a comparison between expression of Parkin 5C3 and Prk8 across the mutants.
Figure 13B:
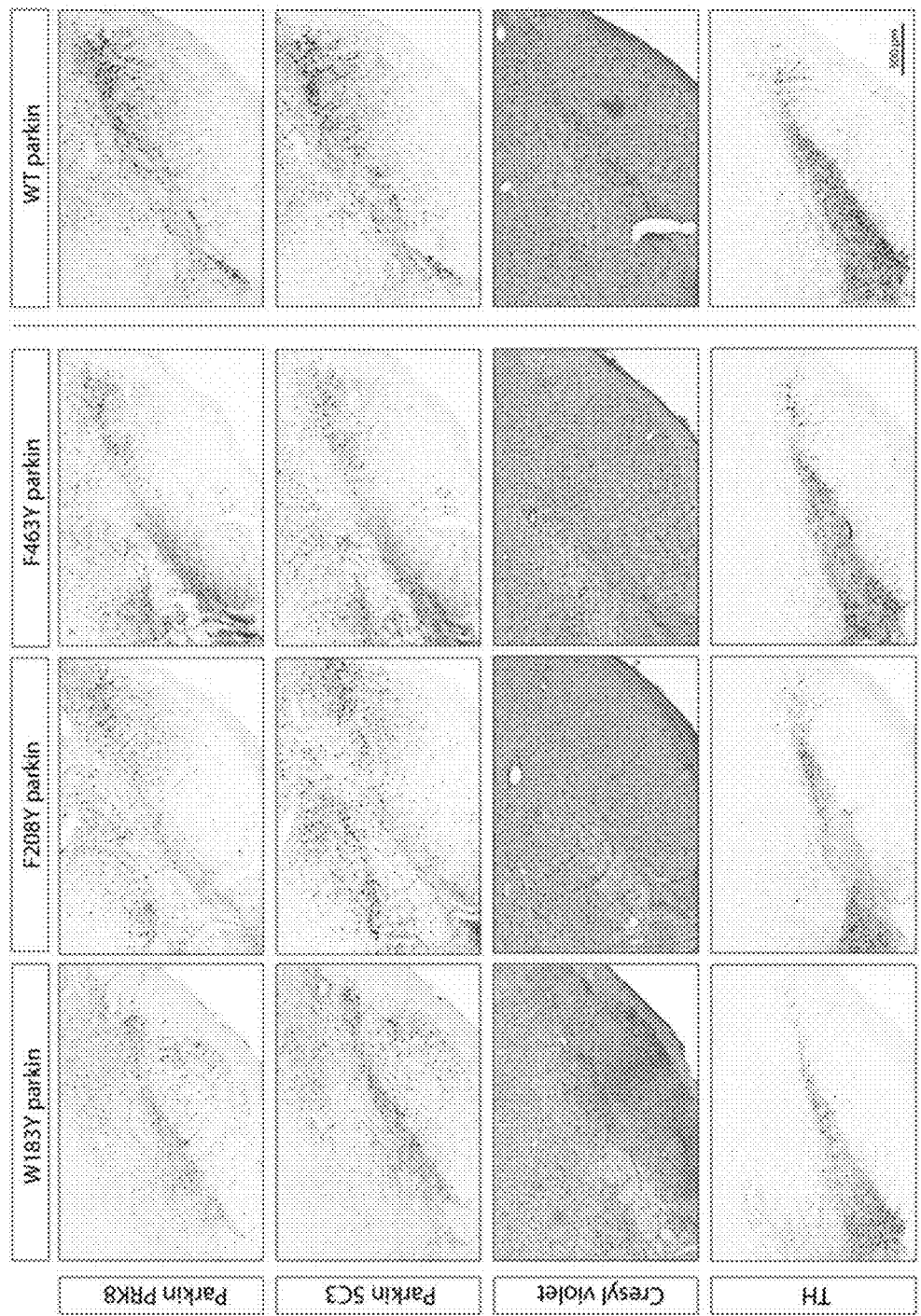
Figure 13C:
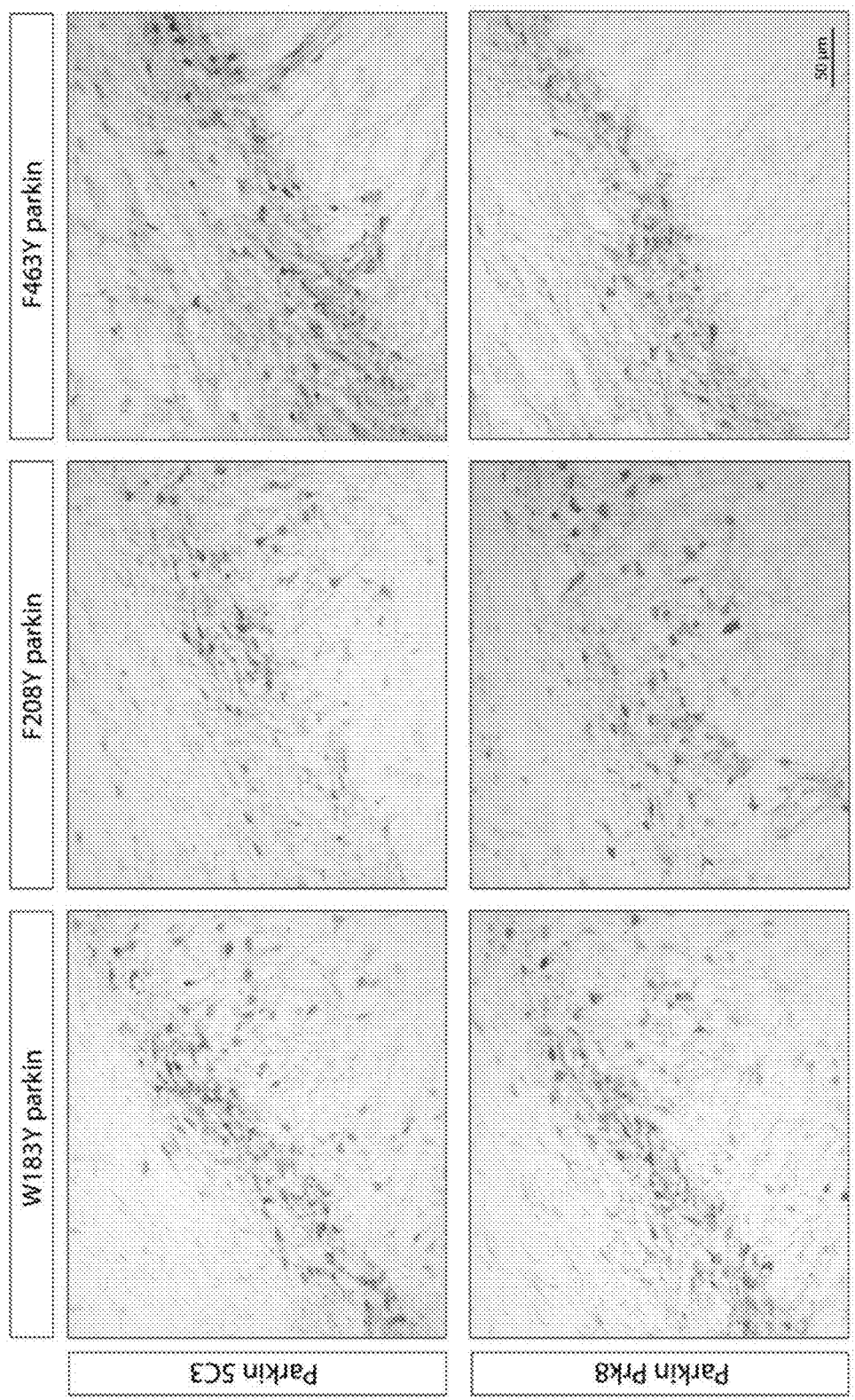

The W183Y, F208Y, and F463Y Parkin variant vectors were prepared as described in Example 3. Transduction of rat neuronal cells was carried out as in Example 4. Three different concentrations of each variant was administered—Dose 1: $1.4$-$1.5 \times 10^{13}$ gc/mL; Dose 2: $6.4$-$7.2 \times 10^{13}$ gc/mL; and Dose 3: $3.19$-$2.1 \times 10^{14}$ gc/mL. The vectors were administered into female SD rats (3/group; each weighing ~200-250 g) by injecting into the unilateral SN: AP (bregma): −5.2 mm; ML (bregma): −2.0 mm; and DV (dura): −7.2 mm. Three weeks after administration, histological analysis was performed as described in Example 4 using Parkin PRK8 (1:2000 dilution), Parkin 5C3 (1:1000 dilution), Cresyl violet staining, and TH (Pelfreeze) (1:5000 dilution). FIGS. 13A-C.

Discussion

Figure 14:
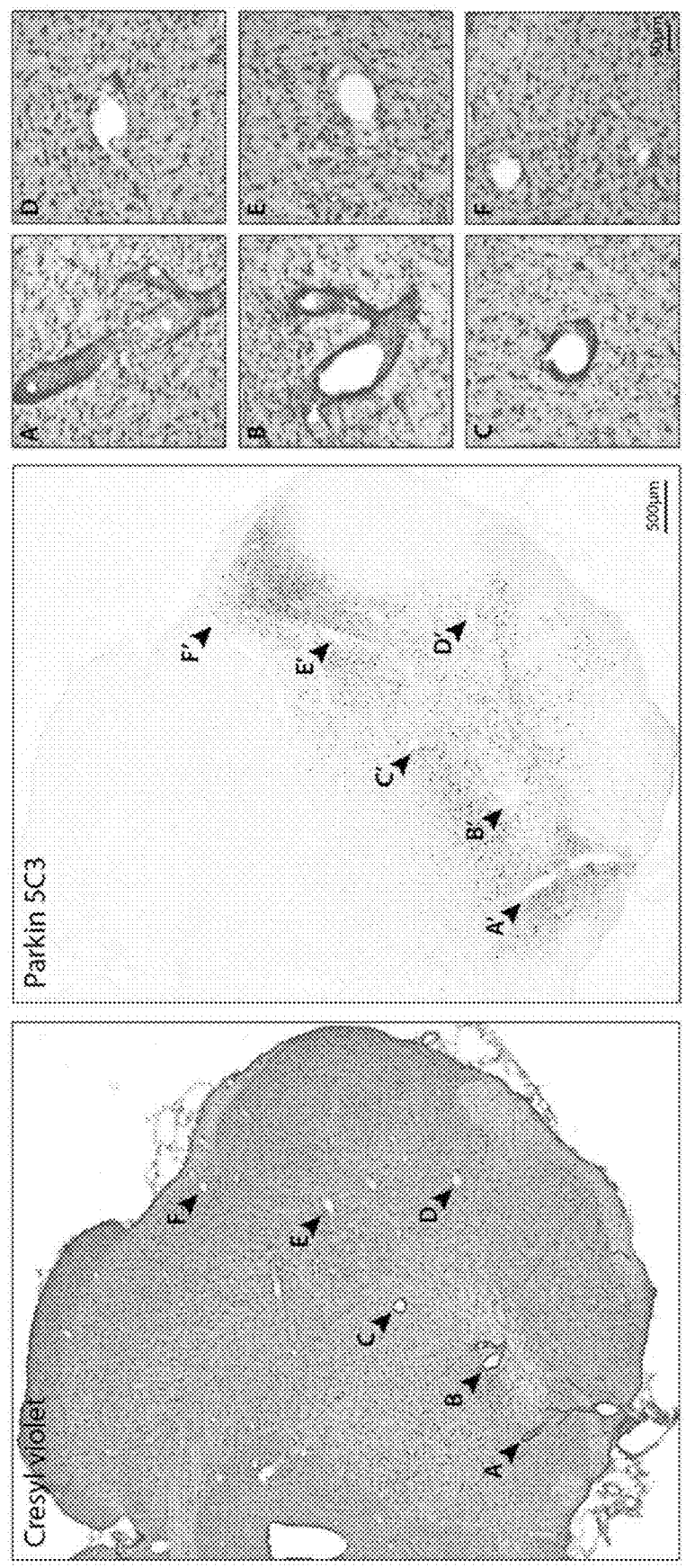
FIG. 14 shows the presence of perivascular cuffing with Dose 3 of the Parkin W183Y vector.

Some signs of tissue damage was observed for all mutants with different frequency and severity. FIG. 14 shows the presence of perivascular cuffing with Dose 3 of the Parkin W183Y vector.

As shown in Table 1 and Table 2, dose 2 appears to generate an immunological response and in some cases loss of TH neurons. This immunological response is not observed until administration of the highest dose of the wild type parkin, yet can be seen in lower doses of the variant parkins. Knowing the role of parkin in the immune system, the increased immunological response after administration of a variant parkin suggests that the variant parkin polypeptides are more active than the wild type polypeptide.

TABLE 1

Severity of perivascular cuffing visible with CV stain

| Dose | Case No. | W183Y | F208Y | F463Y | WT Parkin |
|------|----------|-------|-------|-------|-----------|
| Dose 1 | Case #1 | − | − | − | − |
|  | Case #2 | − | − | − | − |
|  | Case #3 | − | − | − | − |
| Dose 2 | Case #1 | − | − | − | − |
|  | Case #2 | ++ | − | +++ | − |
|  | Case #3 | − | ++ | − | − |
| Dose 3 | Case #1 | +++ | − | − | + |
|  | Case #2 | +++ | − | ++ | + |
|  | Case #3 | +++ | − | ++ | + |

Scale refers to perivascular cuffing/reaction: − not detected; + little; +++ severe

TABLE 2

Reduction/loss of TH immunoreactivity

| Dose | Case No. | W183Y | F208Y | F463Y | WT Parkin |
|------|----------|-------|-------|-------|-----------|
| Dose 1 | Case #1 | − | ++ | + | +/++ |
|  | Case #2 | ++ | + | + | + |
|  | Case #3 | ++ | + | ++ | − |
| Dose 2 | Case #1 | + | + | ++ | − |
|  | Case #2 | ++ | − | ++ | − |
|  | Case #3 | − | +++ | ++ | − |

TABLE 2-continued

Reduction/loss of TH immunoreactivity

| Dose | Case No. | W183Y | F208Y | F463Y | WT Parkin |
|---|---|---|---|---|---|
| Dose 3 | Case #1 | +++ | +++ | +++ | – |
|  | Case #2 | +++ | ++ | +++ | ++ |
|  | Case #3 | +++ | ++ | ++ | – |

Scale refers to the extent of TH loss: – no or limited seen only at the site of injection; + mild (visible on 2 levels); ++ moderate (visible on 3 or 4 levels); +++ severe (detected on 5 or more levels)

Example 6—Intra-Nigral Injection of Parkin Constructs in Nonhuman Primates

Four female non-human primates were included in this study. On the day of surgery, a baseline MRI scan was performed to avoid repositioning the animal. The MRI-corrected targets are shown in Table 3.

TABLE 3

| Animal | MRI-corrected targets from AC | | |
|---|---|---|---|
| ID | Antero-posterior | Lateral | Ventral |
| BO953 | –8 mm | 3.5 mm | –28.5 mm |
| BL926 | –10 mm | 3.5 mm | –27 mm |
| BV156 | –7 mm | 3.3 mm | –29 mm |
| BO803 | –8 mm | 3 mm | –27 mm |

Animal BO953

The viral vector was produced at a titer of $7 \times 10^{13}$ gc/mL, and injected at a rate of 1 µl/min into the unilateral left SNpc. A sample of the virus was used to coat the needed and syringe before loading the volume to be injected, and the remaining virus sample was kept at 4° C.

On the day of surgery (baseline), 500 µl aliquots of blood (dry tubes, serum) and 250 µl aliquots of CSF were collected as listed in Table 4. All samples were centrifuged and kept at –80° C.

TABLE 4

| Animal ID | CSF aliquots | Serum aliquots |
|---|---|---|
| BO935 | 3 | 8 |
| BL926 | 3 | 7 |
| BV156 | 3 | 8 |
| BO803 | 3 | 7 |

After surgery, the animals were observed daily for 2 weeks and weekly until euthanasia. All displayed good general appearance throughout the observation period. MRI images taken 20 days and 25 days after injection showed that the anteroposterior and lateral SN were targeted correctly in the animals. Further, there was no adverse events, such as obvious edema, hemorrhage, or inflammation, observed three of the animals (B0935, BL926, and BV156). At 25-days post injection, animal BO803 showed that, while the anteroposterior was correctly targeted, there was slight deviation targeting the lateral SN (deviation after crossing ventricle). Further, while there was no obvious edema or inflammation, hemorrhage was observed. This bleeding could have affected cell transduction by the virus.

At the end-point (euthanization) 1 blood and 1 CSF aliquots were collected. Animals were euthanized by trans-cardial perfusion with NaCl, extracting the brain and rinsing in ice-cold NaCl. The brain was placed in ice-cold matrix (on ice) and sliced into 4 slabs. The central slab (striatum) was sliced again, and punches were taken from the caudate and putamen bilaterally (and the rest of the sections were post-fixed). The peripheral organs (lung, heart, spleen, liver, kidney, and ovaries) were collected for biodistribution and preliminary toxicology studies. Post-mortem analysis of neutralizing antibodies was performed.

Example 7—Injection of Construct Containing WT Parkin in Non-Human Primates

Dose 2 ($1 \times 10^{13}$ gc/mL) was injected into the unilateral SN in 4 non-human primates: Antero-posterior: –8 mm (from anterior commissure); Lateral: 3.5 mm (from venous sinus); Ventral: –228.5 mm (from cortex). After a survival time of 6 weeks, both biochemical and histological assays were performed on samples.

Figure 15A:
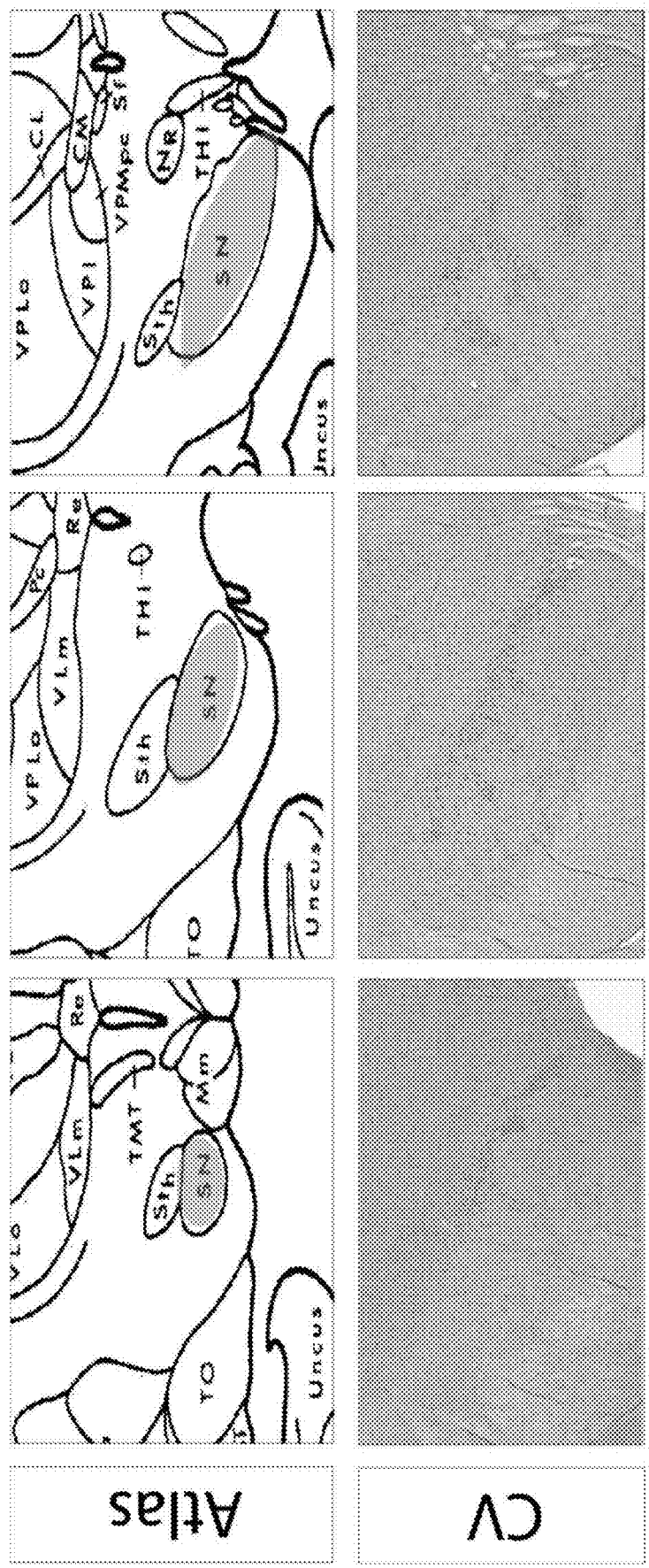
FIG. 15A-B shows the CV intact side of one of the animals injected with the wild type Parkin construct. Panel A and B show different views of case #4 (animal BV156).
Figure 15B:
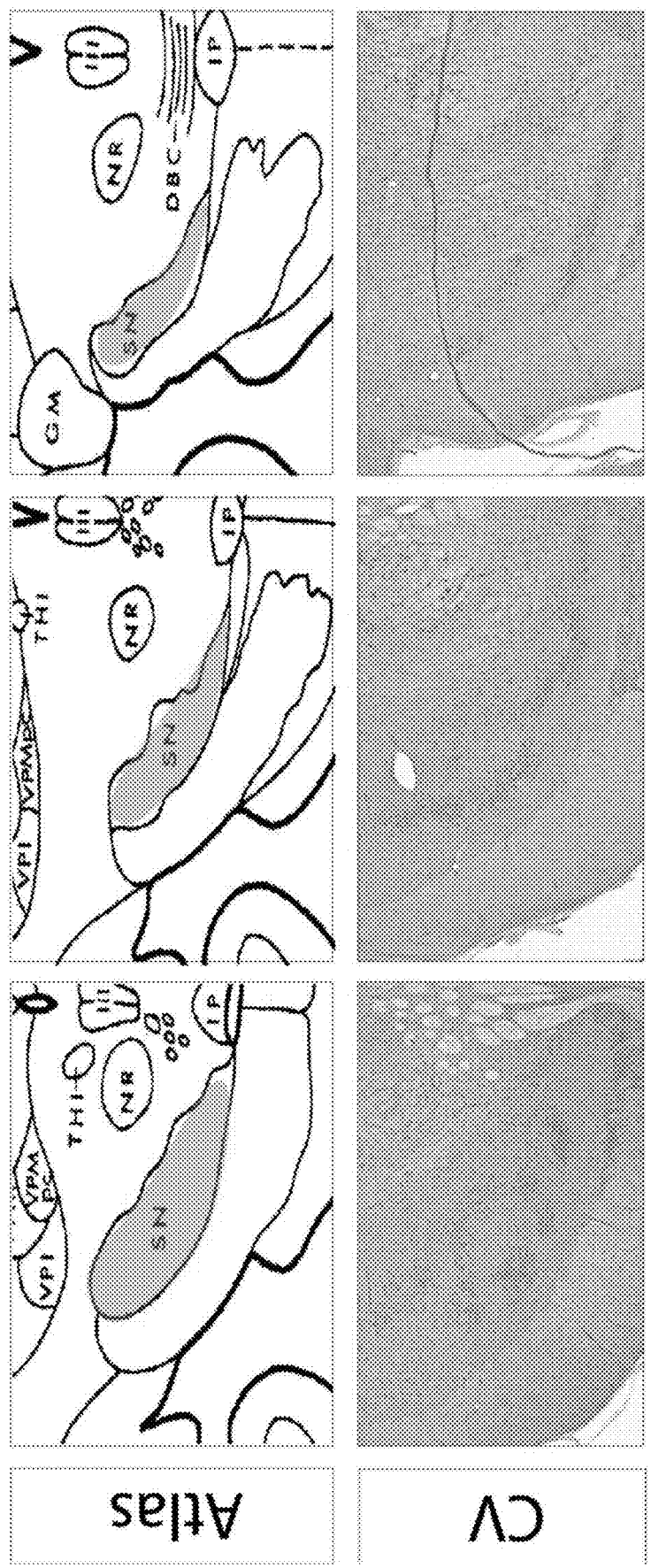

For the biochemical assays, 3 mm tissue punches from the caudate and putamen were tested for dopamine levels with HPLC, and TH levels were analyzed with Western blotting. For the histology analysis, the SN (intact; see FIGS. 15A-B) and punched tissue from the caudate and putamen were visualized using Parkin PRK8 (1:2000 dilution), Parkin 5C3 (1:1000 dilution), Cresyl violet staining, and TH (Pelfreeze) (1:5000 dilution).

Figure 16:
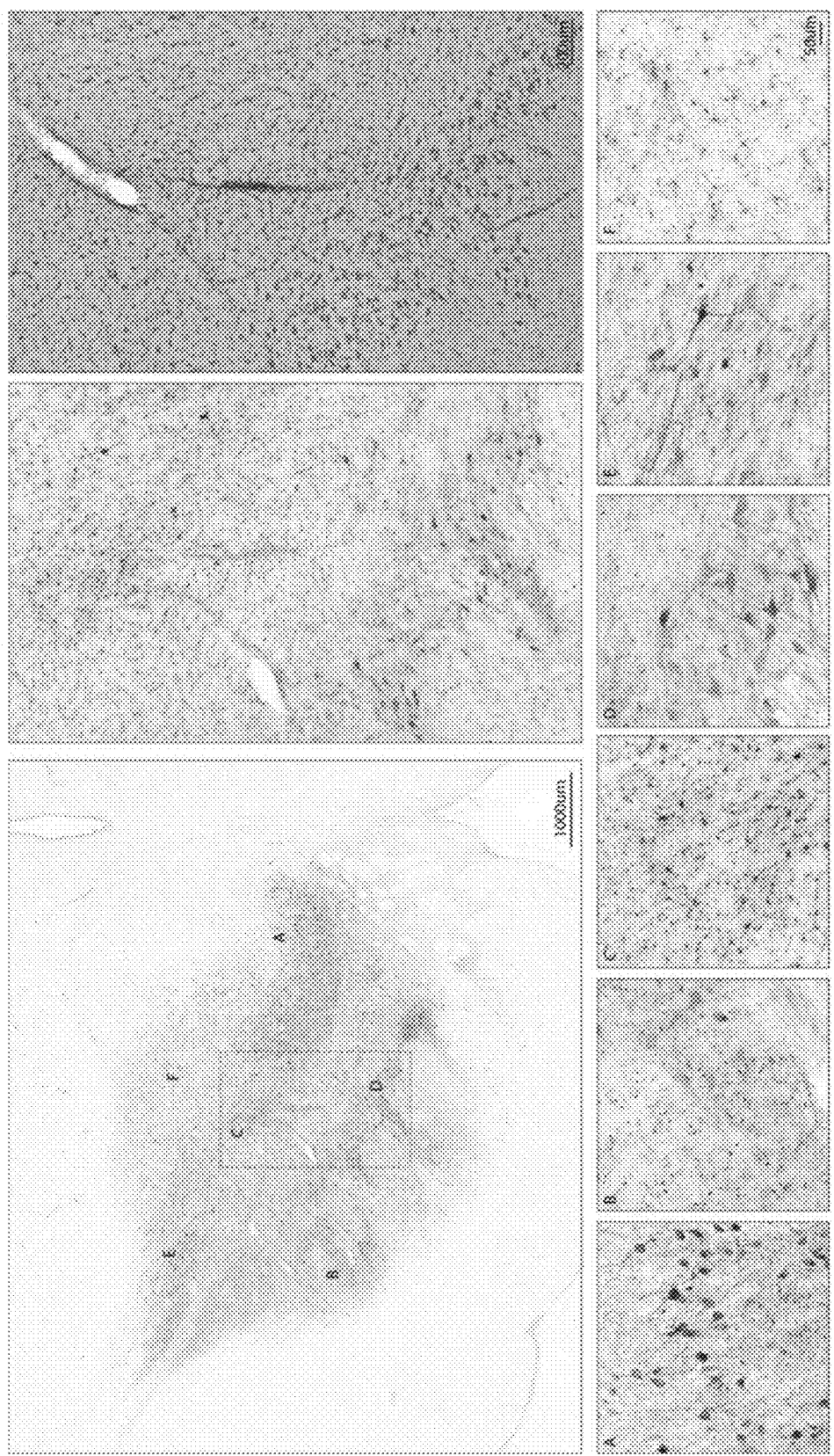
FIG. 16 shows that the wild type Parkin construct transduced both neuronal and glial-like profiles. This sample is from Case #1 (B0935).
Figure 17:
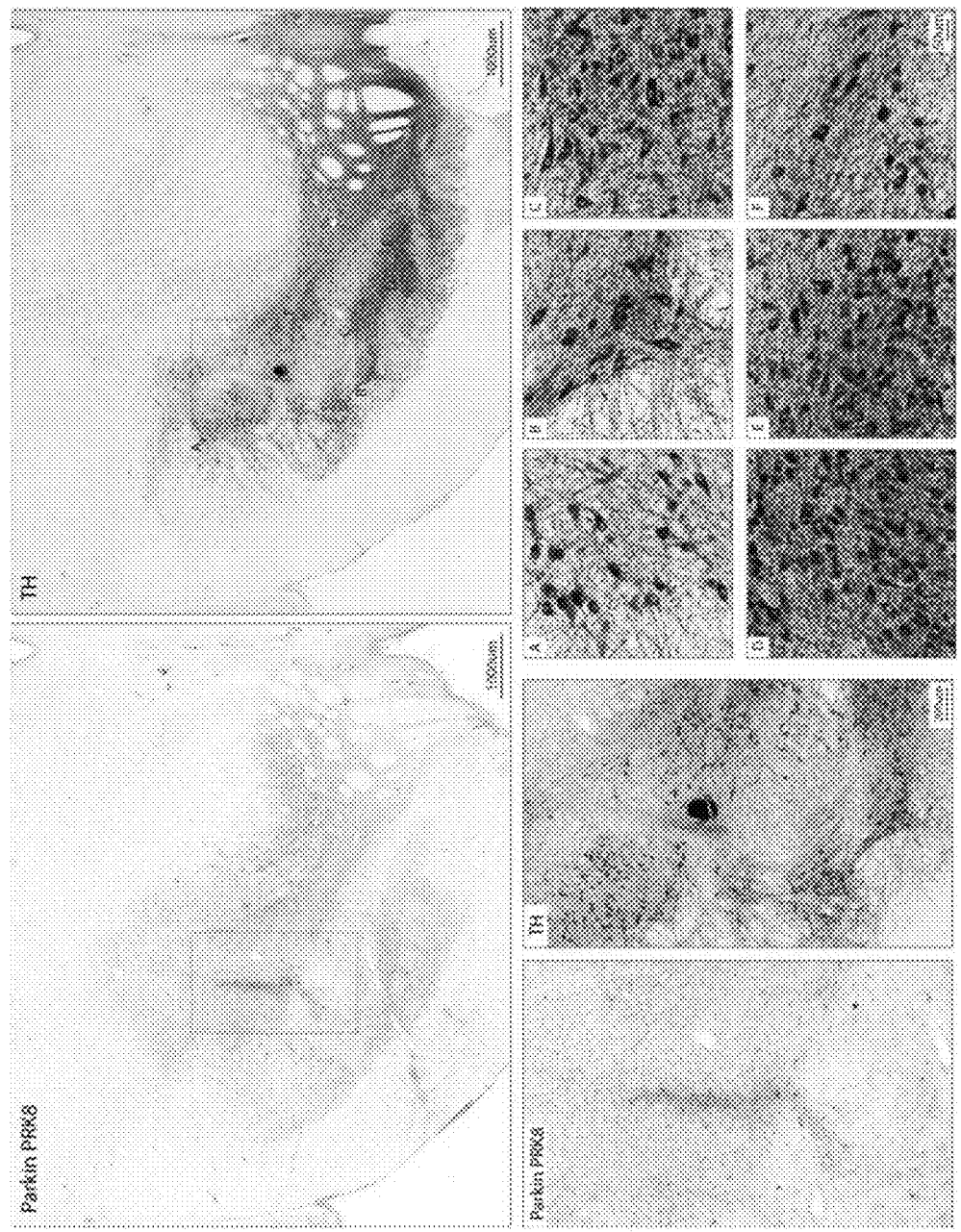
FIG. 17 shows sparse coverage of SN dopaminergic cells after administration with the wild type Parkin construct. This sample is from Case #3 (B0803).
Figure 18:
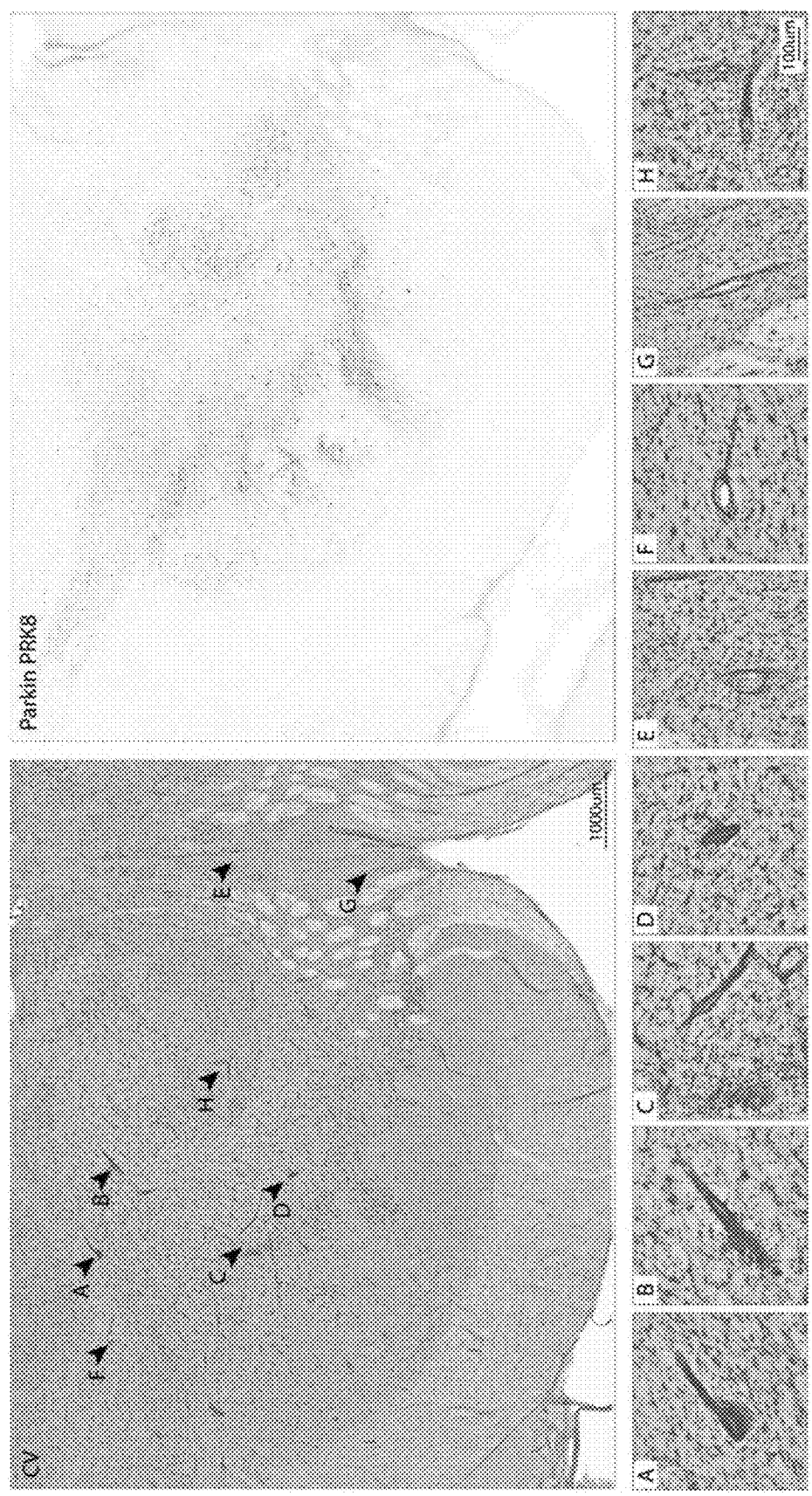
FIG. 18 shows a visible tissue reaction detected in Case #2 (BL926) after administration with the wild type Parkin construct.
Figure 19A:
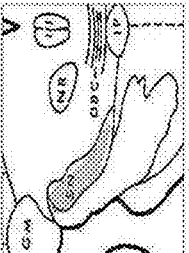
FIG. 19A-D show the histology of each of the four animals injected with Dose two of the wild type Parkin construct. Panel A is Case #1 (B0935); Panel B is Case #2 (BL926); Panel C is Case #3 (B0803); and Panel D is Case #4 (BV156).
Figure 19B:
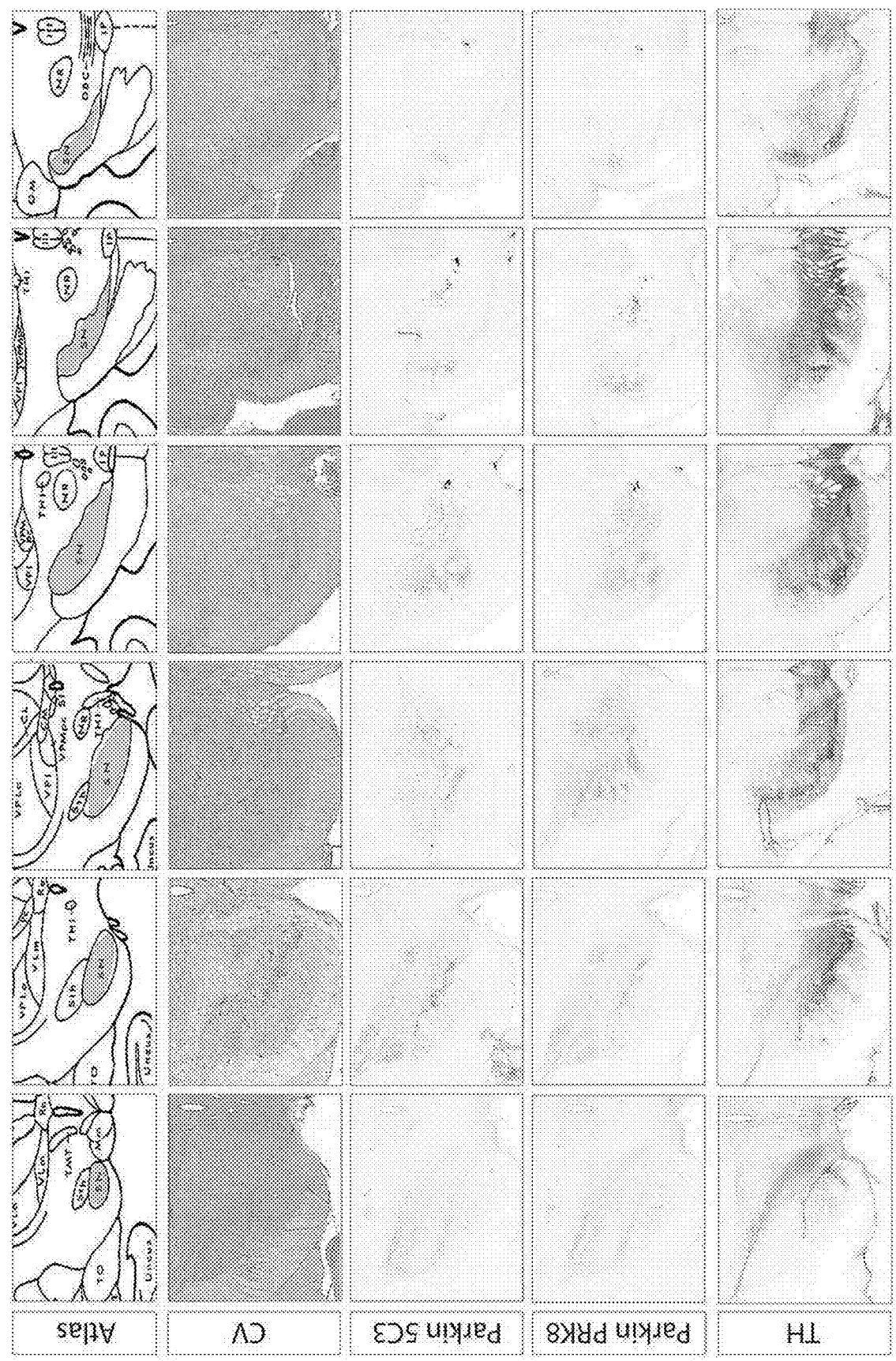
Figure 19C:
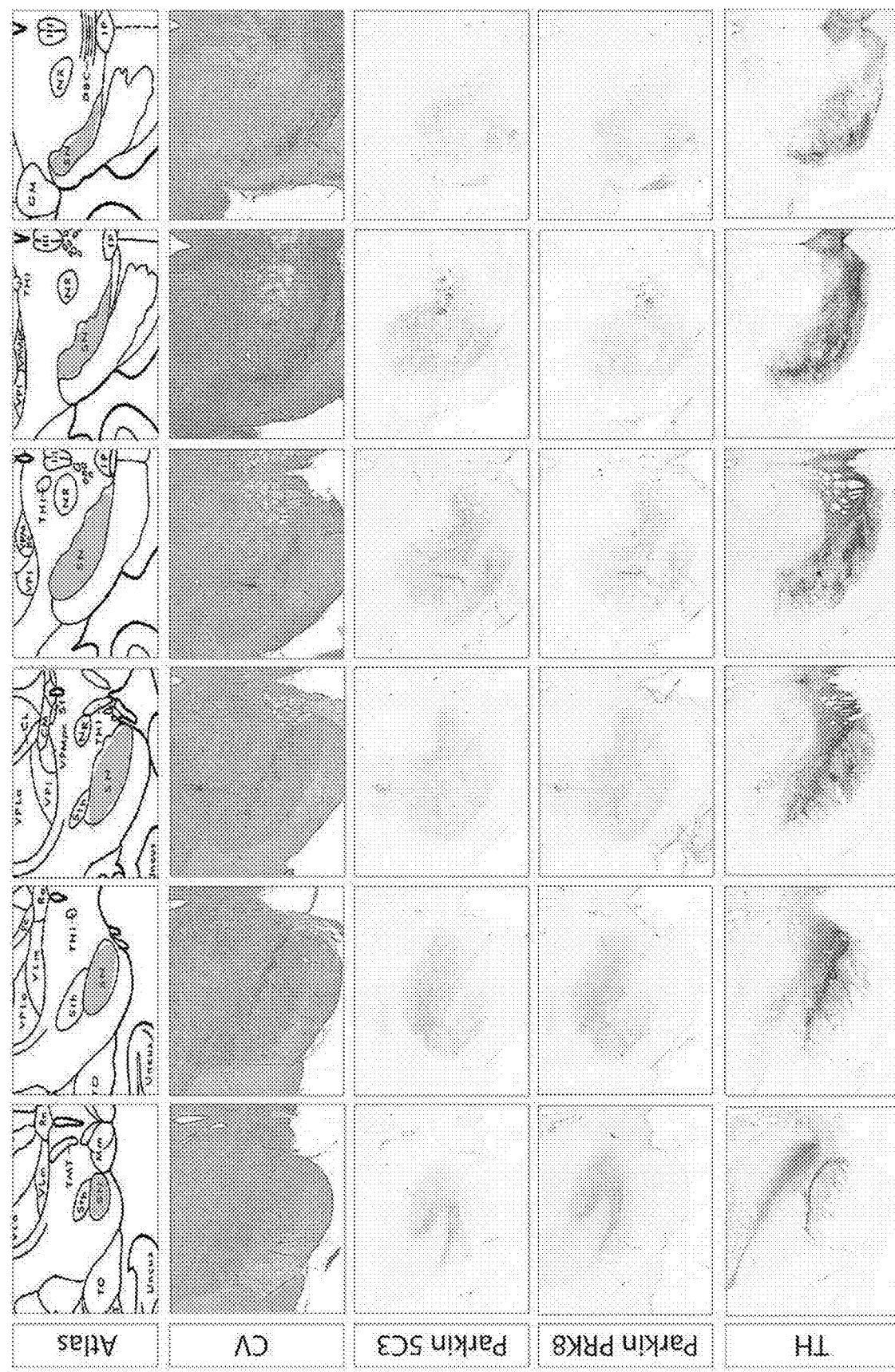
Figure 19D:
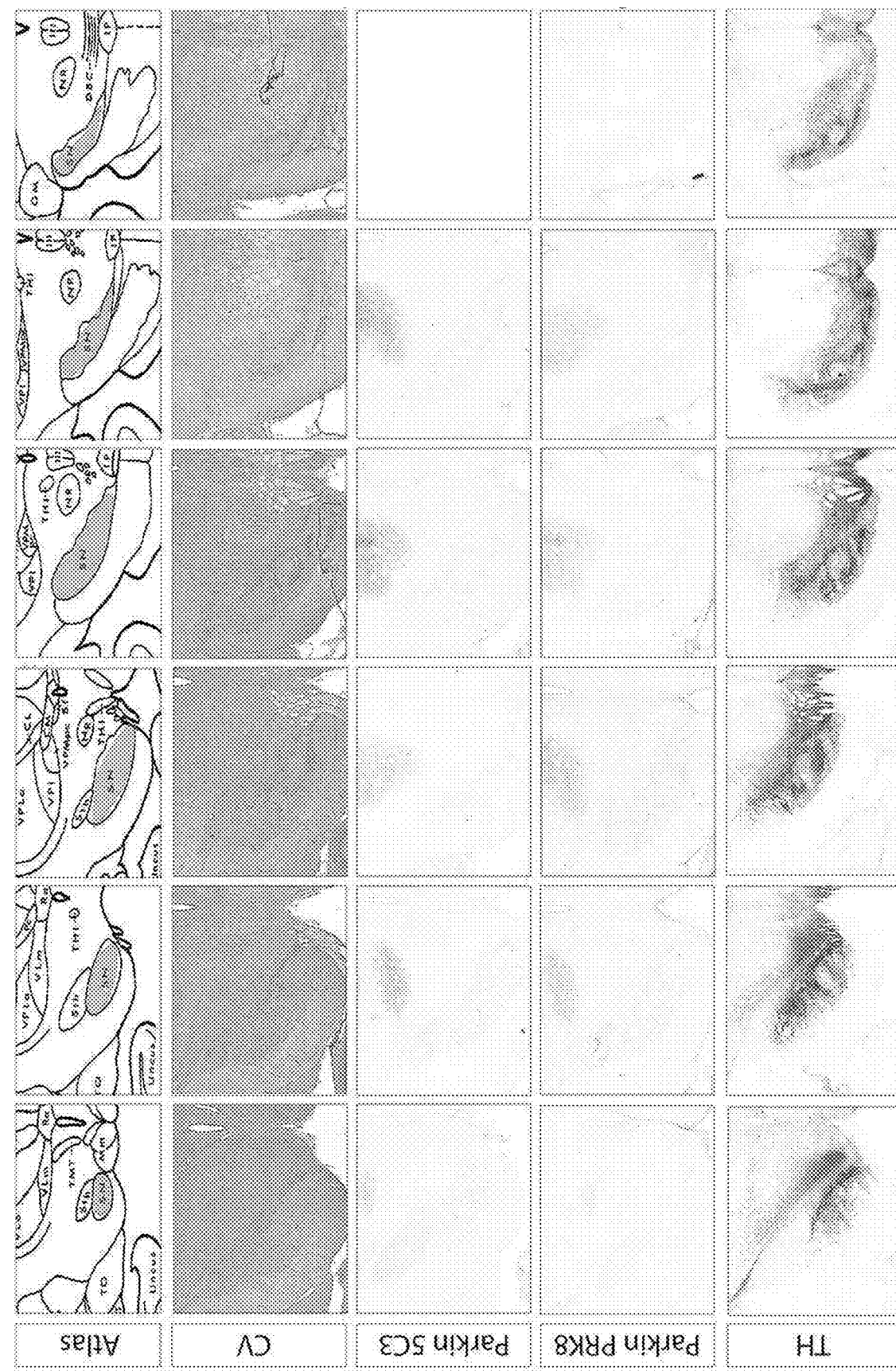

The AAV5 vector transduced both neuronal ang glial-like cells (FIG. 16), with sparse coverage of SN dopaminergic cells (FIG. 17). A tissue reaction was detected in once case (FIG. 18). The histological analysis of each of the four animals is found in FIG. 19A-D.

INCORPORATION BY REFERENCE

All publications, patents, and patent publications cited are incorporated by reference herein in their entirety for all purposes.

REFERENCES

Manfredsson et al. (2007) rAAV-medicated nigral human parkin over-expression partially ameliorates motor deficits via enhanced dopamine neurotransmission in a rat model of Parkinson's disease. *Experimental Neurology.* 207:289-301.

Niethammer et al. (2018) Gene therapy reduces Parkinson's disease symptoms by reorganizing functional brain connectivity. *Sci. Transl. Med* 10: eaau0713.

The invention claimed is:

1. A method of treating, or ameliorating Parkinson's Disease or a symptom thereof in a patient in need thereof, comprising administering a pharmaceutical composition comprising an AAV5 vector comprising a gene therapy construct comprising a parkin (PARK2) gene comprising a polynucleotide that encodes the polypeptide sequence selected from SEQ ID NOs: 4 or 6, wherein the method comprises administering the pharmaceutical composition to the brain of the patient.

2. The method of claim 1, wherein the PARK2 gene is a variant PARK2 gene that encodes a variant parkin polypeptide having greater auto-ubiquitination than a wild type parkin polypeptide comprising SEQ ID NO: 2.

3. The method of claim 2, wherein the variant PARK2 gene comprises the polynucleotide sequence selected from SEQ ID NOs: 3 and 5.

4. The method of claim 3, wherein the variant PARK2 gene consists of the polynucleotide sequence selected from any one of SEQ ID NOs: 3 and 5.

5. The method of claim 2, wherein the variant PARK2 gene is under control of a chicken-beta-actin (CBA) promoter.

6. The method of claim 5, wherein the AAV5 vector comprises from 5'-3':
a. an AAV2 ITR;
b. the CBA promoter;
C. the variant PARK2 gene comprises the polynucleotide sequence that encodes SEQ ID NO: 4;
d. a SV 40 poly A tail; and
e. an AAV2 ITR;
wherein the AAV also comprises an AAV2 Rep and AAVS cap genes.

7. The method of claim 6, wherein the AAV5 vector comprises SEQ ID NO: 3.

8. The method of claim 5, wherein the AAV5 vector comprises from 5'-3':
a. an AAV2 ITR;
b. the CBA promoter;
c. the variant PARK2 gene comprises the polynucleotide sequence that encodes SEQ ID NO: 6;
d. a SV40 poly A tail; and
e. an AAV2 ITR;
wherein the AAV also comprises an AAV2 Rep and AAV5 cap genes.

9. The method of claim 8, wherein the AAV5 vector comprises SEQ ID NO: 5.

10. The method of claim 1, wherein expression of the PARK2 gene is under control of a tissue specific promoter, a neuron-specific promoter, or a ubiquitous promoter.

11. The method of claim 10, wherein the PARK2 gene is under control of a promoter selected from the group consisting of: chicken-beta-actin (CBA), human beta actin (HuBa), cytomegalovirus (cMV), CAG, PGL, EF1-alpha, GAPDFI, SV40, FIBV, human synapsin (hSYN1), alpha-internexin (INA), nestin (NES), tyrosine hydroxylase (TH), forkhead box A2 (FOXA2), calmodulin-dependent protein kinase II (CAMKII), and neuron-specific enolase (NSE).

12. The method of claim 1, wherein the pharmaceutical composition is administered by intrathecal administration.

13. The method of claim 12, wherein the pharmaceutical composition is administered to the substantia nigra of the patient's brain.

14. The method of claim 13, wherein administration of the pharmaceutical composition results in expression of the parkin gene in neurons and glial cells.

15. The method of claim 14, wherein the neurons are dopaminergic neurons or oligodendrocytes.

16. The method of claim 14, wherein the glial cells are astrocytes.

17. The method of claim 1, wherein the one or more symptoms of Parkinson's Disease is selected from the group consisting of: motor deficits, tremors, bradykinesia, slowed movement, rigid muscles, impaired posture and balance, loss of automatic movements, speech changes, writing changes, depression, swallowing problems, decreased cardiac function, sleep disorders, dementia, cognitive problems, emotional changes including fear, anxiety, or loss of motivation, blood pressure changes, fatigue, pain, involuntary movements, shuffling gait, dizziness, amnesia, confusion, voice box spasms, distorted sense of smell, jaw stiffness or reduced facial expression, and weight loss.

18. The method of claim 1, wherein administration of the pharmaceutical composition increases the number of dopaminergic neurons in the patient.

19. A composition comprising an AAV5 vector wherein the AAV5 vector comprises from 5'-3':
a. an AAV2 ITR;
b. a CBA promoter;
c. a variant PARK2 gene comprising a polynucleotide sequence that encodes the sequence selected from SEQ ID NOs: 4 or 6;
d. a SV40 poly A tail; and
e. an AAV2 ITR;
wherein the AAV also comprises an AAV2 Rep and AAV5 cap genes.

20. A pharmaceutical composition comprising the composition of claim 19 and a pharmaceutically-acceptable buffer.

21. The pharmaceutical composition of claim 20, wherein the AAV5 vector comprises any one of SEQ ID NOs: 3 or 5.

22. The composition of claim 19, wherein the AAV5 vector comprises any one of SEQ ID NOs: 3 or 5.

* * * * *

UNITED STATES PATENT AND TRADEMARK OFFICE
CERTIFICATE OF CORRECTION

| | |
|---|---|
| PATENT NO. | : 12,133,897 B2 |
| APPLICATION NO. | : 17/327562 |
| DATED | : November 5, 2024 |
| INVENTOR(S) | : Jennifer Johnston |

It is certified that error appears in the above-identified patent and that said Letters Patent is hereby corrected as shown below:

In the Claims

At Claim 6, Column 201, Line 8, please delete "C." and insert therein --c.--

At Claim 6, Column 201, Line 10, please delete "SV 40" and insert therein --SV40--

At Claim 6, Column 201, Lines 12-13, please delete "AA VS" and insert therein --AAV5--

Signed and Sealed this
Twenty-second Day of April, 2025

Coke Morgan Stewart
*Acting Director of the United States Patent and Trademark Office*